(12) United States Patent
Dugan

(10) Patent No.: US 10,849,549 B2
(45) Date of Patent: *Dec. 1, 2020

(54) SYSTEMS, DEVICES, AND METHODS FOR TRACKING ABDOMINAL ORIENTATION AND ACTIVITY

(71) Applicant: Smart Human Dynamics, Inc., San Francisco, CA (US)

(72) Inventor: Stephen Dugan, San Francisco, CA (US)

(73) Assignee: Smart Human Dynamics, Inc., San Francisco, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 15/855,578

(22) Filed: Dec. 27, 2017

(65) Prior Publication Data

US 2018/0132778 A1 May 17, 2018

Related U.S. Application Data

(63) Continuation-in-part of application No. 14/663,453, filed on Mar. 20, 2015, now Pat. No. 9,918,673,
(Continued)

(51) Int. Cl.
*A61B 5/00* (2006.01)
*A61B 5/11* (2006.01)
(Continued)

(52) U.S. Cl.
CPC .......... *A61B 5/4343* (2013.01); *A61B 5/0022* (2013.01); *A61B 5/0059* (2013.01);
(Continued)

(58) Field of Classification Search
CPC ........ A61B 2503/02; A61B 2562/0219; A61B 5/0022; A61B 5/0059; A61B 5/0077;
(Continued)

(56) References Cited

U.S. PATENT DOCUMENTS 5,938,626 A 8/1999 Sugerman
6,095,991 A 8/2000 Krausman et al.
(Continued)

FOREIGN PATENT DOCUMENTS

CN 103096796 A 5/2013
CN 103462588 A 12/2013
(Continued)

OTHER PUBLICATIONS

Facco et al., "Abstracts LB1 and LB2", Feb. 6, 2015.
(Continued)

*Primary Examiner* — George Manuel
(74) *Attorney, Agent, or Firm* — Davis, Brown, Koehn, Shors & Roberts, P.C.; Matthew Warner-Blankenship

(57) ABSTRACT

The disclosed apparatus, systems and methods relate to tracking abdominal orientation and activity for purposes of preventing or treating conditions of pregnancy or other types of medical conditions. In certain specific embodiments, the system, device, or method relates to identifying abdominal orientation risk values, calculating and updating a cumulative risk value, comparing the cumulative risk value to a threshold, and outputting a warning when the cumulative risk value crosses the threshold.

20 Claims, 32 Drawing Sheets

Related U.S. Application Data which is a continuation of application No. 14/625,965, filed on Feb. 19, 2015, now Pat. No. 9,585,614.

(60) Provisional application No. 61/111,427, filed on Feb. 3, 2015, provisional application No. 62/059,557, filed on Oct. 3, 2014, provisional application No. 62/022,060, filed on Jul. 8, 2014, provisional application No. 61/986,665, filed on Apr. 30, 2014, provisional application No. 61/971,438, filed on Mar. 27, 2014.

(51) Int. Cl.

| | |
|---|---|
| *A61B 5/145* | (2006.01) |
| *A61B 5/08* | (2006.01) |
| *A61B 5/021* | (2006.01) |
| *A61B 5/107* | (2006.01) |
| *A61B 5/053* | (2006.01) |
| *G16H 50/30* | (2018.01) |
| *A61B 5/1455* | (2006.01) |
| *A61B 5/024* | (2006.01) |

(52) U.S. Cl.
CPC ............ *A61B 5/0077* (2013.01); *A61B 5/021* (2013.01); *A61B 5/053* (2013.01); *A61B 5/08* (2013.01); *A61B 5/1072* (2013.01); *A61B 5/1073* (2013.01); *A61B 5/1075* (2013.01); *A61B 5/1114* (2013.01); *A61B 5/1116* (2013.01); *A61B 5/1118* (2013.01); *A61B 5/1121* (2013.01); *A61B 5/14542* (2013.01); *A61B 5/4362* (2013.01); *A61B 5/6804* (2013.01); *A61B 5/6823* (2013.01); *A61B 5/6831* (2013.01); *A61B 5/7275* (2013.01); *A61B 5/746* (2013.01); *G16H 50/30* (2018.01); *A61B 5/02411* (2013.01); *A61B 5/1107* (2013.01); *A61B 5/14552* (2013.01); *A61B 5/4356* (2013.01); *A61B 5/6832* (2013.01); *A61B 2503/02* (2013.01); *A61B 2562/0219* (2013.01)

(58) Field of Classification Search
CPC ..... A61B 5/021; A61B 5/02411; A61B 5/053; A61B 5/08; A61B 5/1072; A61B 5/1073; A61B 5/1075; A61B 5/1107; A61B 5/1114; A61B 5/1116; A61B 5/1118; A61B 5/1121; A61B 5/14542; A61B 5/14552; A61B 5/4343; A61B 5/4356; A61B 5/4362; A61B 5/6804; A61B 5/6823; A61B 5/6831; A61B 5/6832; A61B 5/7275; A61B 5/746; G16H 50/30
See application file for complete search history.

(56) References Cited

U.S. PATENT DOCUMENTS

| | | | |
|---|---|---|---|
| 7,938,476 | B2 | 5/2011 | Brunelle et al. |
| 8,206,325 | B1 | 6/2012 | Najafi et al. |
| 8,587,439 | B2 | 11/2013 | Levine et al. |
| 8,643,494 | B1 | 2/2014 | Trout |
| 9,198,615 | B2 | 12/2015 | Levendowski |
| 2008/0221398 | A1 | 9/2008 | Ronchi et al. |
| 2012/0035508 | A1 | 2/2012 | Van Leer |
| 2012/0158437 | A1 | 6/2012 | Little et al. |
| 2013/0184611 | A1 | 7/2013 | Nichols |
| 2013/0211772 | A1 | 8/2013 | Ross |
| 2013/0237772 | A1 | 9/2013 | Pisani |
| 2013/0245436 | A1* | 9/2013 | Tupin, Jr. ............. A61B 5/0444 600/430 |
| 2014/0128778 | A1 | 5/2014 | Chan |
| 2014/0330132 | A1* | 11/2014 | Raskin ............... A61B 5/02427 600/479 |

FOREIGN PATENT DOCUMENTS

| | | |
|---|---|---|
| WO | 2005067796 A1 | 7/2005 |
| WO | 2010099764 A2 | 9/2010 |
| WO | 2013030703 A1 | 3/2013 |
| WO | 2013069004 A1 | 5/2013 |

OTHER PUBLICATIONS

Owusu et al., "Association of maternal sleep practices with pre-eclampsia, low birth weight, and stillbirth among Ghanaian women", "International Journal of Gynecology and Obstetrics", Jan. 1, 2013, pp. 261-265, vol. 121, Publisher: FIGO.

Stacey et al., "Association between maternal sleep practices and risk of late stillbirth: a case-control study", Jan. 1, 2011, pp. 1-6, Publisher: BMJ.

Xiong et al., "Association of preeclampsia with high birth weight for age", Jul. 1, 2000, pp. 148-155, vol. 183, No. 1, Publisher: AJOG.

Higuchi et al., "Effect of Lateral Tilt Angle on the Volume of the Abdominal Aorta and Inferior Vena Cava in Pregnant and Nonpregnant Women Determined by Magnetic Resonance Imaging", "Anesthesiology", Feb. 1, 2015, vol. 122, No. 2.

Drummond et al., "Effects of Posture on Limb Blood Flow in Late Pregnancy", "British Medical Journal", Jun. 15, 1974.

Lee et al., "Haemodynamic effects from aortocaval compression at different angles of lateral tilt in non-labouring term pregnant women", "British Journal of Anaesthesia", Jan. 1, 2012, pp. 950-956, vol. 109, No. 6.

Kanayama et al., "Hypolumbarlordosis a predisposing factor for preeclampsia", "European journal of obsetrics and gynecology", Jan. 1, 1997, Publisher: Elsevier.

Sharwood et al., "Hypotension in obstetric spinal anaesthesia: a lesson from pre-eclampsia", "British Journal of Anaesthesia", Mar. 3, 2009, vol. 102, No. 3.

Lisonkova et al., "Incidence of preeclampsia: risk factors and outcomes associated with earlyversus late-onset disease", Dec. 1, 2013, vol. 209, No. 6.

O'Brien et al., "Maternal sleep position: what do we know where do we go?", "BMC Pregnancy and Childbirth 2015", Jan. 1, 2015, vol. 15.

Chen et al., "Obstructive sleep apnea and the risk of adverse pregnancy outcomes", "American Journal of Obstetrics", Feb. 1, 2012, Publisher: AJOG.

Louis et al., "Perinatal Outcomes Associated With Obstructive Sleep Apnea in Obese Pregnant Women", "Obstet Gynecol", Nov. 1, 2012, vol. 120, No. 5, Publisher: NIH.

Bourjeily et al., "Pregnancy and fetal outcomes of symptoms of sleep disordered breathing", Jan. 1, 2010, vol. 36, No. 4, Publisher: ERS.

Li et al., "Presence of depressive symptoms during early pregnancy and the risk of preterm delivery: a prospective cohort study", "Human Reproduction", Jan. 1, 2009, pp. 146-153, vol. 24, No. 1.

Conde-Agudelo et al., "Risk factors for preeclampsia in a large cohort of Latin American and Caribbean women.", Jan. 1, 2000, pp. 75-83, vol. 107, No. 1.

Gordon et al., "Sleep Position, Fetal Growth Restriction, and Late-Pregnancy Stillbirth", "Obstetrics & Gynecology", Feb. 1, 2015, vol. 125, No. 2, Publisher: The American College of Obstetricians.

"Too much exercise in early pregnancy may cause preeclampsia", "Royal College of Obstetricians and Gynaecologists", Jan. 1, 2013, Publisher: RCOG.

(56) References Cited

OTHER PUBLICATIONS

Jeffreys et al., "Uterine blood flow during supine rest and exercise after 28 weeks of gestation", Jul. 19, 2006, Publisher: BJOG An International Journal of Obstetrics and Gynaecology.

* cited by examiner

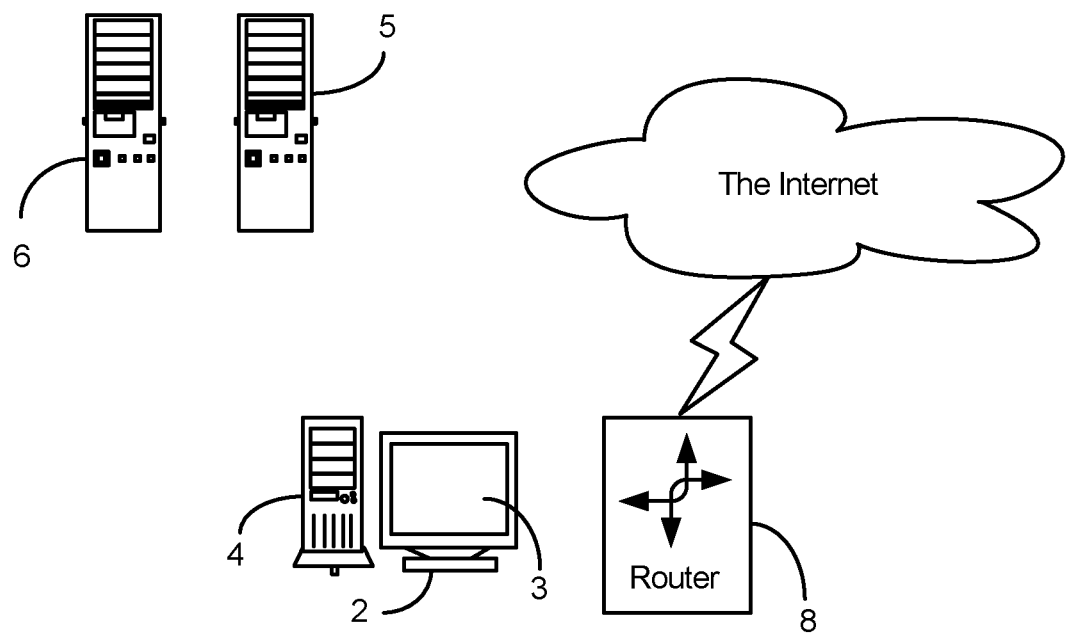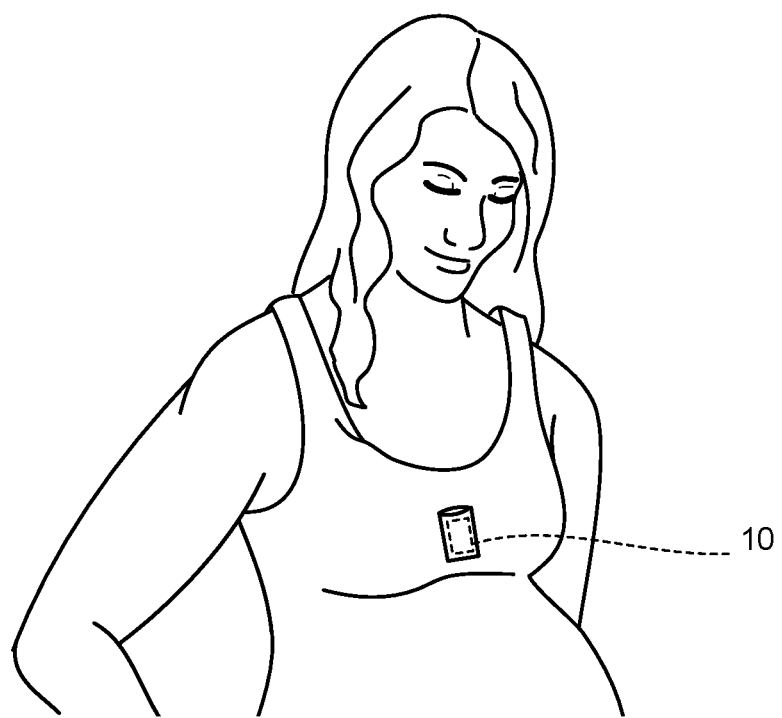
Fig. 1B

| | Theta | | | | | | | | | | | | | | | | | | | |
|---|---|---|---|---|---|---|---|---|---|---|---|---|---|---|---|---|---|---|---|---|
| Headstand | 180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | 170 | 0 | 0.12 | 0.24 | 0.36 | 0.48 | 0.59 | 0.70 | 0.80 | 0.90 | 0.98 | 0.90 | 0.80 | 0.70 | 0.60 | 0.49 | 0.38 | 0.27 | 0.15 | 0.03 |
| | 160 | 0 | 0.12 | 0.23 | 0.34 | 0.45 | 0.56 | 0.66 | 0.76 | 0.86 | 0.94 | 0.85 | 0.77 | 0.67 | 0.57 | 0.47 | 0.37 | 0.26 | 0.14 | 0.03 |
| | 150 | 0 | 0.11 | 0.21 | 0.32 | 0.42 | 0.52 | 0.61 | 0.70 | 0.79 | 0.87 | 0.79 | 0.71 | 0.62 | 0.53 | 0.44 | 0.34 | 0.24 | 0.14 | 0.03 |
| | 140 | 0 | 0.09 | 0.19 | 0.28 | 0.37 | 0.46 | 0.54 | 0.62 | 0.70 | 0.77 | 0.70 | 0.63 | 0.55 | 0.47 | 0.39 | 0.30 | 0.22 | 0.12 | 0.03 |
| | 130 | 0 | 0.08 | 0.16 | 0.24 | 0.31 | 0.39 | 0.46 | 0.52 | 0.59 | 0.65 | 0.59 | 0.53 | 0.46 | 0.40 | 0.35 | 0.26 | 0.19 | 0.11 | 0.03 |
| | 120 | 0 | 0.06 | 0.12 | 0.18 | 0.24 | 0.30 | 0.36 | 0.41 | 0.46 | 0.51 | 0.46 | 0.41 | 0.36 | 0.31 | 0.26 | 0.21 | 0.15 | 0.09 | 0.03 |
| | 110 | 0 | 0.04 | 0.09 | 0.13 | 0.17 | 0.21 | 0.25 | 0.28 | 0.32 | 0.35 | 0.32 | 0.29 | 0.25 | 0.22 | 0.19 | 0.15 | 0.11 | 0.07 | 0.03 |
| | 100 | 0 | 0.02 | 0.04 | 0.07 | 0.09 | 0.11 | 0.13 | 0.15 | 0.17 | 0.18 | 0.17 | 0.15 | 0.14 | 0.12 | 0.11 | 0.09 | 0.07 | 0.05 | 0.03 |
| Flat on stomach | 90 | 0 | 0.00 | 0.00 | 0.00 | 0.00 | 0.00 | 0.01 | 0.01 | 0.01 | 0.010 | 0.01 | 0.01 | 0.01 | 0.02 | 0.02 | 0.02 | 0.03 | 0.03 | 0.03 |
| | 80 | 0 | 0.00 | 0.01 | 0.01 | 0.01 | 0.01 | 0.01 | 0.01 | 0.02 | 0.02 | 0.03 | 0.03 | 0.03 | 0.03 | 0.03 | 0.03 | 0.03 | 0.03 | 0.03 |
| | 70 | 0 | 0.01 | 0.01 | 0.02 | 0.02 | 0.02 | 0.03 | 0.03 | 0.03 | 0.03 | 0.04 | 0.04 | 0.04 | 0.04 | 0.04 | 0.04 | 0.04 | 0.03 | 0.03 |
| | 60 | 0 | 0.01 | 0.01 | 0.02 | 0.03 | 0.03 | 0.04 | 0.04 | 0.04 | 0.05 | 0.05 | 0.05 | 0.05 | 0.05 | 0.05 | 0.04 | 0.04 | 0.04 | 0.03 |
| | 50 | 0 | 0.01 | 0.02 | 0.03 | 0.03 | 0.04 | 0.05 | 0.05 | 0.05 | 0.06 | 0.06 | 0.06 | 0.06 | 0.06 | 0.05 | 0.05 | 0.04 | 0.04 | 0.03 |
| | 40 | 0 | 0.01 | 0.02 | 0.03 | 0.04 | 0.05 | 0.06 | 0.06 | 0.06 | 0.07 | 0.07 | 0.07 | 0.06 | 0.06 | 0.06 | 0.05 | 0.04 | 0.04 | 0.03 |
| | 30 | 0 | 0.01 | 0.02 | 0.03 | 0.04 | 0.05 | 0.06 | 0.07 | 0.07 | 0.08 | 0.08 | 0.07 | 0.07 | 0.07 | 0.06 | 0.05 | 0.05 | 0.04 | 0.03 |
| | 20 | 0 | 0.01 | 0.02 | 0.03 | 0.04 | 0.05 | 0.06 | 0.07 | 0.08 | 0.08 | 0.08 | 0.08 | 0.08 | 0.07 | 0.06 | 0.06 | 0.05 | 0.04 | 0.03 |
| | 10 | 0 | 0.01 | 0.02 | 0.03 | 0.05 | 0.06 | 0.07 | 0.08 | 0.08 | 0.09 | 0.09 | 0.08 | 0.08 | 0.07 | 0.07 | 0.06 | 0.05 | 0.04 | 0.03 |
| Tilted forward | 0 | 0 | 0.01 | 0.02 | 0.04 | 0.05 | 0.06 | 0.07 | 0.08 | 0.09 | 0.100 | 0.09 | 0.08 | 0.08 | 0.07 | 0.07 | 0.06 | 0.05 | 0.04 | 0.03 |
| Standing upright | -10 | 0 | 0.01 | 0.03 | 0.04 | 0.05 | 0.07 | 0.08 | 0.09 | 0.10 | 0.11 | 0.10 | 0.09 | 0.08 | 0.08 | 0.07 | 0.06 | 0.05 | 0.04 | 0.03 |
| | -20 | 0 | 0.02 | 0.04 | 0.06 | 0.07 | 0.09 | 0.11 | 0.13 | 0.14 | 0.15 | 0.14 | 0.13 | 0.11 | 0.10 | 0.09 | 0.08 | 0.06 | 0.05 | 0.03 |
| | -30 | 0 | 0.03 | 0.05 | 0.08 | 0.11 | 0.13 | 0.16 | 0.18 | 0.20 | 0.22 | 0.20 | 0.18 | 0.16 | 0.14 | 0.12 | 0.10 | 008 | 0.06 | 0.03 |
| Tilted backward | -40 | 0 | 0.04 | 0.08 | 0.11 | 0.15 | 0.19 | 0.22 | 0.25 | 0.28 | 0.31 | 0.28 | 0.26 | 0.23 | 0.20 | 0.17 | 0.14 | 0.10 | 0.07 | 0.03 |
| | -50 | 0 | 0.05 | 0.10 | 0.15 | 0.20 | 0.25 | 0.30 | 0.34 | 0.38 | 0.42 | 0.38 | 0.35 | 0.31 | 0.26 | 0.22 | 0.18 | 0.13 | 0.08 | 0.03 |
| | -60 | 0 | 0.07 | 0.14 | 0.20 | 0.27 | 0.33 | 0.39 | 0.45 | 0.50 | 0.55 | 0.50 | 0.45 | 0.40 | 0.34 | 0.28 | 0.22 | 0.16 | 0.10 | 0.03 |
| | -70 | 0 | 0.09 | 0.17 | 0.25 | 0.33 | 0.41 | 0.49 | 0.56 | 0.63 | 0.69 | 0.63 | 0.56 | 0.50 | 0.43 | 0.35 | 0.28 | 0.20 | 0.11 | 0.03 |
| | -80 | 0 | 0.10 | 0.21 | 0.31 | 0.41 | 0.50 | 0.60 | 0.68 | 0.77 | 0.84 | 0.77 | 0.69 | 0.60 | 0.52 | 0.43 | 0.33 | 0.23 | 0.13 | 0.03 |
| Flat on back | -90 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -100 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -110 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -120 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -130 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -140 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -150 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -160 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -170 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| Headstand | -180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | | -90 | -80 | -70 | -60 | -50 | -40 | -30 | -20 | -10 | 0 | 10 | 20 | 30 | 40 | 50 | 60 | 70 | 80 | 90 Phi |
| | | On left side | | | | | | | | | Middle | | | | | | | | | On right side |

Fig. 10A

| | Theta | -90 | -80 | -70 | -60 | -50 | -40 | -30 | -20 | -10 | 0 | 10 | 20 | 30 | 40 | 50 | 60 | 70 | 80 | 90 |
|---|---|---|---|---|---|---|---|---|---|---|---|---|---|---|---|---|---|---|---|---|
| Headstand | 180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | 170 | 0 | 0.12 | 0.24 | 0.36 | 0.48 | 0.59 | 0.70 | 0.80 | 0.90 | 0.98 | 0.90 | 0.80 | 0.70 | 0.60 | 0.49 | 0.38 | 0.27 | 0.15 | 0.03 |
| | 160 | 0 | 0.12 | 0.23 | 0.34 | 0.45 | 0.56 | 0.66 | 0.76 | 0.85 | 0.94 | 0.86 | 0.77 | 0.67 | 0.57 | 0.47 | 0.37 | 0.26 | 0.14 | 0.03 |
| | 150 | 0 | 0.11 | 0.21 | 0.32 | 0.42 | 0.52 | 0.61 | 0.70 | 0.79 | 0.87 | 0.79 | 0.71 | 0.62 | 0.53 | 0.44 | 0.34 | 0.24 | 0.14 | 0.03 |
| | 140 | 0 | 0.09 | 0.19 | 0.28 | 0.37 | 0.46 | 0.54 | 0.62 | 0.70 | 0.77 | 0.70 | 0.63 | 0.55 | 0.47 | 0.39 | 0.30 | 0.22 | 0.12 | 0.03 |
| | 130 | 0 | 0.08 | 0.16 | 0.24 | 0.31 | 0.39 | 0.46 | 0.52 | 0.59 | 0.65 | 0.59 | 0.53 | 0.46 | 0.40 | 0.35 | 0.26 | 0.19 | 0.11 | 0.03 |
| | 120 | 0 | 0.06 | 0.12 | 0.18 | 0.24 | 0.30 | 0.36 | 0.41 | 0.46 | 0.51 | 0.46 | 0.41 | 0.36 | 0.31 | 0.26 | 0.21 | 0.15 | 0.09 | 0.03 |
| | 110 | 0 | 0.04 | 0.09 | 0.13 | 0.17 | 0.21 | 0.25 | 0.29 | 0.32 | 0.35 | 0.32 | 0.29 | 0.25 | 0.22 | 0.19 | 0.15 | 0.11 | 0.07 | 0.03 |
| | 100 | 0 | 0.02 | 0.04 | 0.07 | 0.09 | 0.11 | 0.13 | 0.15 | 0.17 | 0.18 | 0.17 | 0.15 | 0.14 | 0.12 | 0.11 | 0.09 | 0.07 | 0.05 | 0.03 |
| Flat on stomach | 90 | 0 | 0.00 | 0.00 | 0.00 | 0.00 | 0.00 | 0.01 | 0.01 | 0.01 | 0.010 | 0.01 | 0.01 | 0.01 | 0.02 | 0.02 | 0.02 | 0.03 | 0.03 | 0.03 |
| | 80 | 0 | 0.01 | 0.02 | 0.03 | 0.04 | 0.05 | 0.06 | 0.07 | 0.08 | 0.09 | 0.08 | 0.07 | 0.07 | 0.06 | 0.06 | 0.05 | 0.05 | 0.04 | 0.03 |
| | 70 | 0 | 0.02 | 0.04 | 0.06 | 0.08 | 0.10 | 0.12 | 0.14 | 0.15 | 0.17 | 0.15 | 0.14 | 0.13 | 0.11 | 0.10 | 0.08 | 0.07 | 0.05 | 0.03 |
| | 60 | 0 | 0.03 | 0.06 | 0.09 | 0.12 | 0.15 | 0.17 | 0.20 | 0.22 | 0.25 | 0.22 | 0.20 | 0.18 | 0.16 | 0.14 | 0.11 | 0.09 | 0.06 | 0.03 |
| | 50 | 0 | 0.04 | 0.08 | 0.12 | 0.15 | 0.19 | 0.22 | 0.26 | 0.29 | 0.31 | 0.29 | 0.26 | 0.23 | 0.20 | 0.17 | 0.14 | 0.10 | 0.07 | 0.03 |
| | 40 | 0 | 0.05 | 0.09 | 0.14 | 0.18 | 0.22 | 0.27 | 0.30 | 0.34 | 0.38 | 0.34 | 0.31 | 0.27 | 0.24 | 0.20 | 0.16 | 0.12 | 0.08 | 0.03 |
| Tilted forward | 30 | 0 | 0.05 | 0.10 | 0.16 | 0.21 | 0.25 | 0.30 | 0.34 | 0.39 | 0.42 | 0.39 | 0.35 | 0.31 | 0.27 | 0.22 | 0.18 | 0.13 | 0.08 | 0.03 |
| | 20 | 0 | 0.06 | 0.11 | 0.17 | 0.22 | 0.28 | 0.33 | 0.37 | 0.42 | 0.46 | 0.42 | 0.38 | 0.33 | 0.29 | 0.24 | 0.19 | 0.14 | 0.09 | 0.03 |
| | 10 | 0 | 0.06 | 0.12 | 0.18 | 0.23 | 0.29 | 0.34 | 0.39 | 0.44 | 0.48 | 0.44 | 0.39 | 0.35 | 0.30 | 0.25 | 0.20 | 0.14 | 0.09 | 0.03 |
| Standing upright | 0 | 0 | 0.06 | 0.12 | 0.18 | 0.24 | 0.30 | 0.35 | 0.41 | 0.45 | 0.500 | 0.46 | 0.41 | 0.36 | 0.31 | 0.26 | 0.21 | 0.15 | 0.09 | 0.03 |
| | -10 | 0 | 0.06 | 0.12 | 0.19 | 0.25 | 0.30 | 0.36 | 0.41 | 0.46 | 0.51 | 0.46 | 0.42 | 0.37 | 0.32 | 0.26 | 0.21 | 0.15 | 0.09 | 0.03 |
| | -20 | 0 | 0.07 | 0.13 | 0.19 | 0.26 | 0.32 | 0.37 | 0.43 | 0.48 | 0.53 | 0.48 | 0.43 | 0.38 | 0.33 | 0.27 | 0.22 | 0.16 | 0.10 | 0.03 |
| | -30 | 0 | 0.07 | 0.14 | 0.21 | 0.27 | 0.34 | 0.40 | 0.46 | 0.52 | 0.57 | 0.52 | 0.46 | 0.41 | 0.35 | 0.29 | 0.23 | 0.17 | 0.11 | 0.03 |
| Tilted backward | -40 | 0 | 0.08 | 0.15 | 0.23 | 0.30 | 0.37 | 0.44 | 0.50 | 0.56 | 0.62 | 0.56 | 0.50 | 0.44 | 0.38 | 0.32 | 0.25 | 0.18 | 0.11 | 0.03 |
| | -50 | 0 | 0.08 | 0.17 | 0.25 | 0.33 | 0.41 | 0.48 | 0.55 | 0.62 | 0.68 | 0.62 | 0.55 | 0.48 | 0.42 | 0.35 | 0.27 | 0.19 | 0.12 | 0.03 |
| | -60 | 0 | 0.09 | 0.18 | 0.27 | 0.36 | 0.45 | 0.53 | 0.61 | 0.68 | 0.75 | 0.68 | 0.61 | 0.54 | 0.46 | 0.38 | 0.30 | 0.21 | 0.13 | 0.03 |
| | -70 | 0 | 0.10 | 0.20 | 0.30 | 0.40 | 0.50 | 0.59 | 0.67 | 0.75 | 0.83 | 0.75 | 0.68 | 0.59 | 0.51 | 0.42 | 0.33 | 0.23 | 0.14 | 0.03 |
| | -80 | 0 | 0.11 | 0.22 | 0.33 | 0.44 | 0.55 | 0.65 | 0.74 | 0.83 | 0.91 | 0.83 | 0.74 | 0.65 | 0.56 | 0.46 | 0.36 | 0.25 | 0.15 | 0.03 |
| Flat on back | -90 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -100 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -110 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -120 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -130 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -140 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -150 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -160 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -170 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| Headstand | -180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | Phi | -90 | -80 | -70 | -60 | -50 | -40 | -30 | -20 | -10 | 0 | 10 | 20 | 30 | 40 | 50 | 60 | 70 | 80 | 90 |
| | | On left side | | | | | | | | | Middle | | | | | | | | | On right side |

Fig. 10B

| Factor | Relative Risk | Factor | Relative Risk |
|---|---|---|---|
| Maternal age (years) | | Cigarette Smoking | |
| 41931 | 0.94 | No | 1 |
| 20-34 | 1 | 1-9 cigarettes per day | 0.79 |
| 35 or older | 1.67 | 10 or more cigarettes per day | 0.39 |
| Mother's education | | Body Mass index (kg/m2) | |
| None | 1 | 19.8 or less | 0.57 |
| Elementary | 1.05 | 19.9 to 26.0 | 1 |
| Secondary | 1.28 | 26.1 to 29 | 1.57 |
| University | 1.08 | Greater than 29 | 2.81 |
| Living with infant's father | | Type of Birth | |
| No | 1.21 | Single | 1 |
| Yes | 1 | Multiple | 2.1 |
| Parity (previous births) | | Fetal malformation | |
| 0 | 2.38 | No | 1 |
| 1 or more | 1 | Yes | 1.26 |
| Previous abortion | | Gestational diabetes mellitus | |
| No | 1.13 | No | 1 |
| Yes | 1 | Yes | 1.93 |
| History of chronic hypertension | | Due Date | |
| No | 1 | | |
| Yes | 1.99 | | |

Fig. 12

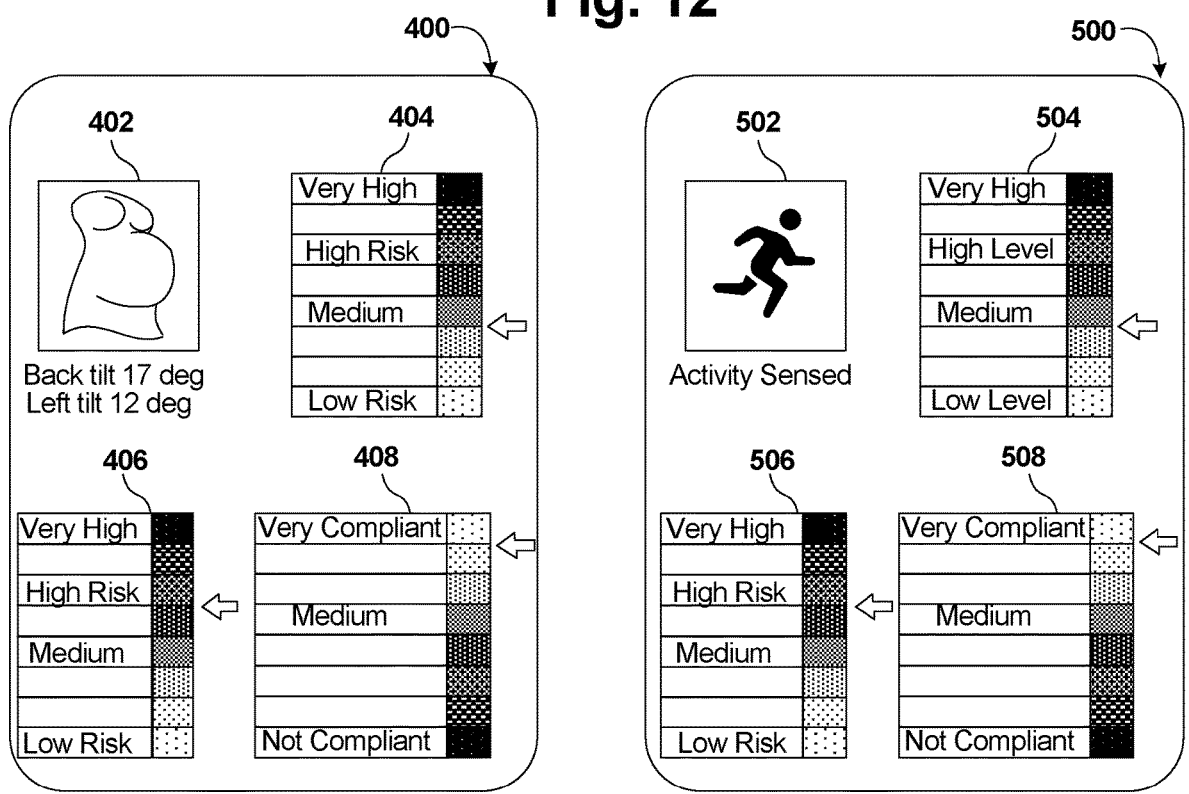

Fig. 13     Fig. 14

SYSTEMS, DEVICES, AND METHODS FOR TRACKING ABDOMINAL ORIENTATION AND ACTIVITY

CROSS-REFERENCE TO RELATED APPLICATIONS

This is a continuation-in-part of U.S. Pat. No. 9,918,673 issued Mar. 20, 2018 entitled "Systems, Devices, and Methods for Tracking Abdominal Orientation and Activity," which claimed priority to U.S. Pat. No. 9,585,614 entitled "Systems, Devices, and Methods for Tracking Abdominal Orientation and Activity," issued Mar. 7, 2017, which claimed priority to U.S. Provisional Application 61/971,438, filed Mar. 27, 2014 and entitled "A Method and Device to Assess and Alter Abdominal Orientation;" U.S. Provisional Application 61/986,665, filed Apr. 30, 2014 and entitled "Systems, Devices, and Methods for Tracking Abdominal Orientation and Activity;" U.S. Provisional Application 62/022,060, filed Jul. 8, 2014 and entitled "Systems, Devices, and Methods for Tracking Abdominal Orientation and Activity;" U.S. Provisional Application 62/059,557, filed Oct. 3, 2014 and entitled "Systems, Devices, and methods for Reducing Preterm Birth in Pregnant Women;" and U.S. Provisional Application 62/111,427, filed Feb. 3, 2015 and entitled "Systems, Devices, and Methods for Tracking Abdominal Orientation and Activity," all of which are hereby incorporated by reference in their entirety under 35 U.S.C. § 119(e).

TECHNICAL FIELD

The disclosed devices, systems and methods relate to sensing technologies and algorithms to assess and treat clinical conditions related to the abdomen and monitor pregnancy health and outcomes.

BACKGROUND

The disclosure relates to apparatuses, systems and methods for monitoring the abdomen during pregnancy, and assessing fetal risk, particularly while sleeping.

Medical evidence suggests that large amounts of mass or pressure in the abdominal region can lead to serious health consequences. Two very closely related examples of this are intra-abdominal hypertension ("IAH") and abdominal compartment syndrome ("ACS"). In these conditions, fluid within the abdominal space accumulates in such large volumes that the abdominal wall stretches to its elastic limit. Once it can no longer expand, additional fluid leaking into the tissue results in a rapid rises in the pressure within the closed space. Initially, this increase in pressure causes mild to moderate organ dysfunction (as seen in IAH). If the pressure continues to rise to higher levels, organs may begin to fail completely (as seen in ACS), which can lead to death.

A similar pathogenesis is observed in pregnant women, who also can have negative clinical responses to their large abdominal masses. The abdomen as a whole may apply different amounts of pressure on intra-abdominal tissues and organs depending upon its orientation. Compression of abdominal veins by the growing uterus explains many symptoms of preeclampsia. Inferior vena cava ("IVC") compression has been shown to decreased flow in the uterine, portal, hepatic, splenic, and renal veins. This reduced flow directly or indirectly contributes to lower extremity edema, fetal-placental ischemia, a glomerulopathy with proteinuria, and hypertension. Placental-fetal ischemia can lead to expression of soluble fms-like tyrosine kinase1 ("sFLT") and endoglin which have been shown to cause additional diffuse endovascular damage. Increased renal venous pressure could lead to an increased release of renin with conversion of angiotensinogen to angiotensin and secretion of aldosterone, leading to sodium and water retention, and increased systolic and diastolic blood pressure. In addition, IVC flow restriction would be expected to decrease venous return from the lower extremities and lead to the peripheral edema commonly present in preeclamptic women.

Preeclampsia is significantly more common in women whose abdomen has not been previously stretched, in severely obese women, in women who have a large time gap between pregnancies, in multi-fetal pregnancies, and is twice as frequent in women with preexisting chronic hypertension. Further, preeclampsia almost never occurs prior to 20 weeks (when fetus starts to gain significant mass), and its risk increases incrementally every week until delivery at which point it precipitously drops to almost zero. Women with preeclampsia have a 40% increased incidence of delivering a baby with high birth weight for gestational age. Additionally, preeclampsia rates are significantly higher in women with hypolumbarlordosis, a purely mechanical abnormality of the spine that positions the uterus in more direct contact with the IVC.

Traditionally, obstetricians have advised pregnant women with preeclampsia or other hypertensive disorders to avoid lying in the supine position and to go on bed rest for periods of time; however, these recommendations are often incomplete as they only frame the issue in terms of "good positions" (e.g. bed rest, laying on left side) and "bad positions" (e.g. laying supine). As a result, there is a need in the art for a method of developing more tailored recommendations for pregnant women with preeclampsia or other hypertensive disorders.

Various prior art home-use wearable pregnancy devices monitor metrics such as fetal heart rate and uterine contractions. This data may improve resultant care in a small number of cases, they typically result in urgent reactionary medicine in the last month of gestation, and frequently generate false positive alerts. In contrast, the presently disclosed devices, systems and methods were developed on the premise that there are a large number of user physiologies and behaviors that have profound impacts on pregnancy outcomes that can be monitored and improved throughout pregnancy.

Many complications of pregnancy which cannot simply be fixed once they manifest. Despite decades of research into the etiology of preeclampsia, its exact pathogenesis remains uncertain; however, it is becoming increasingly apparent that preeclampsia is directly related to underlying placental pathology and dysfunction that develop over many months. Because preeclampsia is not a disease that can be fixed at the end of pregnancy, prevention is important. The various implementations of the system discussed herein relate to the acquisition of risk factor data relating to the user's physical position, such as when sleeping, snoring and the like.

As most cases of preeclampsia occur at the end of pregnancy, the best way to prevent the majority of cases is to delay onset of dangerously high blood pressure until the pregnancy is full-term. The presently disclosed system tracks the adjustable factors in pregnancy that can prevent diseases and negative conditions. By way of example, these adjustable factors include the following. Sleep disordered breathing leads to hypertension in both pregnant and non-pregnant individuals. Similarly, snoring and sleep apnea are highly correlated to hypertensive diseases of pregnancy such as preeclampsia, as well as gestational diabetes and premature birth. Uterine artery blood flow and fetal oxygenation are both shown to significantly decrease in the supine position. Numerous studies have now shown that women who spend significant time in reclined and supine positions have much higher rates of stillbirth and intrauterine growth restriction. Depression and stress double the risk of preterm birth even after covariants such as low economic status and drug use are excluded. This is not surprising as depression is known to cause hypertension and increase placental and fetal cortisol levels.

The placenta serves as the lungs, kidneys, liver, endocrine system, and immune defense of the fetus. Despite its enormous importance, the placenta is arguably the least understood of all human organs. This is partly because the development of the human placenta cannot be invasively studied because it only exists during pregnancy at which time it is performing life-maintaining duties for the fetus. Not surprisingly, as we learn more about this mysterious organ, we also learn of its great importance in protecting the fetus from potential hazards during the pregnancy.

There is a need in the art for improved fetal monitoring devices, systems and methods.

BRIEF SUMMARY

Discussed herein are various pregnancy health improvement systems, methods and devices. In some embodiments, a wearable device for capturing certain physiological parameters and delivering feedback to the user is provided. The device may include one or more sensors which determine certain physiological parameters and a microcontroller that receives and stores orientation data from the sensors and uses an algorithm (and/or is configured) to estimate the level of clinical risk over various time scales based on those parameters. The wearable device may further include a communication device which conveys periodic updates and alerts to the user on their current risk level, either instantaneously or cumulatively.

Physiological parameters can include abdominal/body orientation, snoring, blood oxygen, blood pressure, location of center of gravity, activities like running, walking, driving, sleeping, body heat, altitude tracking, pressure readings, temperature readings, and/or user pedometer readings, breathing during sleep, fetal activity monitoring (fetal kicks), fetal heart rate monitoring, uterine contraction monitoring, and fetal ECG monitoring, respiration characteristics, tension, temperature (measured at any variety of locations on or in the body), and hemodynamic flow restriction.

In certain embodiments, the present system may be used as a preventative measure in high risk pregnancies to slow the progression of placental vascular pathology. In other embodiments, the device may be used to prevent or treat pregnancy complications or other abdominal-related conditions. The device could be specialized for each user depending on a variety of factors, including, but not limited to, user's height, weight, age, length of gestation, blood pressure, diagnostic test results, time since diagnosis, prior number of device alerts, or doctor and user preference regarding the restrictiveness of their daily activities. The device may be strapped to the body with elastic, Velcro, or other straps, or the device may adhere to the user with an adhesive. Alternatively, the device may be a mobile phone with a specialized application installed or may be configured to connect wirelessly to a cell phone with an application installed.

In certain implementations, the system is able to collect data. In further embodiments, the device may use geometric approximations and/or empirical reference data to determine the force, impulse, or pressure being applied to certain intra-abdominal tissues or organs by the abdomen. These tissues and organs may include the spine, kidneys, liver, bladder, all abdominal blood vessels including the inferior vena cava, and all abdominal nerves including the renal sympathetic nerves. The forces determined might include acceleration forces, which measure walking, running, and other movements that can impact clinical risk. This would allow healthcare professionals to recommend reducing certain physical activities in order to reduce risks to the user. Optionally, a microcontroller could store and transmit the data to the user or to care providers electronically. The device could also be configured to send recommendations to the user or doctor to test blood pressure, urine protein, or other markers of preeclampsia.

The device could be calibrated either automatically, by recognizing certain characteristic position or movement data, or manually, ensuring optimal data collection.

Various implementations comprise a variety of different sensors for detecting physiological parameters, including those relating to orientation, blood flow, sleep patterns, and psychological condition. The device may include one or more sensors which determine the spatial orientation of the user's abdomen relative to the direction of Earth's gravity and a microcontroller that receives and stores orientation data from the sensors and uses the data to estimate the level of clinical risk over various time scales. Optionally, the sensor data comprises a recline angle $\theta$ and a side tilt angle $\varphi$. The orientation risk values may be a function of the recline angle and the sideways tilt angle.

In further embodiments, the device may include a variety of sensors and accelerometers, which may be capable of monitoring the orientation of abdominal soft tissue, various areas of the torso, or fetal heart rate.

In other embodiments, sensors could be used to monitor blood pressure. In one embodiment, the blood pressure monitor uses pulse wave transit time to estimate absolute blood pressure or blood pressure changes. The chest strap of the device may include two electrodes, one on the left and one on the right side of the chest. The electrodes may transmit a current through the chest and measure impedance. The device may simultaneously measure the user's pulse via pulse oximetry. The device may then combine the ECG data and finger pulse rate to calculate pulse wave transit time which may be used to estimate blood pressure. The pulse oximetry could be performed by the camera or light sensor on a mobile phone or other mobile device that is wirelessly connected to the device.

In further embodiments the system may include a blood-oxygen level sensor for generating blood-oxygen level data of the user. The blood oxygen level sensor may be coupled with the processor. The processor may raise or lower the first threshold in response to the blood-oxygen level data from the blood oxygen level sensor.

In various implementations, the physiological parameters recorded by the sensors can include abdominal/body orientation, snoring, blood oxygen, blood pressure, location of center of gravity, activities like running, walking, driving, sleeping, body heat, altitude tracking, pressure readings, temperature readings, and/or user pedometer readings, breathing during sleep, fetal activity monitoring (fetal kicks), fetal heart rate monitoring, uterine contraction monitoring, and fetal ECG monitoring, respiration characteristics, tension, temperature (measured at any variety of locations on or in the body), and/or hemodynamic flow restriction. In various implementations, the system is configured to establish various risk thresholds, which can be based on one or more of these physiological parameters.

Importantly, in certain implementations a "physiological parameter" can include various psychological states. While psychology can be considered as an alternative to physiology in certain applications, as used herein the term "physiological parameter" is meant to encompass certain psychological states, as is discussed further herein.

In various implementations, the device and system provides feedback to the user. In some embodiments, the device may provide vibrational, visual, or audio feedback to the user based on past or current orientation of their abdomen. Feedback could be used to give positive reinforcement of a good abdominal position, to suggest a specific position, to give constructive criticism regarding a non-ideal position, or to reinforce compliance for bed rest. Additionally, the device could be configured to provide feedback only during certain times during the day.

In certain implementations, the device and system performs various functions by way of a system of electronic computing components. In some embodiments, a processor may identify orientation risk values associated with the estimated orientations of the abdomen to produce a time series of identified orientation risk values. A first cumulative risk value may be calculated and updated by calculating a first moving average for a subset of the time series of identified orientation risk values associated with the estimated orientations of the abdomen. The subset for the first moving average may have a first size. The first size may be at least the last 30 seconds of sensor data. In some embodiments, it may be the last two minutes of sensor data. Thereafter the processor may compare the first cumulative risk value to a first threshold and output a warning when the first cumulative risk value crosses the first threshold. Optionally, an input may be coupled with the processor. The input may be configured to receive a user input of pregnancy factors comprising at least one of a multiple pregnancy of the user, body mass index ("BMI") of the user, prior live births of the user, and preexisting hypertension of the user. The processor may raise or lower the first threshold in response to the user input of pregnancy factors.

The processor may be further configured to calculate and update a second cumulative risk value by calculating a second moving average for a subset of the time series of identified orientation risk values. The subset for the second moving average may include at least the last 5 seconds of sensor data. The processor may compare the second cumulative risk value to a second threshold and output a warning when the second cumulative risk value crosses the second threshold.

In some embodiments, the processor may be further configured to process the sensor data for the applications listed above by calculating and updating a moving average for a subset of the time series associated with that sensor. The processor may be further configured to compare the data collected from the various sensors to a data set communicating the sensor outputs for the ideal person of similar gestational age as the user. For example, the processor could receive force measurements from a sensor, calculate force changes over time using the received force measurements, and determining whether the user is engaged in clinically significant activity based on the calculated force changes and an activity threshold. The processor could then compare the clinically significant activity to the recommended activity level or threshold for a person of the same gestational age.

In some embodiments the system may include an infrared sensor coupled with the processor. The processor may determine device use in response to infrared sensor data.

The processor may be further configured to combine the recorded time series of orientation risk values with the recorded time series of activity risk values to generate a continuous time series of risk values. A cumulative risk may be calculated on a subset of the continuous time series of risk values by calculating a moving average for a subset of the continuous time series of risk values. Thereafter, the processor may be configured to compare the cumulative risk to a cumulative risk threshold value and output a warning when the cumulative risk crosses the cumulative risk threshold value. In additional embodiments, the risk value may be reported to the user without having been compared to a threshold.

Optionally, the processing device, by executing the logic or algorithm, may be further configured to perform additional operations. Examples can include: when the user is determined to be engaged in activity, recording a cumulative time duration of the clinically significant activity by the user over a period of time and comparing the cumulative time duration of the clinically significant activity engaged by the user over the time period to a preferred cumulative activity threshold.

The preferred cumulative activity or condition threshold may be dependent on a pregnancy stage of the user.

The system may further include the sensor. The may be housed in a first housing and the processor may be housed in a second housing separate from the first housing. The sensor may be wirelessly coupled with the processor.

In further embodiments, a method for reducing the risk of preterm birth in women is provided. The method may include receiving sensor data from a sensor coupled with a user and determining whether the user is engaged activity based on the received sensor data. When the user is determined to not be engaged in activity, the method may include monitoring the orientation of the abdomen of the user by processing the sensor data to estimate the orientation of the abdomen of the user and identifying orientation risk values associated with the estimated orientations of the abdomen to produce a time series of identified orientation risk values. Thereafter, the method may include calculating and updating a cumulative risk value by calculating a first moving average for a subset of the time series of identified orientation risk values associated with the estimated orientations of the abdomen and comparing the cumulative risk value to a first threshold and a second threshold. A first warning may be outputted when the cumulative risk value crosses the first threshold and a second warning when the cumulative risk value crosses the second threshold.

The method may further include, when the user is determined to be engaged in clinically significant activity, stopping the producing of the time series of identified orientation risk values and identifying activity risk values associated with the sensor data to produce a time series of identified activity risk values. Calculating and updating the cumulative risk score may be performed by combining the time series of identified activity risk values and previously identified orientation risk values and calculating a moving average for a subset of the combined time series of identified activity risk values and previously identified orientation risk values.

In further embodiments, a wearable device system for reducing the risk of preterm birth in women is provided where the wearable device may include one or more sensors for continuously generating force data indicative of an activity of the user. A processor may be coupled with the one or more sensors and be configured to continuously monitor the activity of the user by processing the force data to identify force changes in the force data to estimate a vigorousness of the activity of the user. The processor may compare the identified force changes to a force change threshold value to determine whether the user is engaged in clinically significant activity. When the user is engaged in clinically significant activity, the processor may be configured to identify activity risk values associated with the identified force changes to produce a time series of identified activity risk values. The processor may also calculate and update a cumulative risk value by calculating a moving average for a subset of the time series of identified activity risk values associated with the identified force changes and compare the cumulative risk value to a threshold. A warning may be outputted when the first cumulative risk value crosses the first threshold.

The force changes may be calculated by identifying a difference between a max force and a minimum force in the force data during a time interval and the processor may produce a time series of calculated force changes. Optionally, the processor identifies clinically significant user activity by: calculating and updating a user activity moving average for a subset of the time series of calculated force changes associated with the user activity and comparing the user activity moving average to an activity threshold to determine whether the user is engaged in clinically significant activity. The processor may further record a cumulative time duration of the clinically significant activity engaged by the user over a period of time.

An input may be provided that is coupled with the processor and configured to receive user input of a gestational age of a pregnancy of the user. The processor may be further configured to compare the cumulative time duration of clinically significant activity engaged by the user over the period of time to a preferred cumulative activity threshold specific for the gestational age of the pregnancy of the user.

In one embodiment, the device is used to train the user which orientations and activities are preferable so that the device does not need to be worn through the entire course of pregnancy. The device may be used initially for a few hours or days or may be used periodically throughout pregnancy to refresh the user's memory as to which activities and orientations are preferred. The reminders can come in the form of alerts, text messages, alarms, or any other known form of reminder to the user. In a further embodiment, the training device comprises an app on a mobile device which is attached to the user's torso.

In further embodiments, a device may be provided for inhibiting preeclampsia of a woman. The device may include a sensor configured to generating orientation data and a support configured to couple the sensor to an abdomen of the woman such that the orientation data is indicative of an orientation of the abdomen. A processor may be coupled to the sensor so that it receives the orientation data. The processor may be configured to calculate a time series of values in response to the data and a cumulative risk value in response to the calculated values. The processor may have an output for transmitting a warning in response to the risk value such that preeclampsia risk is mitigated.

Exemplary implementations of the system relate to monitoring abdominal hemodynamics and preventing inferior vena cava ("IVC") compression. Placental health is vital to a healthy full-term pregnancy; however, there is growing evidence that regular compression of the IVC by the gravid uterus causes periods of significant placental and fetal hypoxia. These events slowly contribute to pathologic compensatory reactions by the body, including inflammation of the vasculature of the placenta, which accelerate the onset of hypertension and preeclampsia and also increase the prevalence of gestational diabetes, IUGR, and stillbirth. Some embodiments prevent fetal hypoxia by limiting the amount of time that blood flow is restricted to the placenta and fetus. Since fetal hypoxia results in children with decreased IQ and increased likelihood of learning disabilities, some embodiments could improve cognitive abilities of children.

Some obstetricians incorrectly believe that the supine position must not be unhealthy or it would have been selected out in evolutionary processes, or that a woman's body will "tell her" if she needs to move. There are a number of reasons why these arguments are specious. First, there is the direct evidence that supine sleep results in higher rates of IUGR and stillbirth. Secondly, in 2015, 303,000 women died as a direct result of pregnancy or childbirth, and 99% of these were in the developing world. Clearly even 1000s of years of human evolution are unable to perfect pregnancy without modern medical interventions. Pregnancy is a very delicate balance between the needs of the mother and the incredible oxygen and nutrient requirements of the developing placenta and fetus. Occluding abdominal blood flow for significant periods of time each day or night can absolutely tip the balance and lead to downstream complications. Not surprisingly, uterine artery blood flow drops an average of 34% in pregnant women when in the supine position. Also, not all women feel a natural compulsion to change body orientations when flow is occluded in their IVC, especially when they are deep in sleep.

In various embodiments, the system uses sensors to determine body orientation and blood oxygen levels. It then approximates the degree of venous compression occurring and generates vibrational alerts to the user when she may benefit from changing positions or activities. During the night, it delivers low level vibrations that do not wake users but subconsciously encourages them to shift positions. The device captures sensor data as well as user reactions to the alerts which can be reviewed by the user's obstetrician. In addition, the device can be used with the alerts turned off entirely, and instead, just provide users with a summary of their sleep behavior the next morning. This education alone is very important as body sleep orientation often dramatically changes over the course of pregnancy and studies show that over 60% of all pregnant women that sleep on their backs for significant periods of time each night don't realize that they do so. The device can also use specific user characteristics (eg BMI, singlet or twins, chronic hypertension, diagnostic blood tests, etc.) as well as gestational age to adjust risk threshold levels used in generating alerts.

Exemplary implementations of the system relate to diagnosing and preventing Sleep Disordered Breathing ("SDB"). Sleep disordered breathing is another major impediment to healthy placental growth. Sleep apnea and heavy snoring have both been shown to dramatically lower systemic blood oxygen concentrations in pregnant and non-pregnant individuals. Sleep disordered breathing is a known contributor to hypertension in the general population, so it is not surprising that numerous studies have shown that snoring and sleep apnea increase the risk of preeclampsia, gestational diabetes, and premature birth One of the greatest challenges in identifying SDB in pregnancy is its dynamic nature. Prevalence of snoring and sleep apnea during pregnancy increase by 200-300% compared to pre-pregnancy levels. By definition, the sleep breathing pathology in most pregnant women does not exist at all in early pregnancy, but it does exist, often in severe forms, in late pregnancy. As such, there is no way to know exactly when it becomes a clinically relevant issue. Standard single night sleep monitors frequently miss SDB pathology entirely simply because of the variability in SDB over the course of pregnancy. These monitors cannot be worn night after night simply because they are so uncomfortable and complicated. The monitoring system, however, is practically invisible to the user yet is able to assess the daily or weekly progression of SDB to more accurately determine which women are at serious risk and may need further therapies such as a CPAP device. In addition, since the monitoring system trains women to avoid the supine position, it can eliminate the roughly half of all cases of SDB that are positional related.

Some existing home-use wearable pregnancy devices monitor metrics such as fetal heart rate and uterine contractions. Although these data may improve resultant care in a small number of cases, they typically result in urgent reactionary medicine in the last month of gestation, and frequently generate false positive alerts. In contrast, the present system was developed on the premise that there are a large number of user physiologies and behaviors that have profound impacts on pregnancy outcomes that can be monitored and improved throughout pregnancy.

Of particular interest to us are the many complications of pregnancy which cannot simply be fixed once they manifest. Despite decades of research into the etiology of preeclampsia, its exact pathogenesis remains uncertain; however, it is becoming increasingly apparent that preeclampsia is directly related to underlying placental pathology and dysfunction that develop over many months. Therefore, it inherently is not a disease that can be fixed at the end of pregnancy, it is one that must be prevented.

As most cases of preeclampsia occur at the end of pregnancy, the best way to prevent the majority of cases is to delay onset of dangerously high blood pressure until the pregnancy is full-term. The presently disclosed system tracks the adjustable factors in pregnancy that can, prevent diseases and negative conditions. By way of example, these adjustable factors include the following. Sleep disordered breathing leads to hypertension in both pregnant and non-pregnant individuals. Similarly, snoring and sleep apnea are highly correlated to hypertensive diseases of pregnancy such as preeclampsia, as well as gestational diabetes and premature birth. Uterine artery blood flow and fetal oxygenation are both shown to significantly decrease in the supine position. Numerous studies have now shown that women who spend significant time in reclined and supine positions have much higher rates of stillbirth and intrauterine growth restriction. Depression and stress double the risk of preterm birth even after covariants such as low economic status and drug use are excluded. This is not surprising as depression is known to cause hypertension and increase placental and fetal cortisol levels.

The placenta serves as the lungs, kidneys, liver, endocrine system, and immune defense of the fetus. Despite its enormous importance, the placenta is arguably the least understood of all human organs. This is partly because the development of the human placenta cannot be invasively studied because it only exists during pregnancy at which time it is performing life-maintaining duties for the fetus. Not surprisingly, as we learn more about this mysterious organ, we also learn of its great importance in protecting the fetus from potential hazards during the pregnancy.

Exemplary implementations of the system relate to monitoring abdominal hemodynamics and preventing inferior vena cava ("IVC") compression. Placental health is vital to a healthy full-term pregnancy; however, there is growing evidence that regular compression of the inferior vena cava (IVC) by the gravid uterus causes periods of significant placental and fetal hypoxia. These events slowly contribute to pathologic compensatory reactions by the body, including inflammation of the vasculature of the placenta, which accelerate the onset of hypertension and preeclampsia and also increase the prevalence of gestational diabetes, IUGR, and stillbirth.

Some obstetricians incorrectly believe that the supine position must not be unhealthy or it would have been selected out in evolutionary processes, or that a woman's body will "tell her" if she needs to move. There are a number of reasons why these arguments are specious. First, there is the direct evidence that supine sleep results in higher rates of IUGR and stillbirth. Secondly, in 2015, 303,000 women died as a direct result of pregnancy or childbirth, and 99% of these were in the developing world. Clearly even 1000s of years of human evolution are unable to perfect pregnancy without modern medical interventions. Pregnancy is a very delicate balance between the needs of the mother and the incredible oxygen and nutrient requirements of the developing placenta and fetus. Occluding abdominal blood flow for significant periods of time each day or night can absolutely tip the balance and lead to downstream complications. Not surprisingly, uterine artery blood flow drops an average of 34% in pregnant women when in the supine position. Also, not all women feel a natural compulsion to change body orientations when flow is occluded in their IVC, especially when they are deep in sleep.

In various embodiments, the system uses sensors to determine body orientation and blood oxygen levels. It then approximates the degree of venous compression occurring and generates vibrational alerts to the user when she may benefit from changing positions or activities. During the night, it delivers low level vibrations that do not wake users but subconsciously encourages them to shift positions. The device captures sensor data as well as user reactions to the alerts which can be reviewed by the user's obstetrician. In addition, the device can be used with the alerts turned off entirely, and instead, just provide users with a summary of their sleep behavior the next morning. This education alone is very important as body sleep orientation often dramatically changes over the course of pregnancy and studies show that over 60% of all pregnant women that sleep on their backs for significant periods of time each night don't realize that they do so. The device can also use specific user characteristics (e.g. BMI, singlet or twins, chronic hypertension, diagnostic blood tests, etc.) as well as gestational age to adjust risk threshold levels used in generating alerts.

Exemplary implementations of the system relate to diagnosing and preventing Sleep Disordered Breathing ("SDB"). Sleep disordered breathing is another major impediment to healthy placental growth. Sleep apnea and heavy snoring have both been shown to dramatically lower systemic blood oxygen concentrations in pregnant and non-pregnant individuals. Sleep disordered breathing is a known contributor to hypertension in the general population, so it is not surprising that numerous studies have shown that snoring and sleep apnea increase the risk of preeclampsia, gestational diabetes, and premature birth.

One of the greatest challenges in identifying SDB in pregnancy is its dynamic nature. Prevalence of snoring and sleep apnea during pregnancy increase by 200-300% compared to pre-pregnancy levels. By definition, the sleep breathing pathology in most pregnant women does not exist at all in early pregnancy, but it does exist, often in severe forms, in late pregnancy. As such, there is no way to know exactly when it becomes a clinically relevant issue. Standard single night sleep monitors frequently miss SDB pathology entirely simply because of the variability in SDB over the course of pregnancy. These monitors cannot be worn night after night simply because they are so uncomfortable and complicated. The Monitoring system, however, is practically invisible to the user yet is able to assess the daily or weekly progression of SDB to more accurately determine which women are at serious risk and may need further therapies such as a CPAP device. In addition, since the monitoring system trains women to avoid the supine position, it can eliminate the roughly half of all cases of SDB that are positional related.

In one embodiment, the system is a health monitoring system with one or more sensors for generating sensor data, configured to identify health risk values associated with the sensor data; assign the risk value to a corresponding time value; and output a warning when the risk value persists for the direction of the time value.

In one embodiment, the system is a health monitoring system with one or more sensors for generating sensor data, configured to identify health risk values associated with the sensor data; assign the risk value to a corresponding time value; adjust the time values continuously based on new risk values; and output a warning when the risk value persists for the direction of the time value.

An example of this approach is the following: every body orientation has a set amount of time in which the user is allowed to be before an alert is issued. In one embodiment, every single unique combination of side tilt and recline angles has a different total amount of time associated with it. In one embodiment, a recline angle of −90 degrees with 0 degrees side tilt (flat on back) has the very lowest amount of time allowed (2 minutes). A combination of recline angle −75 degrees and side tilt 7 degrees has a maximum time of 4 minutes and 22 seconds. A combination of −35 recline and −82 side tilt has no maximum time value (infinity) because it is considered completely safe. Every time the user moves orientations, the algorithm instantly calculates how much time the user has left in that position. The remaining time is transferred and prorated to the new position. So, if the user has been flat on her back for 1 of the maximum 2 minutes allowed by the algorithm and then shifts to recline −75 and side tilt 7, she will have 50% of the time left for the new position (2 min and 11 seconds).

In various embodiments, the system defines zones and assigns risk scores based on the user's presence in those zones compared with defined thresholds. In various embodiments, these zones can represent various orientations, positions and the like, as related to the physiological parameters discussed elsewhere herein.

In another embodiment, the risk and time values are based on continuous equations so there are an infinite number of risk and time levels. In one embodiment, different risk equations are used to cover different quadrants of space.

In another embodiment, more than 1 real time risk variable is used in the risk calculation equation. In one embodiment, the overall risk is a direct function of both body orientation and snoring so that the alert is more likely to go off when the user has high risk values for each of body orientation and snoring.

While some embodiments are generally discussed in terms of monitoring orientation and activity of pregnant women, many methods, devices, and systems may be applied to any other area of the body where different positions have different levels of risk or benefit associated with them. For example, users with obesity related hypertension may benefit from preventing abdominal fat from chronically or periodically compressing renal nerves and abdominal veins which may increase hypertension. In another example, in a user with back pain, the algorithm assigns different levels of risk or detriment to different positions. The cumulative negative impact over time that the user experiences while in various positions is added up and compared to allowable risk-time levels to determine whether the user should be alerted to change position in order to prevent back pain or muscle or nerve inflammation. Devices and methods may be beneficial to users suffering from gastroesophaael reflux or other digestive disorder that require they spend time in certain positions. Other diseases that may benefit from embodiments disclosed herein include Chorea, Parkinson's, and heart disease.

In one embodiment, an obese man may benefit from the positional functionality of devices and systems described in this patent application. While sleeping, the device may issue vibrational alerts to the man when he has been deemed to have been in one or more risky positions for too long. In one embodiment, he has hypoventilation syndrome and the mass of his abdomen makes it more difficult to breathe at night when in the supine position.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

In some embodiments, temperature of the user is measured in order to determine the ideal fertility window for conception. In further embodiments, an algorithm estimates how much the core temperature of the user has risen due to exercise or general activity. In some embodiments, the algorithm gets smarter over time by calibrating vigorousness of activity with temperature rise. In some embodiments, the temperature is measured directly by the device using sensors. In some embodiments, these sensors are on the skin, under the armpit, in the ear, intravaginal, or other places of the body known to provide consistent temperature measurements. In some embodiments, a temperature sensor worn on the outside of the body measures ambient air temperature and another sensor on the skin measures skin temperature. Further, in some embodiments, an algorithm account for the cooling or warming effect the environment has on skin temperature in order to estimate a more accurate body temperature.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like. Different arrangements of the components depicted in the drawings or described above, as well as components and steps not shown or described are possible. Similarly, some features and sub-combinations are useful and may be employed without reference to other features and sub-combinations. Embodiments of the system have been described for illustrative and not restrictive purposes, and alternative embodiments will become apparent to readers of this patent. Accordingly, the various implementations of system are not limited to the embodiments described above or depicted in the drawings, and various embodiments and modifications may be made without departing from the scope of the claims below.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system for monitoring body orientation; where different levels of risk are assigned to specific discrete ranges of body orientations. Other embodiments of this aspect include corresponding computer systems, apparatus, and computer programs recorded on one or more computer storage devices, each configured to perform the actions of the methods.

One general aspect includes a system for monitoring body orientation; where different levels of risk are assigned to specific discrete ranges of body orientations; where a user is allocated a maximum amount of time in any given orientation range before the user is prompted to move into a less risky orientation. Other embodiments of this aspect include corresponding computer systems, apparatus, and computer programs recorded on one or more computer storage devices, each configured to perform the actions of the methods.

One general aspect includes the system where a subset of body orientation ranges which are not risky have no maximum time limit. Other embodiments of this aspect include corresponding computer systems, apparatus, and computer programs recorded on one or more computer storage devices, each configured to perform the actions of the methods.

One general aspect includes the system in previous claims, where the maximum time allowed in a given range is affected by the duration of time spent previously in other ranges. Other embodiments of this aspect include corresponding computer systems, apparatus, and computer programs recorded on one or more computer storage devices, each configured to perform the actions of the methods.

One general aspect includes a system that includes a virtual model of the abdomen to calculate risk levels associated with different body orientations. The system also includes the system of the previous claim, where the abdominal model estimates hemodynamic characteristics of one or more arteries and veins of the uterus, kidneys, legs, liver, placenta, and fetus. Other embodiments of this aspect include corresponding computer systems, apparatus, and computer programs recorded on one or more computer storage devices, each configured to perform the actions of the methods.

One general aspect includes a system for predicting or diagnosing preeclampsia, including: one or more acoustic sensors, and a processor configured to analyze sensor data. Other embodiments of this aspect include corresponding computer systems, apparatus, and computer programs recorded on one or more computer storage devices, each configured to perform the actions of the methods.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. In one Example, A system for reducing fetal risk in a user, including: a wearable device; a memory unit; at least one sensor configured to monitor the user for at least one physiological parameter and generate sensor data; and a processor coupled to the at least one sensor and configured to: monitor fetal risk by processing sensor data to identify risk values associated with the at least one physiological parameter to produce a time series of identified fetal risk values; and calculate and update a first cumulative risk value by calculating a first moving average for a subset of the time series of identified fetal risk values. Other embodiments of this aspect include corresponding computer systems, apparatus, and computer programs recorded on one or more computer storage devices, each configured to perform the actions of the methods.

Implementations may include one or more of the following features. The system where the processor is configured to compare the at least one cumulative risk value to a risk threshold. The system where the device is configured to output a warning when the first cumulative risk value exceeds the first threshold. The system further including a database in communication with the processor, where: the database includes at least one adapting risk threshold and is configured to adapt the at least one adapting risk threshold based on the recorded time series of identified fetal risk values, and the processor is configured to compare the at least one cumulative risk value to the at least one adapting risk threshold. The system where at least one sensor is a non-orientation sensor configured to monitor a non-orientation physiological parameter and the processor is configured to assign at least one non-orientation fetal risk value. The system where the at least one sensor is selected from the group including: an acoustic sensor, a blood oxygen sensor, a photo diode, an accelerometer, an orientation sensor, a pressure sensor, and an ultra wide band sensor. The system where the physiological parameter is selected from the group including: blood oxygen concentration, heart rate, sleep position, sleep quality, respiration characteristics, snoring, sleep apnea, hypoventilation, and/or hyperventilation and combinations thereof. The system further including a garment configured to house the device and retain a fixed orientation relative to the user. The system where the garment is selected from the group including a shirt and an undergarment. The system further including at least one magnet configured to promote device orientation. The system further including a clip configured to promote device orientation. The system where the at least one sensor is selected from the group including an acoustic sensor, an accelerometer, an ultra wide band sensor, a blood oxygen sensor and a photo sensor. The system where the system is configured to alert the user when the identified fetal risk values exceed an established risk threshold. The system further including an external sensor disposed outside the housing. The system further including at least one fixed orientation promoter. The system where the fixed orientation promoter is selected from the group including a garment, a magnet and a clip. The device further including a garment selected from the group including: a shirt, a belt, or underpants. The system further including an alert system. The system where the processor is configured to generate and compare at least one cumulative risk value from the fetal risk scores for comparison to a risk threshold. The health monitoring and improvement system where the health monitoring and improvement system is used to monitor and improve the health of the user during pregnancy. The health monitoring and improvement system where the health monitoring and improvement system is used to monitor and improve the health of a fetus during the pregnancy term. The health monitoring and improvement system where the health monitoring and improvement system is used to monitor and improve the health of obese or other clinically high risk individuals. The data collection system where the data collection system is included of one or more sensors. The data collection system where the data collection system is included of one or more sensors selected from the group including: accelerometers, gyroscopes, magnetometers, infrared, temperature, pressure, microphone, oximeters, ultra wide band microwave, and radio. The data collection system where one or more sensors are single axis sensors. The data collection system where one or more sensors are 3-axis sensors. The data collection system where the sensors are user-programmable. The data collection system where the data collection system contains analog-to-digital converters for digitizing the output from one or more sensors. The data collection system where the data collection system collects data regarding physiological parameters specific to the user. The data collection system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The data collection system where the physiological parameters include psychological states. The data collection system where the data collection system uses empirical reference data to determine force, impulse, or pressure applied to intra-abdominal tissues or organs. The data collection system where the tissues and organs are selected from the group including: spine, kidneys, liver, bladder, all abdominal blood vessels including the inferior vena cava, and all abdominal nerves. The device where the device further includes: a PCB; a battery; and a vibrational motor. The device where the device is affixed to the body using adhesives. The device where the device is affixed to the garment using magnets. The device where the device is affixed to the body using straps. The device where the device is affixed to the body using magnets. The processing system where the manual inputs are selected from the group including: number of pregnancies of the user, body mass index, prior live births, preexisting hypertension. The processing system where the processor may raise or lower the threshold in response to the manual input selections. The processing system where the processing system is configured to compare physiological parameters to the physiological parameters of an ideal user. The processing system where the processor is configured to identify clinically significant physiological parameter values. The processing system where the processing system is configured to communicate with an external device. The processing system where the physiological parameters also include psychological states. The processing system where the external device is selected from the group including: cellular, hand-held, or desktop. The processing system where the processing system is configured to communicate outputs to the user or the user's care specialist. The processing system where the processing system is configured to recognize appropriate time spans for data processing. The device where the device is fixed internally in the body The device where the device is attached to the user in a manner that prevents rotation. The processing system where the processing system identifies risk values associated with one or more physiological parameters. The processing system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The processing system where the processing system determines risk values by creating a moving average of the physiological parameter data and comparing it to a threshold. The processing system where the moving average calculated over any of a variety of time spans. The processing system where there is a minimum and maximum threshold limitation. The processing system where the processor is coupled with manual inputs. The feedback system where the feedback system informs the user when a risk value exceeds the threshold value for a physiological parameter. The feedback system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The feedback system where the physiological parameters also include psychological states. The feedback system where the feedback is selected from the group including light indicators, display schemes, audio, vibrational. The feedback system where the feedback system informs the user when a physiological parameter is inside the minimum and maximum threshold values. The feedback system where the feedback system informs the user when the time average of a physiological parameter is exceeds the threshold values. Implementations of the described techniques may include hardware, a method or process, or computer software on a computer-accessible medium.

In one Example, A system for reducing fetal risk in a user, including: a fetal risk device including a housing; a transmission component disposed in the housing; at least one sensor disposed within the housing for monitoring a physiological parameter and generating parameter data; a processor configured to assign fetal risk values from the parameter data to produce a time series of identified fetal risk values; and an alert system configured to notify the user of identified risk values. Other embodiments of this aspect include corresponding computer systems, apparatus, and computer programs recorded on one or more computer storage devices, each configured to perform the actions of the methods.

Implementations may include one or more of the following features. The system where the at least one sensor is selected from the group including an acoustic sensor, an accelerometer, an ultra wide band sensor, a blood oxygen sensor and a photo sensor. The system where the system is configured to alert the user when the identified fetal risk values exceed an established risk threshold. The system further including an external sensor disposed outside the housing. The system further including at least one fixed orientation promoter. The system where the fixed orientation promoter is selected from the group including a garment, a magnet and a clip. The device further including a garment selected from the group including: a shirt, a belt, or underpants. The system further including an alert system. The system where the processor is configured to generate and compare at least one cumulative risk value from the fetal risk scores for comparison to a risk threshold. The health monitoring and improvement system where the health monitoring and improvement system is used to monitor and improve the health of the user during pregnancy. The health monitoring and improvement system where the health monitoring and improvement system is used to monitor and improve the health of a fetus during the pregnancy term. The health monitoring and improvement system where the health monitoring and improvement system is used to monitor and improve the health of obese or other clinically high risk individuals. The data collection system where the data collection system is included of one or more sensors. The data collection system where the data collection system is included of one or more sensors selected from the group including: accelerometers, gyroscopes, magnetometers, infrared, temperature, pressure, microphone, oximeters, ultra wide band microwave, and radio. The data collection system where one or more sensors are single axis sensors. The data collection system where one or more sensors are 3-axis sensors. The data collection system where the sensors are user-programmable. The data collection system where the data collection system contains analog-to-digital converters for digitizing the output from one or more sensors. The data collection system where the data collection system collects data regarding physiological parameters specific to the user. The data collection system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The data collection system where the physiological parameters include psychological states. The data collection system where the data collection system uses empirical reference data to determine force, impulse, or pressure applied to intra-abdominal tissues or organs. The data collection system where the tissues and organs are selected from the group including: spine, kidneys, liver, bladder, all abdominal blood vessels including the inferior vena cava, and all abdominal nerves. The device where the device further includes: a PCB; a battery; and a vibrational motor. The device where the device is affixed to the body using adhesives. The device where the device is affixed to the garment using magnets. The device where the device is affixed to the body using straps. The device where the device is affixed to the body using magnets. The processing system where the manual inputs are selected from the group including: number of pregnancies of the user, body mass index, prior live births, preexisting hypertension. The processing system where the processor may raise or lower the threshold in response to the manual input selections. The processing system where the processing system is configured to compare physiological parameters to the physiological parameters of an ideal user. The processing system where the processor is configured to identify clinically significant physiological parameter values. The processing system where the processing system is configured to communicate with an external device. The processing system where the physiological parameters also include psychological states. The processing system where the external device is selected from the group including: cellular, hand-held, or desktop. The processing system where the processing system is configured to communicate outputs to the user or the user's care specialist. The processing system where the processing system is configured to recognize appropriate time spans for data processing. The device where the device is fixed internally in the body The device where the device is attached to the user in a manner that prevents rotation. The processing system where the processing system identifies risk values associated with one or more physiological parameters. The processing system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The processing system where the processing system determines risk values by creating a moving average of the physiological parameter data and comparing it to a threshold. The processing system where the moving average calculated over any of a variety of time spans. The processing system where there is a minimum and maximum threshold limitation. The processing system where the processor is coupled with manual inputs. The feedback system where the feedback system informs the user when a risk value exceeds the threshold value for a physiological parameter. The feedback system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The feedback system where the physiological parameters also include psychological states. The feedback system where the feedback is selected from the group including light indicators, display schemes, audio, vibrational. The feedback system where the feedback system informs the user when a physiological parameter is inside the minimum and maximum threshold values. The feedback system where the feedback system informs the user when the time average of a physiological parameter is exceeds the threshold values. Implementations of the described techniques may include hardware, a method or process, or computer software on a computer-accessible medium.

In one Example, A system for reducing fetal risk in a user, including: a wearable device housing including a housing, a memory unit and a transmission unit; at least one sensor disposed within the housing and configured to generate fetal risk data relating to physiological parameters; and a processor coupled to the sensor so as to receive the fetal risk data, where the processor is configured to calculate and produce a time-series of fetal risk scores in response to the fetal risk data, and where the fetal risk scores can be wirelessly transmitted via the transmission unit. Other embodiments of this aspect include corresponding computer systems, apparatus, and computer programs recorded on one or more computer storage devices, each configured to perform the actions of the methods.

Implementations may include one or more of the following features. The system further including an alert system. The system where the processor is configured to generate and compare at least one cumulative risk value from the fetal risk scores for comparison to a risk threshold. The health monitoring and improvement system where the health monitoring and improvement system is used to monitor and improve the health of the user during pregnancy. The health monitoring and improvement system where the health monitoring and improvement system is used to monitor and improve the health of a fetus during the pregnancy term. The health monitoring and improvement system where the health monitoring and improvement system is used to monitor and improve the health of obese or other clinically high risk individuals. The data collection system where the data collection system is included of one or more sensors. The data collection system where the data collection system is included of one or more sensors selected from the group including: accelerometers, gyroscopes, magnetometers, infrared, temperature, pressure, microphone, oximeters, ultra wide band microwave, and radio. The data collection system where one or more sensors are single axis sensors. The data collection system where one or more sensors are 3-axis sensors. The data collection system where the sensors are user-programmable. The data collection system where the data collection system contains analog-to-digital converters for digitizing the output from one or more sensors. The data collection system where the data collection system collects data regarding physiological parameters specific to the user. The data collection system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The data collection system where the physiological parameters include psychological states. The data collection system where the data collection system uses empirical reference data to determine force, impulse, or pressure applied to intra-abdomical tissues or organs. The data collection system where the tissues and organs are selected from the group including: spine, kidneys, liver, bladder, all abdominal blood vessels including the inferior vena cava, and all abdominal nerves. The device where the device further includes: a PCB; a battery; and a vibrational motor. The device where the device is affixed to the body using adhesives. The device where the device is affixed to the garment using magnets. The device where the device is affixed to the body using straps. The device where the device is affixed to the body using magnets. The processing system where the manual inputs are selected from the group including: number of pregnancies of the user, body mass index, prior live births, preexisting hypertension. The processing system where the processor may raise or lower the threshold in response to the manual input selections. The processing system where the processing system is configured to compare physiological parameters to the physiological parameters of an ideal user. The processing system where the processor is configured to identify clinically significant physiological parameter values. The processing system where the processing system is configured to communicate with an external device. The processing system where the physiological parameters also include psychological states. The processing system where the external device is selected from the group including: cellular, hand-held, or desktop. The processing system where the processing system is configured to communicate outputs to the user or the user's care specialist. The processing system where the processing system is configured to recognize appropriate time spans for data processing. The device where the device is fixed internally in the body The device where the device is attached to the user in a manner that prevents rotation. The processing system where the processing system identifies risk values associated with one or more physiological parameters. The processing system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The processing system where the processing system determines risk values by creating a moving average of the physiological parameter data and comparing it to a threshold. The processing system where the moving average calculated over any of a variety of time spans. The processing system where there is a minimum and maximum threshold limitation. The processing system where the processor is coupled with manual inputs. The feedback system where the feedback system informs the user when a risk value exceeds the threshold value for a physiological parameter. The feedback system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The feedback system where the physiological parameters also include psychological states. The feedback system where the feedback is selected from the group including light indicators, display schemes, audio, vibrational. The feedback system where the feedback system informs the user when a physiological parameter is inside the minimum and maximum threshold values. The feedback system where the feedback system informs the user when the time average of a physiological parameter is exceeds the threshold values. Implementations of the described techniques may include hardware, a method or process, or computer software on a computer-accessible medium.

In one Example, A health monitoring and improvement system, including: a device; a data collection system; a processor, where the processing system collects sensor data from the device; and a feedback system. Other embodiments of this aspect include corresponding computer systems, apparatus, and computer programs recorded on one or more computer storage devices, each configured to perform the actions of the methods.

Implementations may include one or more of the following features. The health monitoring and improvement system where the health monitoring and improvement system is used to monitor and improve the health of the user during pregnancy. The health monitoring and improvement system where the health monitoring and improvement system is used to monitor and improve the health of a fetus during the pregnancy term. The health monitoring and improvement system where the health monitoring and improvement system is used to monitor and improve the health of obese or other clinically high risk individuals. The data collection system where the data collection system is included of one or more sensors. The data collection system where the data collection system is included of one or more sensors selected from the group including: accelerometers, gyroscopes, magnetometers, infrared, temperature, pressure, microphone, oximeters, ultra wide band microwave, and radio. The data collection system where one or more sensors are single axis sensors. The data collection system where one or more sensors are 3-axis sensors. The data collection system where the sensors are user-programmable. The data collection system where the data collection system contains analog-to-digital converters for digitizing the output from one or more sensors. The data collection system where the data collection system collects data regarding physiological parameters specific to the user. The data collection system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The data collection system where the physiological parameters include psychological states. The data collection system where the data collection system uses empirical reference data to determine force, impulse, or pressure applied to intra-abdomical tissues or organs. The data collection system where the tissues and organs are selected from the group including: spine, kidneys, liver, bladder, all abdominal blood vessels including the inferior vena cava, and all abdominal nerves. The device where the device further includes: a PCB; a battery; and a vibrational motor. The device where the device is affixed to the body using adhesives. The device where the device is affixed to the garment using magnets. The device where the device is affixed to the body using straps. The device where the device is affixed to the body using magnets. The processing system where the manual inputs are selected from the group including: number of pregnancies of the user, body mass index, prior live births, preexisting hypertension. The processing system where the processor may raise or lower the threshold in response to the manual input selections. The processing system where the processing system is configured to compare physiological parameters to the physiological parameters of an ideal user. The processing system where the processor is configured to identify clinically significant physiological parameter values. The processing system where the processing system is configured to communicate with an external device. The processing system where the physiological parameters also include psychological states. The processing system where the external device is selected from the group including: cellular, hand-held, or desktop. The processing system where the processing system is configured to communicate outputs to the user or the user's care specialist. The processing system where the processing system is configured to recognize appropriate time spans for data processing. The device where the device is fixed internally in the body The device where the device is attached to the user in a manner that prevents rotation. The processing system where the processing system identifies risk values associated with one or more physiological parameters. The processing system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The processing system where the processing system determines risk values by creating a moving average of the physiological parameter data and comparing it to a threshold. The processing system where the moving average calculated over any of a variety of time spans. The processing system where there is a minimum and maximum threshold limitation. The processing system where the processor is coupled with manual inputs. The feedback system where the feedback system informs the user when a risk value exceeds the threshold value for a physiological parameter. The feedback system where the physiological parameters are selected from the group including: abdominal/body orientation, snoring, blood oxygen, blood pressure, location of center of gravity, physical activity, body heat, altitude tracking, pressure, temperature, respiration, respiration during sleep, fetal activity, fetal heart rate, uterine contraction, fetal ECG, tension, and hemodynamic flow. The feedback system where the physiological parameters also include psychological states. The feedback system where the feedback is selected from the group including light indicators, display schemes, audio, vibrational. The feedback system where the feedback system informs the user when a physiological parameter is inside the minimum and maximum threshold values. The feedback system where the feedback system informs the user when the time average of a physiological parameter is exceeds the threshold values. Implementations of the described techniques may include hardware, a method or process, or computer software on a computer-accessible medium.

In one example, a wearable device system for reducing risks associated with birth, the wearable device comprising one or more sensors for generating sensor data indicative of an orientation of an abdomen of a user, a processor coupled with the one or more sensors, the processor configured to monitor the orientation of the abdomen of the user by processing the sensor data to estimate the orientation of the abdomen of the user, assign a health zone to the orientation, assign total amounts of time allowed for each health zone where zones of healthier orientations allow longer amounts of time and output a warning when the time threshold is exceeded. In some examples, the user can be in one of the zones for any amount of time without an alert being issued. In some examples, there are a minimum of 3 total health zones possible. In some examples, a prorated time calculation is used to determine how much time is carried over to new zones.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 1B is a schematic overview of a network implementation of the system, according to one exemplary embodiment.

FIG. 10A illustrates exemplary orientation risk value matrices.

FIG. 10B illustrates further exemplary orientation risk value matrices.

FIG. 12 shows exemplary risk factors and exemplary risk values for customizing an orientation and/or activity monitoring algorithm according to some embodiments.

FIG. 13 illustrates an exemplary user interface for orientation risk monitoring according to some embodiments.

FIG. 14 illustrates an exemplary user interface for activity risk monitoring.

DETAILED DESCRIPTION

Figure 1A:
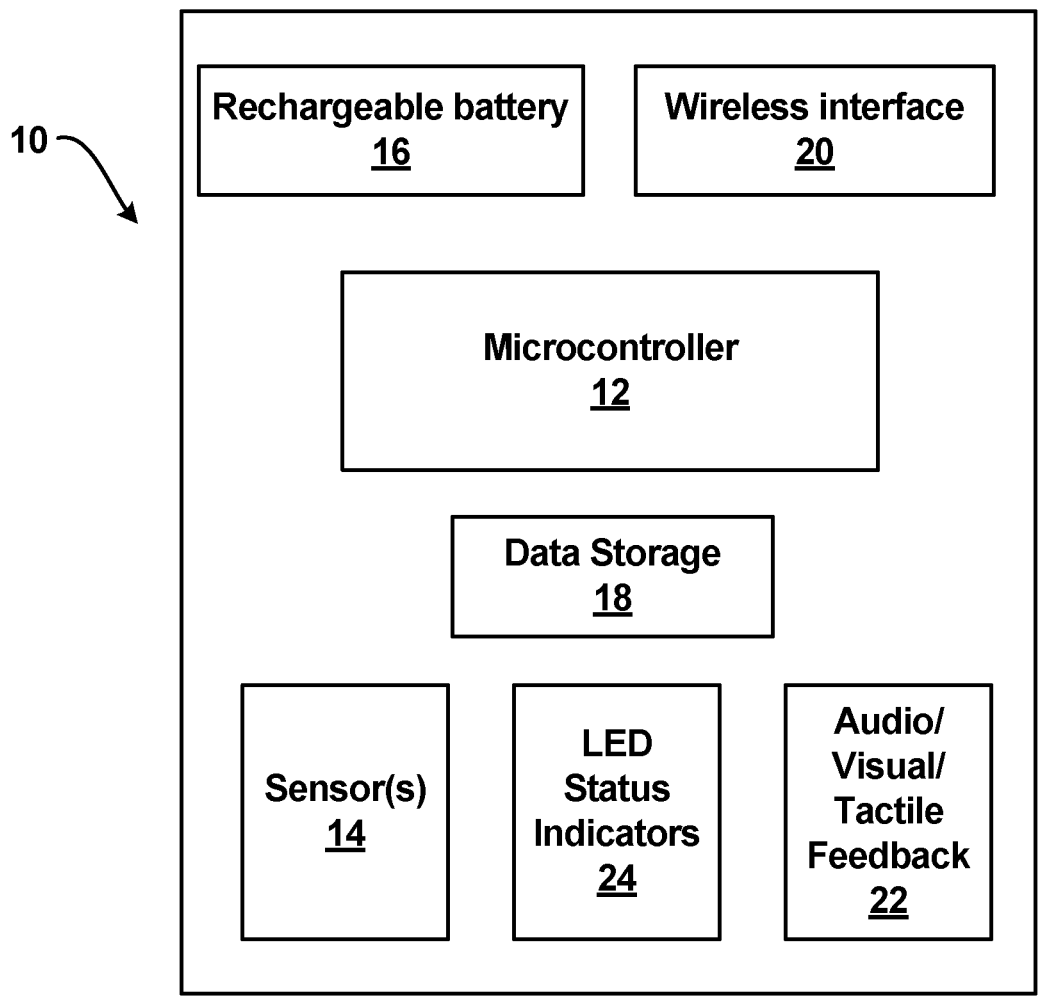
FIG. 1A illustrates a system diagram of an exemplary device for tracking abdominal orientation and/or user activity.

The disclosed devices, systems and methods relate to various systems, devices and methods for health monitoring, particularly in pregnant women. In exemplary implementations, the disclosed implementations relate to preventing and predicting certain diseases and conditions by providing various devices, systems and methods directed at collecting information about the activity of the user, including relating to physiological parameters. The subject matter of embodiments of the present disclosure is described here with specificity, but this description is not necessarily intended to limit the scope of the claims. While the above examples are generally discussed with reference to avoiding preeclampsia and other complications of pregnancy, it should be understood that embodiments disclosed herein may be applicable to preventing other conditions as well, such as pressure on abdominal veins and organs can be harmful outside of pregnancy as well. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

In various embodiments, and as shown in FIG. 1A-7B, various devices and systems are provided which are directed to the use of a device 10. In various implementations, this device 10 can be secured to the user's body via an external mounting device 28, such as by way of a garment 30 or clip, so as to maintain a constant relative orientation. Further, in various implementations, and as shown in FIGS. 8-20, the device 10 readings can be used to assess risk and aid in the prevention and prediction of diseases. Accordingly, systems, devices, and methods to track physiological parameters and provide clinically relevant feedback to the user and/or physician in order to prevent, avoid, or reverse diseases or conditions that are related to abdominal position.

As discussed above in relation to FIG. 1A, in certain implementations, a health monitoring system 1 is provided. In these implementations, the system has a minimum of one of more sensors 14, a processor 12, a memory unit 18, and an alert system or feedback device 22; wherein each of the sensors 14 is configured to detect a predetermined physiological parameter of a person (sensors discussed below). In use, the system may comprise several optional steps used to monitor at least one physiological parameter and assess the associated fetal risk.

In these implementations, the system 1 records a time series of individual parameter values into the memory unit 18. Further, the processor 12 analyzes a predetermined number of the most recently recorded physiological parameters to determine if one or more of the detected parameters is abnormal as determined over a set period of time. When at least one of the physiological parameters is determined to be abnormal, an alert is generated. Further, long-term trends can be analyzed, such that recorded data is aggregated and the user's risk profile is calibrated over time, as would be apparent to a skilled artisan.

Figure 8:
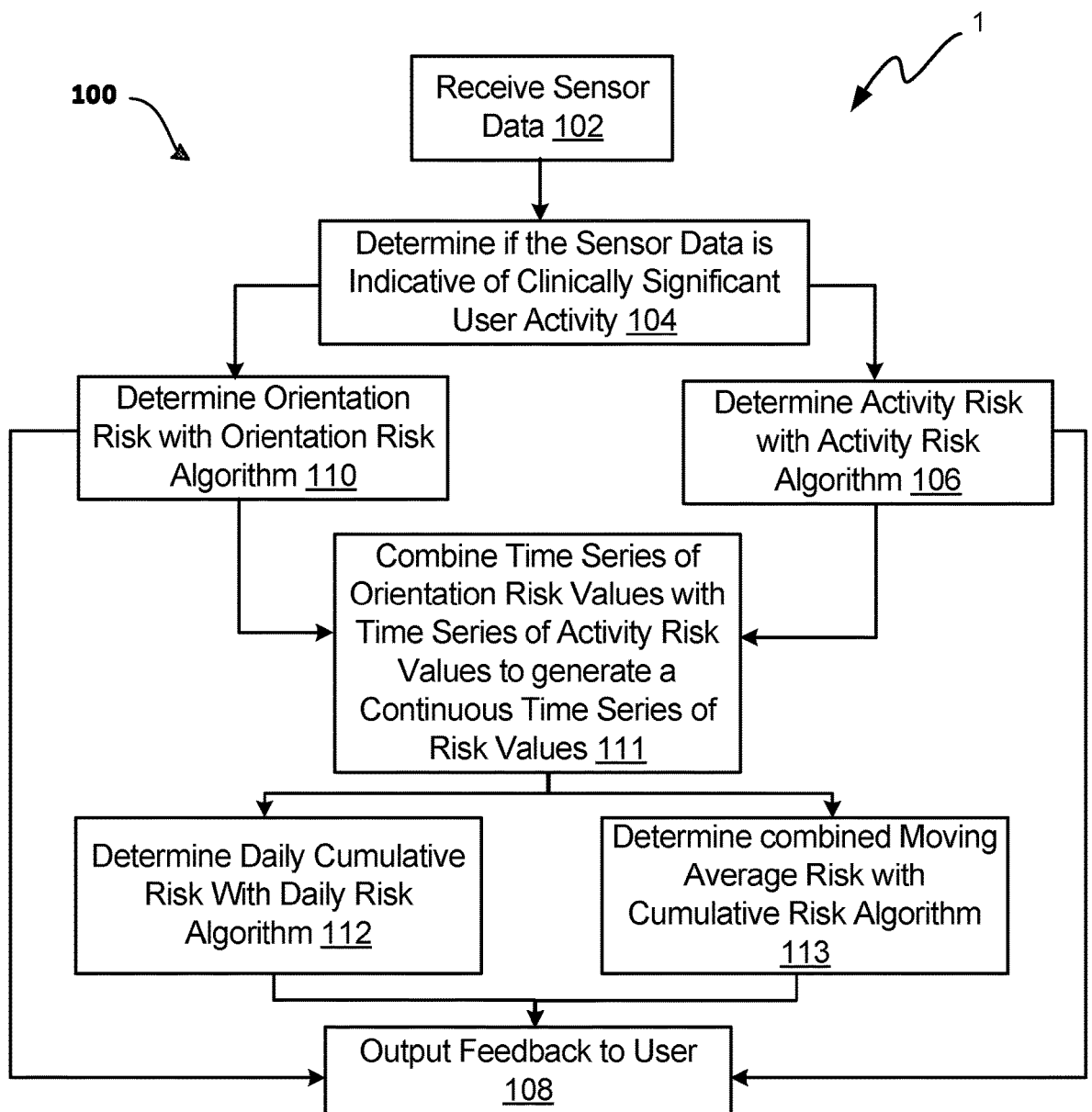
FIG. 8 illustrates an exemplary operational flow according to some embodiments.

FIG. 8 illustrates an exemplary operational flow 100 according to some embodiments of the system 1 device 10. Sensor data may be received 102. From the sensor data, a processor may determine if the sensor data is indicative of significant user activity 104. If the sensor data is indicative of significant user activity, the processor may further analyze the sensor data to monitor user activity and determine activity risk with an activity risk algorithm 106. Based on the monitoring 106, the processor may output feedback to a user 108. When the sensor data is indicative of a user not engaged in significant activity, the processor may analyze the sensor data to monitor user orientation and determine orientation risk with an orientation risk algorithm 110. Based on the monitoring 110, the processor may output feedback to a user 108. Additionally, in some embodiments, the processor may be configured combine a time series of orientation risk values obtained from algorithm 110 and a time series of activity risk values obtained from algorithm 106 to generate a continuous time series of risk values 111. The continuous time series of risk values may then be used to determine a daily cumulative risk 112 over an extended time period (e.g., 24 hours starting and ending each day at 3 a.m.). The daily cumulative risk may be a function of the risk values obtained from the monitoring 106 and/or the monitoring 110. The processor may output feedback 108 per the daily cumulative risk determination 112. Further, in some embodiments, the continuous time series of risk values may be used to calculate a cumulative risk score 113 which may then be compared to a cumulative risk threshold as will be discussed further below.

In certain implementations, the device can be used for two or more of the following purposes: used in pre-pregnancy or early pregnancy as a fitness device, used in mid and late pregnancy to monitor body orientation, sleep, and depression, used in late pregnancy to monitor fetal activity and uterine contractions, used after pregnancy again as a fitness device, and used for monitoring SIDS in the new baby.

These risk scores 113 can be updated as data is collected, as would be apparent to one of skill in the art. Further, the risk score algorithm can be revised as outcomes for additional users are collected, as would be apparent to one of skill in the art. While generally illustrated with orientation monitoring algorithms, activity monitoring algorithms, daily risk algorithms, and cumulative risk algorithms, it should be understood that embodiments may have one, some, or all of the functionality described above. Many embodiments may implement all of the functions, but other embodiments may be configured to only monitor user activity risk or only monitor orientation risks or other sub combinations of functions.

FIG. 1A illustrates an exemplary device 10 according to some embodiments of the system 1. The device 10 may include a microcontroller (processor) 12 coupled with one or more sensors 14. The device 10 may be powered by a rechargeable battery 16. In one embodiment, the rechargeable battery 16 may be an Li-ion battery. The battery 16 may be recharged via a Universal Serial Bus (USB) port, mini-USB port, micro-USB port or the like. In one embodiment, there a charging base 25 is provided. In these embodiments, the charging base 25 can be plugged into the wall and connects to internet via Wi-Fi or wire. Various embodiments of the base include, but are not limited to, sending an low batter alert email or text to the user, auto-resetting time keeping devices, relaying messages via a external storage location (for example the cloud), monitoring user's physiological parameters for a location external to the body, or playing status updates.

Data storage 18 may be provided to store computer software executable by the microcontroller 12 and the received sensor data from the one or more sensors 14. The device 10 may further include a wireless interface 20 for interfacing with smartphones, tablets, or other mobile devices. For example, in some embodiments, data may be stored on the device 10 and transmitted for processing at a later time. Alternatively, the device 10 may transmit the data in substantial real-time to a user's personal electronics device for data processing. In some embodiments, the wireless interface 20 may be a Wi-Fi or Bluetooth wireless interface.

Device 10 may further include an audio/visual/tactile feedback device 22 for outputting signals to a device user. LED status indicators 24 may also be provided. In certain implementations, the indicators 24 can be an LCD screen, or other screen known by those of skill, such as those regularly used in mobile devices.

The microcontroller 12 may be configured to receive and process the sensor data from the one or more sensors 14. In many embodiments, the microcontroller 12 may be configured to monitor user activity to identify risks associated with certain levels of activity to the user. In many embodiments, the microcontroller 12 may be configured to monitor user orientation to identify risks associated with certain user orientations. Optionally, the microcontroller 12 may be configured to transmit the sensor data from the one or more sensors 14 to a processor housed separately from the device 10 for data analysis at the separate processor. This may be beneficial when increased processing power is desired and/or when reducing a footprint of device 10. The separate processor may be a portable electronic device of the user, a desktop computer, or a related technology.

As shown, certain embodiments provide for a wearable device for capturing abdominal orientation data and delivering feedback to the user. The device may include at least one of: one or more sensors which determine the spatial orientation of the user's abdomen (e.g., relative to the direction of Earth's gravity); a microcontroller that receives and stores orientation data from the sensors and estimates the level of clinical risk over various time scales based on the abdominal orientation, and a communication device and/or output which conveys periodic updates and alerts to the user on their current risk level. As described below in relation to FIGS. 3A-7B, in certain implementations, in use the device 10 may attach to another part of the body such as the chest, neck, shoulder, hip, abdomen, or back during the daytime activities and then may be placed in the sleep position belt during rest or sleep. Further, in certain embodiments, the device 10 and/or sensors may be placed in a variety of locations or a combination of locations on the body, and the algorithm used to process sensor data could be made more or less complex to account for different placements. Additionally, the device could be calibrated to account for different placements and types of motion. In some embodiments, the device may have a low profile so that it cannot be easily seen if place externally.

Advantageously, some embodiments of the systems, devices, and methods may be customized for different users. For example, different women with different physical attributes or severities of disease may benefit from systems, devices, and methods utilizing specialized programs. In some embodiments, the risk assessment and type of feedback provided by the device may be influenced by a number of factors. For example, some factors that may be accounted for include the user's height, weight, age, age of gestation, blood pressure, diagnostic test results (genetic tests, blood tests, urine tests, etc.), time since diagnosis, prior number of device alerts, and/or the doctor's or user's preference on the restrictiveness of their daily activities. Accordingly, in some embodiments, one or more of these factors may be inputted to create a customized algorithm for individual users. As an example, one user might have preexisting hypertension, be obese, be at 35 weeks of gestation, and have a positive diagnostic result for genetic predisposition to preeclampsia. Once these factors are input into the algorithm, the systems, devices, or methods may calculate that the user is at higher risk for preeclampsia and may then provide alerts to the user that are appropriate for higher risk users. In some embodiments, the device could provide feedback over an extended period of time, preventing development of progression of the syndrome. For example, a customized device or system may be more sensitive for higher risk users—alerting the user even when the user has not spent a lot of time in positions that are highly contributive to pressure on intra-abdominal organs. In another example, some embodiments may determine that a young, healthy woman at 20 weeks of gestation is at a lower risk for preeclampsia and may then provide alerts to the user that are appropriate for lower risk users. Accordingly, the user may receive no warnings even when the user has spent a similar amount of time in similar positions as the higher risk user. Optionally, some systems and devices may be configured to suggest that the user check their blood pressure, take a proteinurea test, or check in with their doctor. Alternatively, the device could be configured so that the doctor could communicate directly with the patient.

Embodiments of the system 1 may calculate the risk associated with a plurality physiological parameters and perform a calculation based on the accumulated risk of each of the plurality parameters over a period of time. There may be high risk and low risk parameters but since it is an accumulated calculation, there may be no parameters that are off limits. For example, a pregnant woman's IVC may be temporarily occluded if she lies in the supine position. If she only spends a few seconds in that position and then rolls over on her side, blood flow will resume and she will be fine; however, if she continues to move back to the supine position repeatedly, blood flow may be restricted to a variety of abdominal organs and she could be at risk for either an acute organ dysfunction, or a prolonged stress that leads to a chronic organ dysfunction or failure. Accordingly, some embodiments of the system 1 estimate the pressure, mechanical force, and/or impulse placed on intra-abdominal organs over short time periods (e.g., seconds, minutes, or the like) and/or over very long time periods (e.g., months) and may alert or notify users and/or clinicians if users are experiencing too much cumulative pressure on their organs and tissues.

While some embodiments are generally discussed in terms of monitoring orientation and activity of pregnant women, many methods, devices, and systems may be applied to any other area of the body where different positions have different levels of risk or benefit associated with them. For example, users with obesity related hypertension may benefit from preventing abdominal fat from chronically or periodically compressing renal nerves and abdominal veins which may increase hypertension. In another example, in a user with back pain, the algorithm assigns different levels of risk or detriment to different positions. The cumulative negative impact over time that the user experiences while in various positions is added up and compared to allowable risk-time levels to determine whether the user should be alerted to change position in order to prevent back pain or muscle or nerve inflammation. Devices and methods may be beneficial to users suffering from gastroesophahael reflux or other digestive disorder that require they spend time in certain positions. Other diseases that may benefit from embodiments disclosed herein include Chorea, Parkinson's, and heart disease.

According to one embodiment, as shown in FIG. 1B, the system also has an external server or processor or processors 2 running risk score software 3. The processor 2 can have a central processor unit ("CPU") and main memory, an input/output interface for communicating with various databases, files, programs, and networks (such as the Internet), and one or more storage devices 4. The storage devices may be disk drive devices or CD-ROM devices. The processor 2 may also have a monitor or other screen device and an input device, such as a keyboard, a mouse, or a touch sensitive screen and may be connected to a network 8.

According to one implementation, the processor 2 is in communication with at least one parameter database 5. In various implementations, the parameter database 5 is configured for the accumulation of information relating to each physiological parameter sensor from the user device 10. The parameter database 5 contains information relating to any particular user physiological parameter described herein, such as abdominal orientation, blood oxygen level.

Further, a risk score threshold database 6 may also be in communication with the processor 2. According to one embodiment, the threshold database 6 contains information regarding physiological parameter thresholds in the population that are more likely to lead to complications or fetal conditions during pregnancy. In various implementations, the threshold database 6 may also be in communication with the network so as to revise the thresholds periodically or continuously on the basis of data gathered from various other users, in studies and the like.

The databases 5, 6 can serve as the inputs to and information storage for the system 1, which processes the information as described below and generates any one or more of notifications, reports, suggested actions, and/or instructions to a user or a third party.

The external processor 2 allows access to various network resources. In one embodiment, the central processor 2 also has access, via the network 8 or some other communication link, to external data sources that may be used to keep the information in the databases 5, 6 current.

It is understood that the processor 2 can be any computer known to those skilled in the art. In one embodiment, the central processor 2 includes a website hosted in at least one or more computer servers. It is understood that any system disclosed herein may have one or more such server and that each server may comprise a web server, a database server and/or application server, any of which may run on a variety of platforms.

In one implementation, the central processor 2 includes software programs or instructions to process requests and responses. These software programs or instructions perform calculation, compilation, and storage functions, transmit instructions, and generate reports. It is understood that any embodiment of the systems disclosed herein that provide for data collection, storage, tracking, and managing can be controlled using software associated with the system. It is further understood that the software utilized in the various embodiments described herein may be a software application or applications that are commercially sold and normally used by those skilled in the art or it may be a specific application or applications coded in a standard programming language.

It is further understood that the software can be any known software for use with the systems described herein to track, calculate, and manage the various parameters as described herein. For example, as described in further detail herein, various embodiments of the systems described herein could have any one or more of software for tracking orientation, sleep, blood pressure, blood oxygenation, or software allowing for optimization of any one of these parameters.

In the system, generally, reactive zone data (such as, for example, time and temperature data, etc.) entered into the system via a client computer or processor 2 is received by the processor 2 or server and stored in any of the appropriate databases of the system.

Various implementations of the disclosed devices, systems and methods collect data about the user to monitor fetal risk. As shown in FIG. 6A-7B the system 1 is configured for measuring or estimating physiological parameters, which can then be processed in the manner hereinafter described. In exemplary implementations of the system 1, one or more devices 10 are provided, as described above in relation to FIG. 1. In these implementations, the devices 10 can have multiple sensors 14, such as body orientation sensors. As discussed below, in relation to FIG. 2B, the sensor data may include force data and orientation data. The force data may be $F_x$, $F_y$, $F_z$ force data. The orientation data may be a recline (pitch) angle ($\theta$) and a side tilt (roll) angle ($\phi$). Orientation in 3 dimensions may be defined as below. As is further discussed in relation to FIGS. 3A-5L, in various implementations, the device 10 or devices can be securely attached to the user's body. As shown in FIGS. 6A-7B, in certain implementations, the sensors 14 can also be blood oxygen sensors 92, acoustic sensors 93 and/or an accelerometers 95. In further embodiments, photo sensors, pressure sensors, and ultra wide band ("UWB") sensors can be utilized as well. These sensors 14 are paired with various microcontrollers 12 and/or wireless interfaces 20 (as shown in FIG. 1) so as to allow for the collection, processing and transmission of the sensed data. These devices 10 can therefore be securely disposed on the user's body so as to effectively track a number of variables.

In some embodiments, the device measures or estimates physiological paramenters using a one or more sensors 14, which can be placed in any of a number of soft tissue or skeletal locations. In one example, a blood oxygen sensor 92 might be placed intra- or perivaginally, or on the legs, feet, or toes. In another example, an accelerometer and blood oxygen sensor might be placed on the body above the waist and a second blood oxygen sensor that is placed below the waist, allowing the processor to compare collected physiological data and assess the risk level or possible cause of an irregularity.

In some embodiments this may be done with two or more sensors. For example, a sensor can be placed on soft tissue, such as on the belly button, and another sensor placed on the skeleton, such as on the sternum. In further embodiments, just one sensor may be used. The one or more sensors 14 may include accelerometers, gyroscopes, magnetometers, infrared/temperature sensors, pressure sensors, microphones, oximeters, ultra wide band microwave sensors, radio waves, infrared sensors and/or combinations thereof. In some embodiments, the one or more sensors 14 may be 3-axis sensors or a plurality of single axis sensors. For example, in some embodiments, device 10 may feature a user-programmable gyroscope with a full-scale range of ±250, ±500, ±1000, and ±2000°/sec (dps). In some embodiments, device 10 may feature a user-programmable accelerometer full-scale range of ±2 g, ±4 g, ±8 g, and ±16 g. In some embodiments, the device 10 may feature a magnetometer full-scale range of ±4800 µT. The certain implementations, the device 10 may further include analog-to-digital converters for digitizing the output from the one or more sensors 14 for data recording and analysis.

In some embodiments, different parts of the abdomen may be used for orientation calculations including belly button or estimated center of gravity. In some embodiments, a number of impulse vectors on different organs and tissues may be estimated by the device.

In some embodiments, the device estimates of the center of gravity of the soft tissue in relationship to the musculoskeletal system. In some embodiments this may be done with 2 sensors (one on soft tissue (e.g., belly button) and one on skeleton (e.g., sternum)). In further embodiments, just one sensor may be used which requires empirical or theoretical data to determine where abdominal soft tissue would be expected to be in relationship to interior vessels or other tissues/organs, depending on the age of gestation, height and weight, and number of fetuses etc.

In some embodiments, the device captures various activities like running, driving, etc. and assigns specific values to those which are different for near term and long term analysis. For example, in some embodiments, the device alerts a woman to take a break after 10 minutes of jogging or 30 min of walking, but the algorithm views those short duration as net positives over the period of days or weeks. In some embodiments, the global intra-abdominal pressure or regional intra-abdominal pressures are estimated by the algorithm. In some embodiments, the algorithm views an activity as beneficial for abdominal health initially but later views it as detrimental to health after a certain threshold time. For example, in some embodiments, walking may be initially viewed as beneficial, but reaches an inflection point at 30 minutes, at which point, it may be viewed as detrimental.

In some embodiments, different parts of the abdomen may be used for orientation calculations including belly button or estimated center of gravity. In some embodiments, a number of impulse vectors on different organs and tissues may be estimated by the device.

In some embodiments, the device estimates of the center of gravity of the soft tissue in relationship to the musculo-skeletal system. In some embodiments this may be done with 2 sensors (one on soft tissue (e.g., belly button) and one on skeleton (e.g., sternum)). In further embodiments, just one sensor may be used which requires empirical or theoretical data to determine where abdominal soft tissue would be expected to be in relationship to interior vessels or other tissues/organs, depending on the age of gestation, height and weight, and number of fetuses etc.

In some embodiments, the device captures various activities like running, driving, etc. and assigns specific values to those which are different for near term and long term analysis. For example, in some embodiments, the device alerts a woman to take a break after 10 minutes of jogging or 30 min of walking, but the algorithm views those short duration as net positives over the period of days or weeks. In some embodiments, the global intra-abdominal pressure or regional intra-abdominal pressures are estimated by the algorithm. In some embodiments, the algorithm views an activity as beneficial for abdominal health initially but later views it as detrimental to health after a certain threshold time. For example, in some embodiments, walking may be initially viewed as beneficial, but reaches an inflection point at 30 minutes, at which point, it may be viewed as detrimental.

Figure 6A:
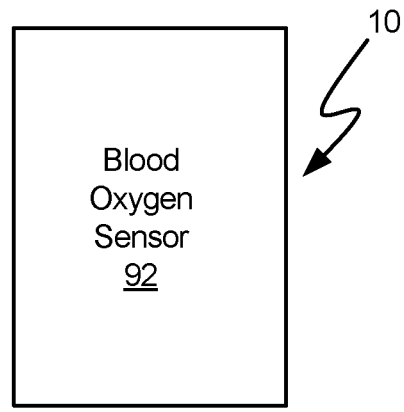
FIG. 6A shows a schematic to demonstrate a system which measures physiological parameters, according to an exemplary embodiment.
Figure 6B:
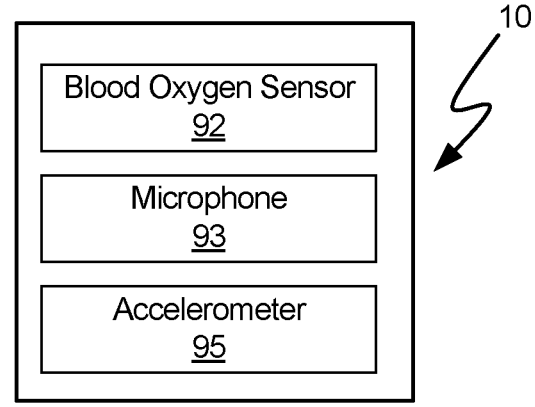
FIG. 6B shows a schematic to demonstrate a system which measures physiological parameters, according to an exemplary embodiment.

Various sensors 14 can be paired with one another depending on the physiological parameters to be assessed. For example, as shown in FIG. 6B, a blood oxygen sensor 92 could be paired with a microphone 93 and an accelerometer 95. In one embodiment, this combined sensor device 10 compares blood oxygen to body orientation using the processor hereinafter described to create a specialized risk profile for each user. In one embodiment, this risk profile is updated throughout pregnancy as the uterus grows bigger and causes more blood flow restriction. It is understood that various alternate implementations of sensor configurations are contemplated herein.

In many embodiments, the one or more sensors 14 may provide force data (e.g., $F_x$, $F_y$, $F_z$) and/or orientation data (e.g., a recline angle $\theta$, a side tilt angle $\varphi$) to the microcontroller 12 for processing. In certain embodiments, the device 10 is configured to track physiological parameters. In certain embodiments, the device 10 is configured to record sensor 14 data through the night or other period of day time which can be reviewed later to determine whether the user is complying with the intended positional therapy. Exemplary processing algorithms are discussed further below.

Figure 2A:
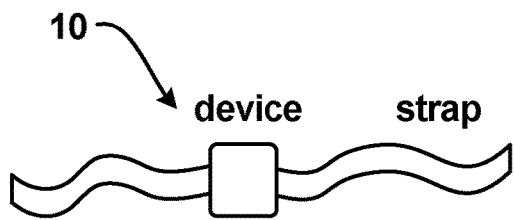
FIG. 2A illustrates an exemplary wearable device for tracking abdominal orientation and/or user activity which attaches to a user by straps.
Figure 2B:
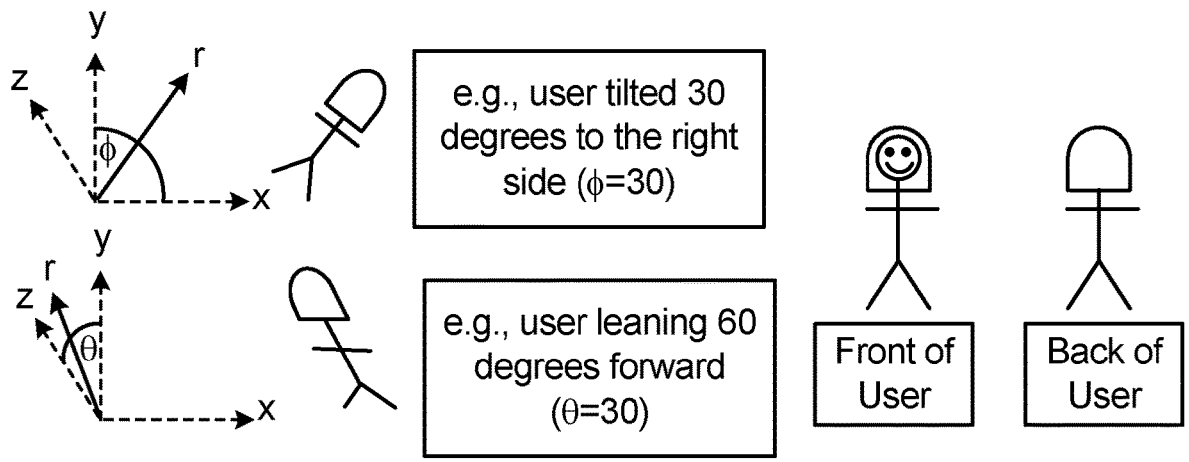
FIG. 2B illustrates an exemplary coordinate system for the user and the device.
Figure 2C:
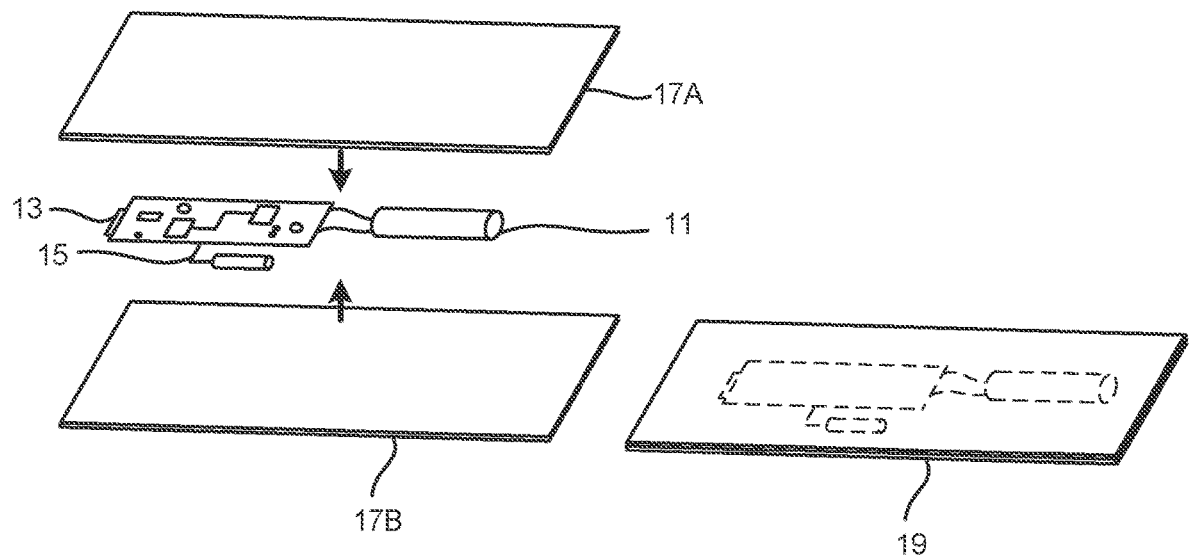
FIG. 2C depicts an alternate implementation of the device embedded in a garment.

As shown in the embodiment of FIG. 2C, in one embodiment, the PCB, battery, vibrational motor and other components of the wearable device are distributed so that they are next to each other rather than overlapping on top of one another. They are each coated with a waterproof polymer barrier and then arranged spaced slightly apart from one another and connected by wires and ribbon cables. They are then placed between 2 layers of fabric in a specially designed shirt. This arrangement makes the electronics as low profile as possible and also allows more flexibility of the shirt to contour more normally to the body during typical wear and movement. In one embodiment, the electronic components themselves are also flexible, such as a flexible circuit board or flexible battery. In one embodiment, the shirt and electronics are a disposable item so that when the battery runs out, the entire system is thrown away.

Figure 2D:
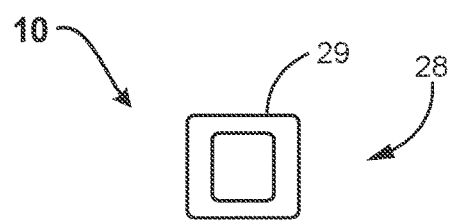
FIG. 2D illustrates an exemplary wearable device for tracking abdominal orientation for placement on the user in a fixed orientation.

As depicted in FIG. 2D and FIGS. 3A-7B, in certain embodiments, the device 10 can be configured to be mounted on the user in a fixed orientation via an external mounting device 28. In various implementations, this can be done by adhesive 29 (as shown in FIG. 2D), housed in a garment 30 (FIG. 3A-3I or 7A-B), or through use of an external mounting device or clip 74 (FIGS. 4A-5L) so that it maintains the same relative orientation to the user at all times. In various implementations, these external mounting devices 28 can have a variety of sensors, as is shown in FIGS. 6A-6B.

In the embodiments of FIGS. 3A-I, the external mounting device 28 is a garment 30 for keeping the device 10 in a fixed orientation can have a pouch or pocket 32. As shown in FIGS. 3A-F, in various embodiments the pocket 32 is configured such that the device 10 fits snugly into the pocket 32 and does not fall out during normal activity of the user 40.

Figure 3A:
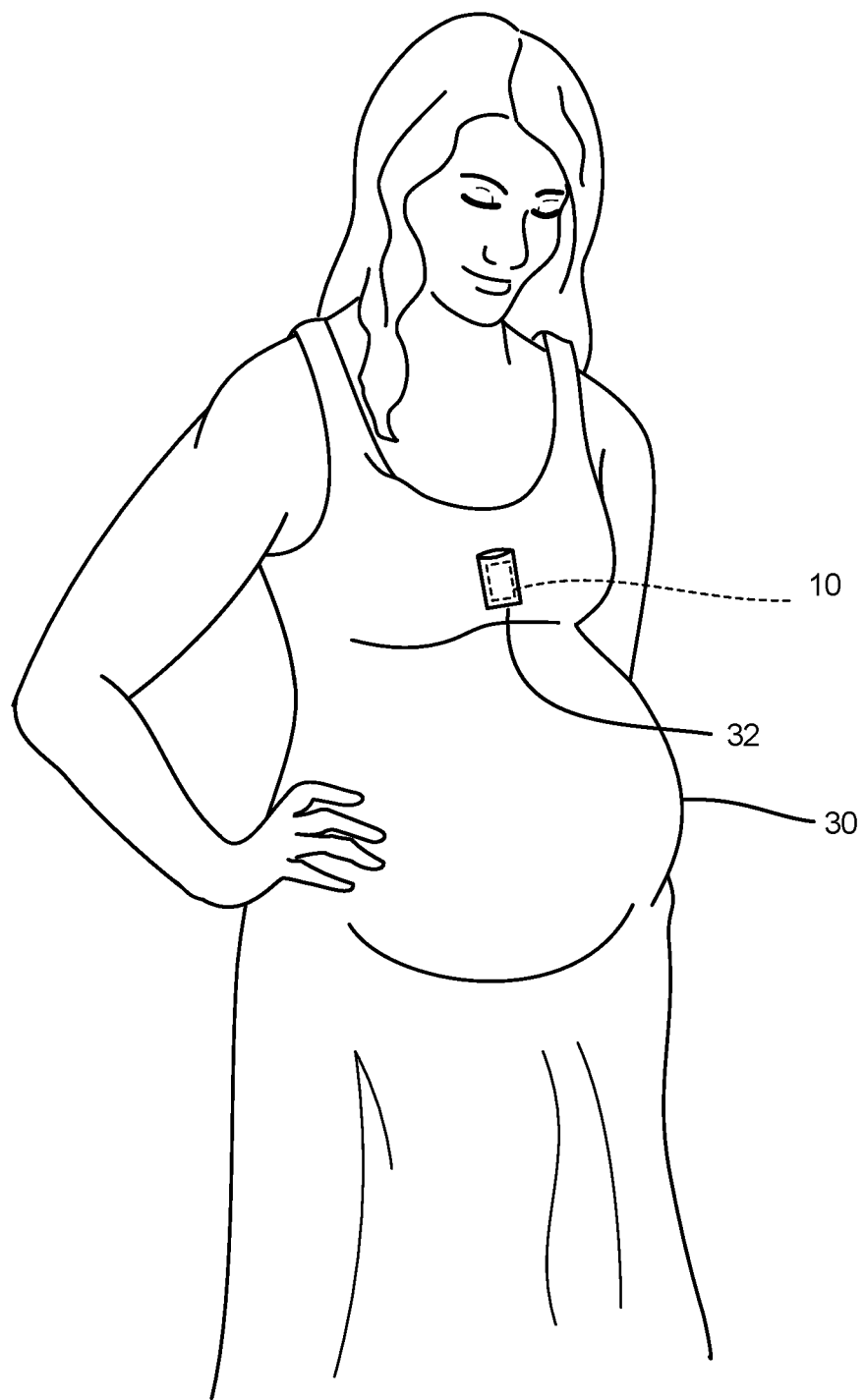
FIG. 3A depicts an implementation of a garment configured to local the device on a user's body.
Figure 3B:
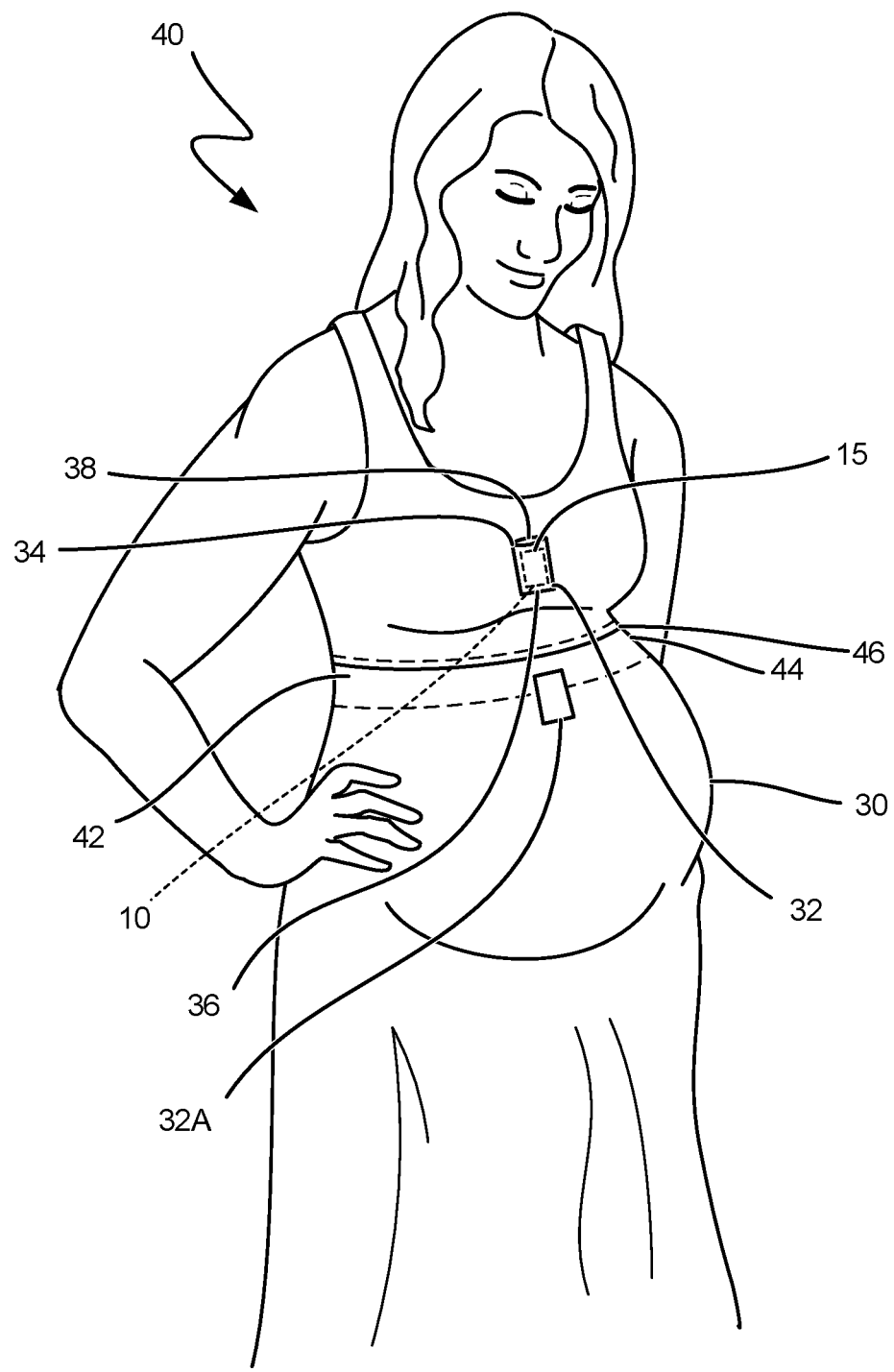
FIG. 3B depicts a further implementation of a garment, according to several embodiments, showing various device placements on or above the abdomen of the user.
Figure 3C:
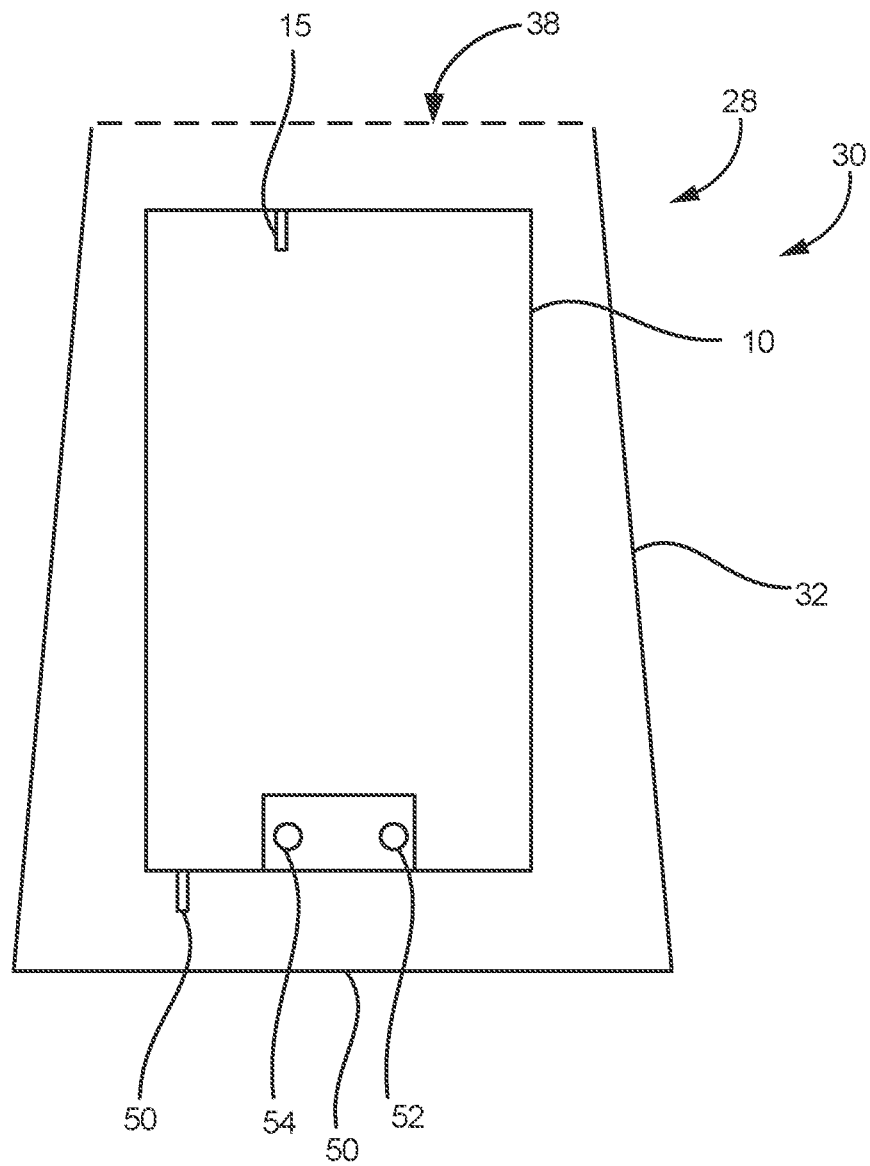
FIG. 3C depicts a front view of an embodiment of the device placed in a pocket, according to one implementation.
Figure 3D:
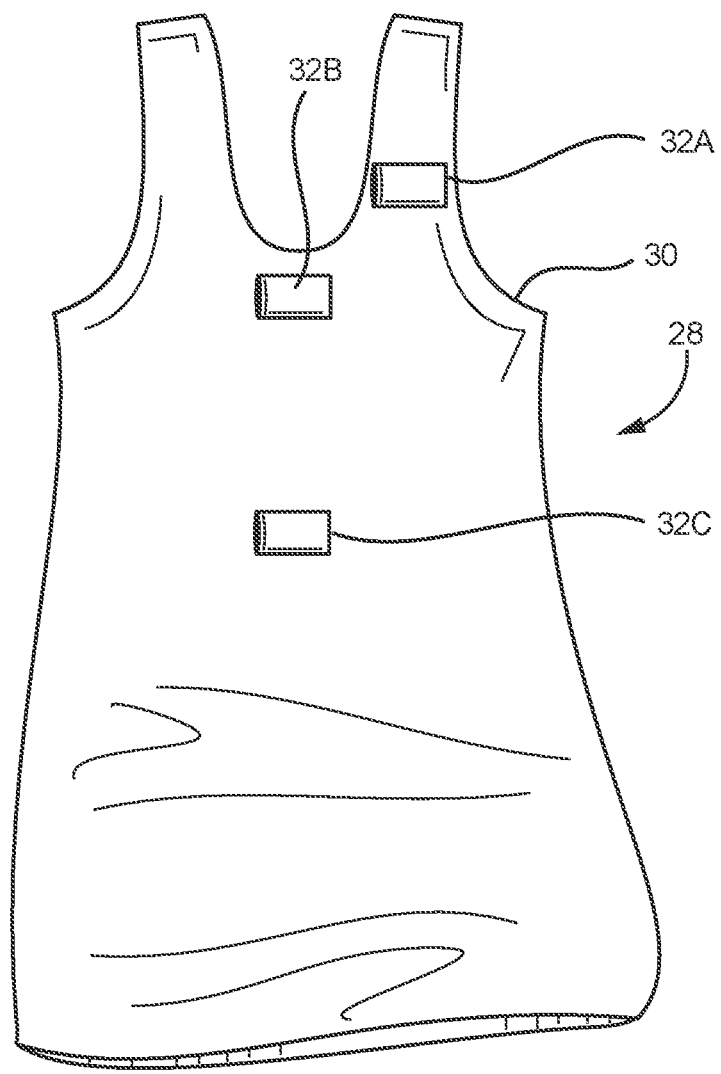
FIG. 3D depicts a further view of a garment showing several possible device placement implementations.
Figure 3E:
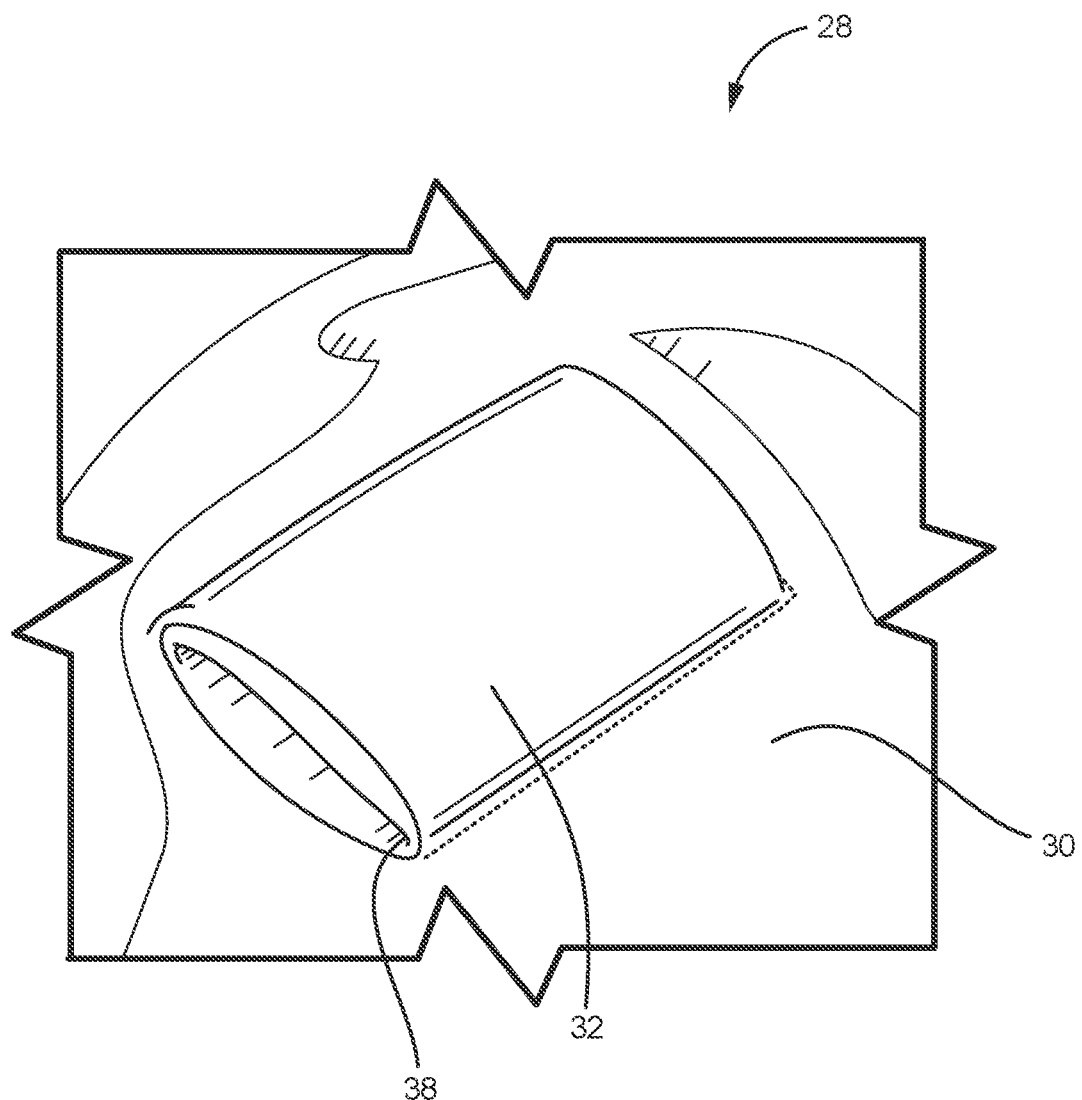
FIG. 3E depicts a perspective view of a pocket, according to one embodiment.

In certain implementations, and as shown in FIGS. 3A-C, the garment 30 has multiple pouches 32, 32A aligned vertically. In these embodiments, the user 40 can place the device 10 in any of the pouches 32, 32A as desired for comfort and use. In certain implementations, the pocket 32 may be oriented so that the device 10 is in the same orientation relative to the user 40 each time the device is placed within the pocket 32. In exemplary embodiments, the pocket 32 has a first end 34 and a second end 36, and can be sewn onto the front of the shirt 30 just below the breasts and is very slightly smaller than the device 10 so that the device fits snuggly into the pocket 32 between the first end 34 and second end 36 without moving in relationship to the pocket 32. In certain embodiments, the pocket 32 has an opening 38 on the first end 34 of the pocket 32, which can be slightly smaller than the rest of the pocket.

As shown in FIG. 3A-C, the garment 30 is a shirt that fits snugly around the chest just below the breasts of the wearer 40. In certain embodiments, the garment 30 might have a support band 42, which is placed below the breasts and extends around the torso 44 so that the device and pocket are held more securely against the body of the user 40, or an integrated strap 46 fitted around the chest just below the breasts. In various implementations, the integrated strap 46 is adjustable and allows the user to tighten or loosen the strap to adjust comfort as well as dictate how firmly the sensor device is held against the body of the user 40. In alternate embodiments, the garment may be looser fitting.

Figure 3F:
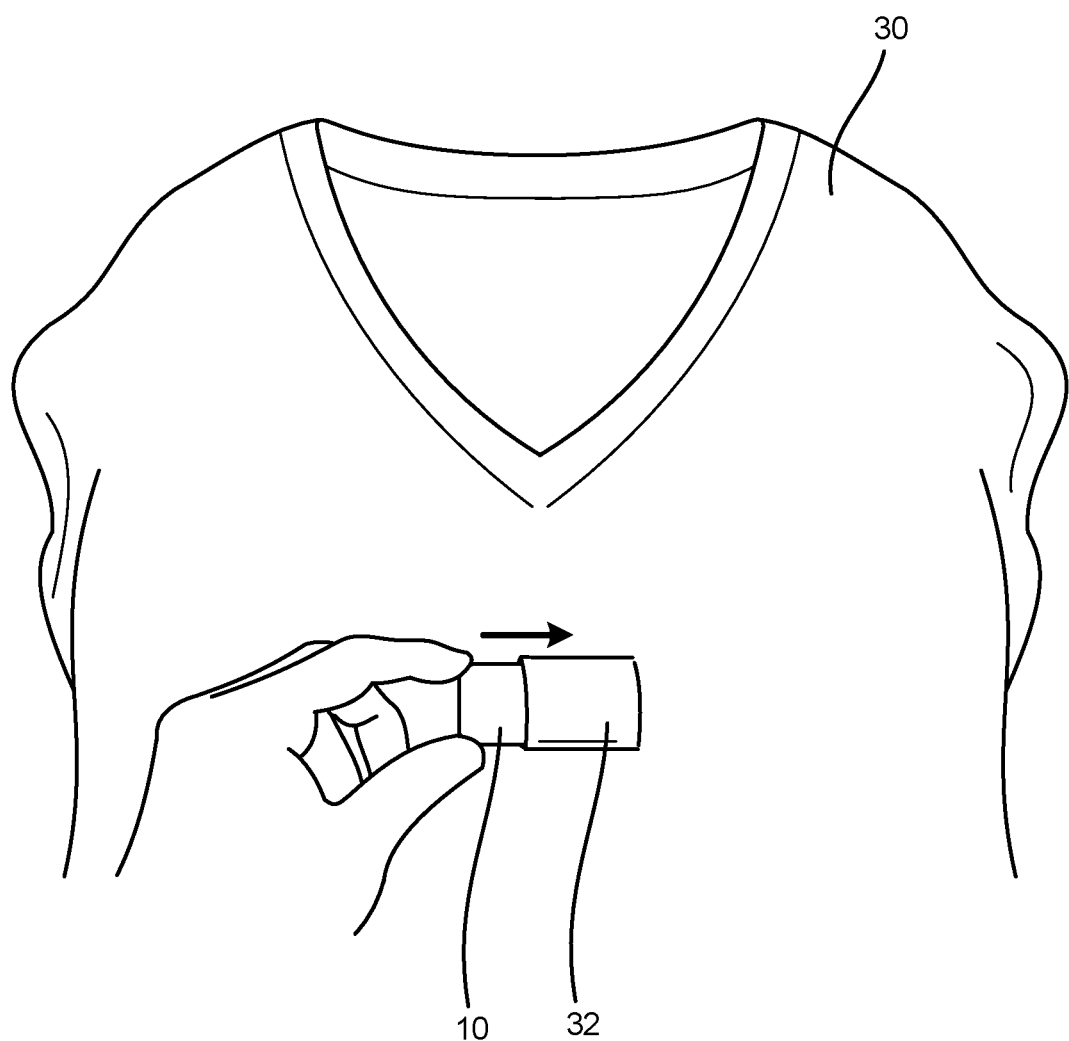
FIG. 3F is a front view of an implementation of a garment and pocket, showing device insertion.

As shown in FIGS. 3C and 3F, in certain embodiments, the device 10 is placed into a pocket 32, the device 10 prompts the user to recalibrate. In one embodiment, the interior of the pocket 32 has a conductive region 50 disposed such that placement of the device 10 in the pocket 32 is sensed by at least one electrode 52, 54 disposed on the device 10 and configured to come into electrical communication with the conductive region 50 so as to close a circuit, as would be appreciated by a skilled artisan. In an alternate embodiment, the device 10 can have a projection 56 that is triggered when the device 10 is placed in the pocket 32. In various embodiments, the projection 56 can be a lever, button, magnet or other sensor that alerts the device to require a calibration.

Figure 3G:
FIG. 3G is a three-quarters rear view of an implementation of a garment having a support pad.

As shown in FIG. 3G, in certain implementations, the garment 30 further comprises a belt 58 with a support 59. The support 59 or supports can be foam pads or projections integrated into the belt 58 so as to prevent the user from assuming a supine position while seated. These supports 59 thereby discourage certain maternal sleep or daytime positions for the purpose of preventing complications of pregnancy described elsewhere herein.

Figure 3H:
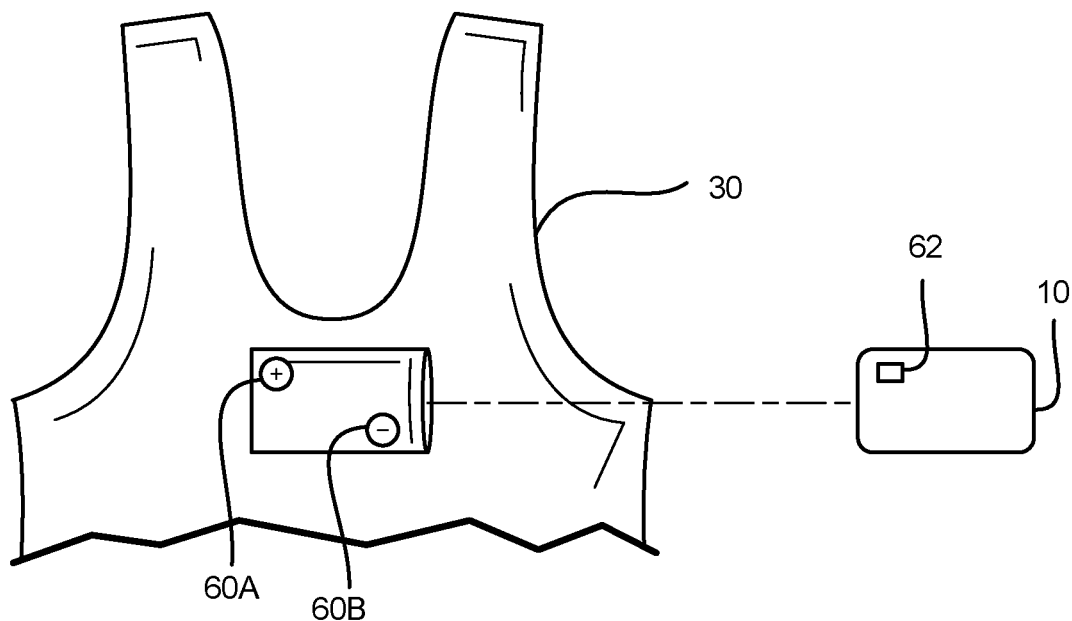
FIG. 3H is a front view of an alternate embodiment of a garment, having a pocket with at least one magnet disposed within.
Figure 3I:
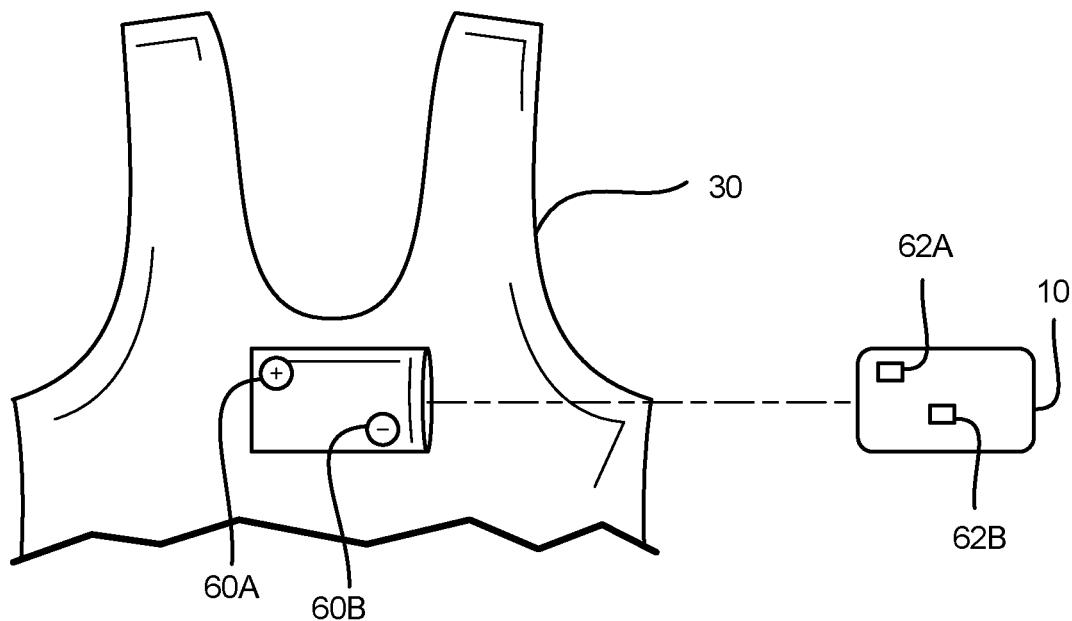
FIG. 3I is a front view of a further implementation having a device with multiple magnetometers.
Figure 3L:
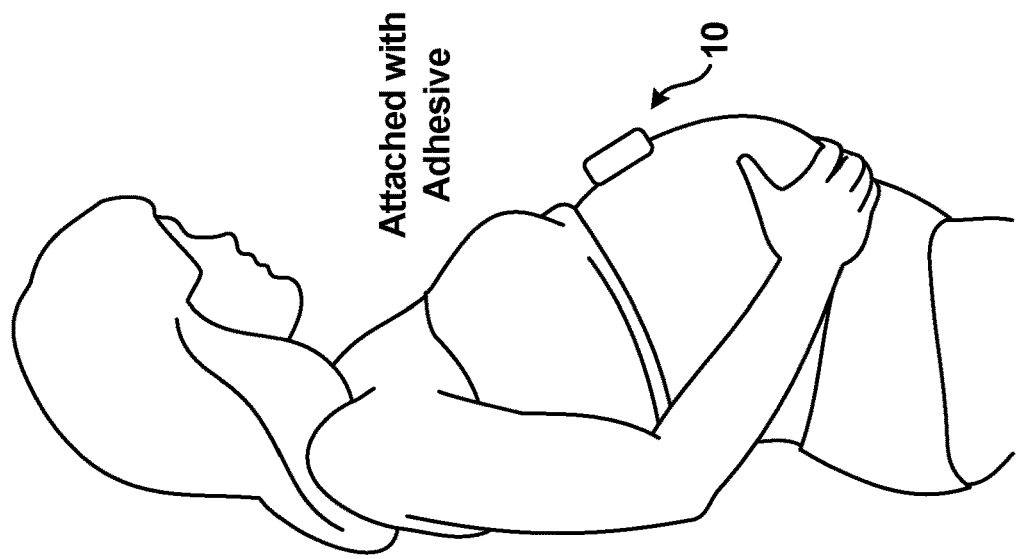
FIG. 3L illustrates the exemplary wearable device of FIG. 2D placed on and attached to a user at an exemplary location.
Figure 3K:
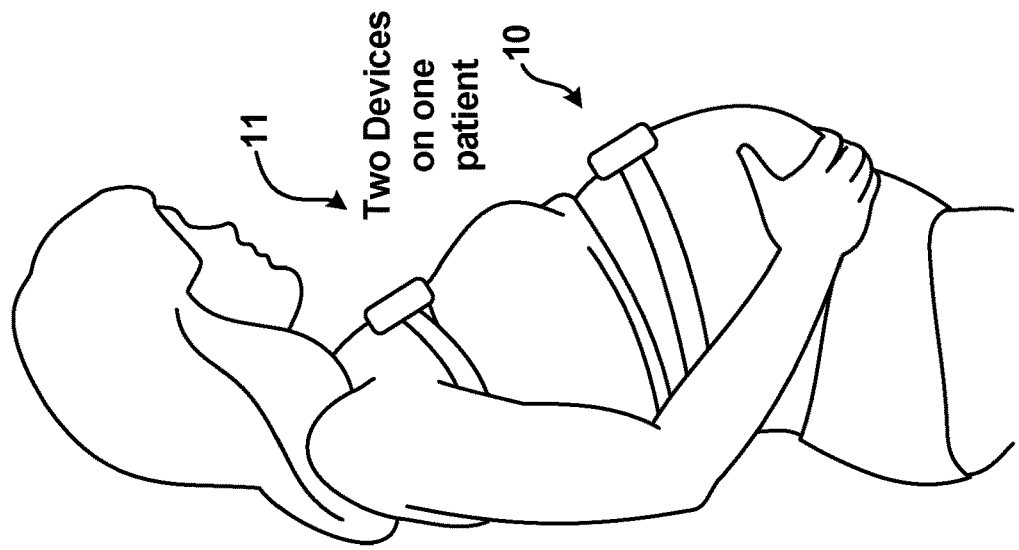
FIG. 3K illustrates an exemplary system for tracking abdominal orientation and activity including the exemplary wearable device of FIG. 2A in combination with another exemplary wearable device for tracking abdominal orientation and activity (which may be identical to the exemplary wearable device illustrated in FIG. 2A).
Figure 3J:
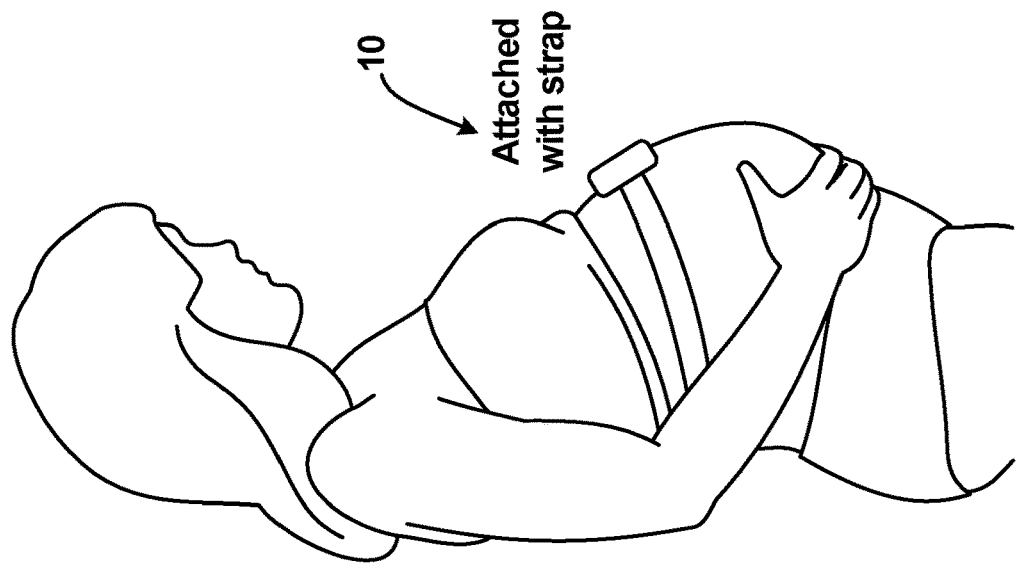
FIG. 3J illustrates the exemplary wearable device of FIG. 2A placed on and attached to a user at an exemplary location.

As shown in FIGS. 3H-I, in certain implementations, the garment 30 has at least one magnet 60 which are detected by a magnetometer 62 (FIG. 3H) or magnetometers 62A, 62B (FIG. 3I) disposed within the sensor device 10. In one embodiment, the device 10 turns on or becomes functional when the magnetometers 62 sense the magnets 60 and know the device has been placed on the user. In some embodiments, the polarity of the magnets 60, 60A is such that the device 10 can only be activated when it is placed in the proper orientation on the body. In one embodiment, if the magnetometers 62 detect magnets in the incorrect position, the device 10 will issue an alert to notify the user the device is not positioned properly.

Data conveying physiological parameters could be used in many other ways, including, but not limited to, determining whether the device was being utilized, activating a power-save mode, determining which physiological profiles indicate high risk groups, suggesting tests and treatments, calculating percent compliance, and recognizing high risk patterns as a way of engaging in preventative treatment. In some embodiments, the data could be communicated in a variety of ways, including, but not limited to, wireless intra-sensor communication, wireless connectivity to a mobile device, or connection to the primary device via wires.

FIGS. 4A-G depict further implementations of a wearable device 70 and/or clip 74. It is understood that the wearable device 70 of FIGS. 4A-4G having magnets can be any of the devices disclosed elsewhere herein in reference to number 10.

Figure 4A:
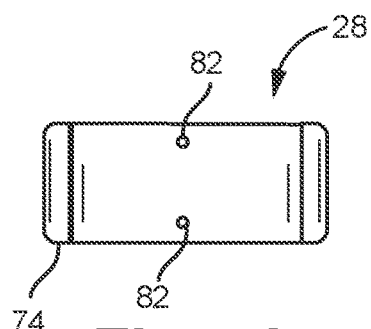
FIG. 4A shows a mating piece, according to an exemplary embodiment.
Figure 4B:
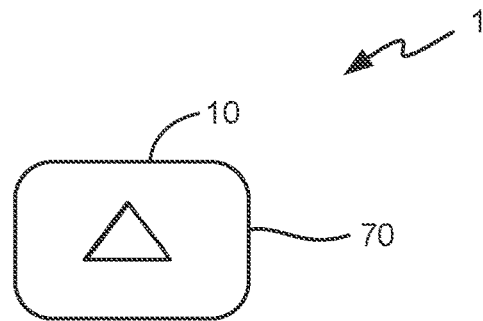
FIG. 4B shows a wearable device, according to an exemplary embodiment.
Figure 4C:
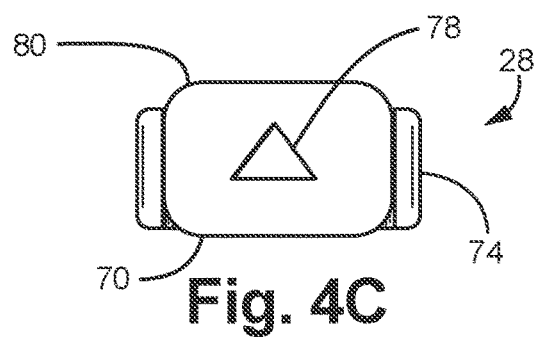
FIG. 4C shows a wearable device paired with a mating piece, according to an exemplary embodiment.

As shown in FIG. 4C, in one embodiment, the device is designed to be positioned on the torso with an arrow 78 on the device face 80 pointing upwards. As shown in FIG. 4A, in a further embodiment, the mating piece 74 and device 70 have protrusions 82 or indentions that fit together. This geometric interlocking prevents the parts from rotating in relation to each other. Since the magnets 72A, 72B, 76A, 76B urge the device 70 and mating piece 74 tightly together, the projections 82 are correspondingly pulled into the indentions and thus when trying to rotate the parts in relation to each other, they encounter mechanical interference.

Figure 4D:
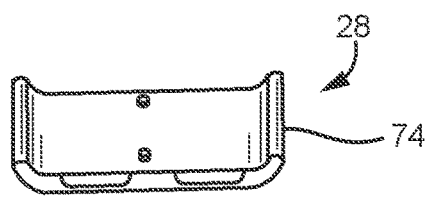
FIG. 4D shows a mating device in perspective, according to an exemplary embodiment.

In one embodiment, as shown in FIG. 4D, the mating piece 74 is symmetrical in at least two planes so that the mating piece 74 can magnetically attach to the device in a wide variety of orientations. This eliminates the need to carefully align the mating piece under the clothes with the device above the clothes. No matter how the mating piece is oriented, it will immediately clip in place correctly.

Figure 4E:
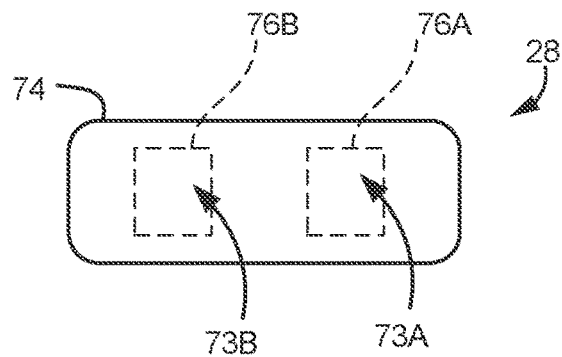
FIG. 4E shows an example of how magnets could be placed in a mating piece.
Figure 4F:
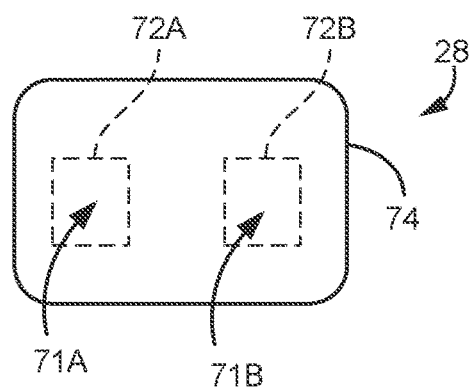
FIG. 4F shows an example of how magnets could be placed in a wearable device.

As shown in FIGS. 4E-F, various implementations of the system 1 have a wearable device 70, in which at least one magnet 72A, 72B is attached or embedded, and a mating piece 74 also having at least one magnet 76A, 76B, wherein the magnets are arranged so that the two parts only magnetically connect in predetermined preferred orientations. In various embodiments, once engaged, these magnets 72, 74 prevent the wearable device 70 from easily rotating. In exemplary embodiments, the device 70 and mating piece 74 each have two magnets 72A, 72B, respectively, such that they can only attach in one orientation due to the polarity of the various magnets. This prevention of rotation ensures that the user is always wearing the device in the proper orientation so her orientation risk can be calculated accurately.

In one embodiment, the centers 71A, 71B, 73A, 73B of the magnets are about 0.5 inches apart. This separation 71A, 71B prevents the device 70 and mating piece 74 from easily rotating in relationship to one another.

In one embodiment, the device 70 and mating piece 74 are configured to be mounted on opposite sides of a cloth garment, such as a shirt. This configuration allows the sensors—such as the accelerometer and microphone—to be disposed inside or outside of the garment, as desired.

Figure 4G:
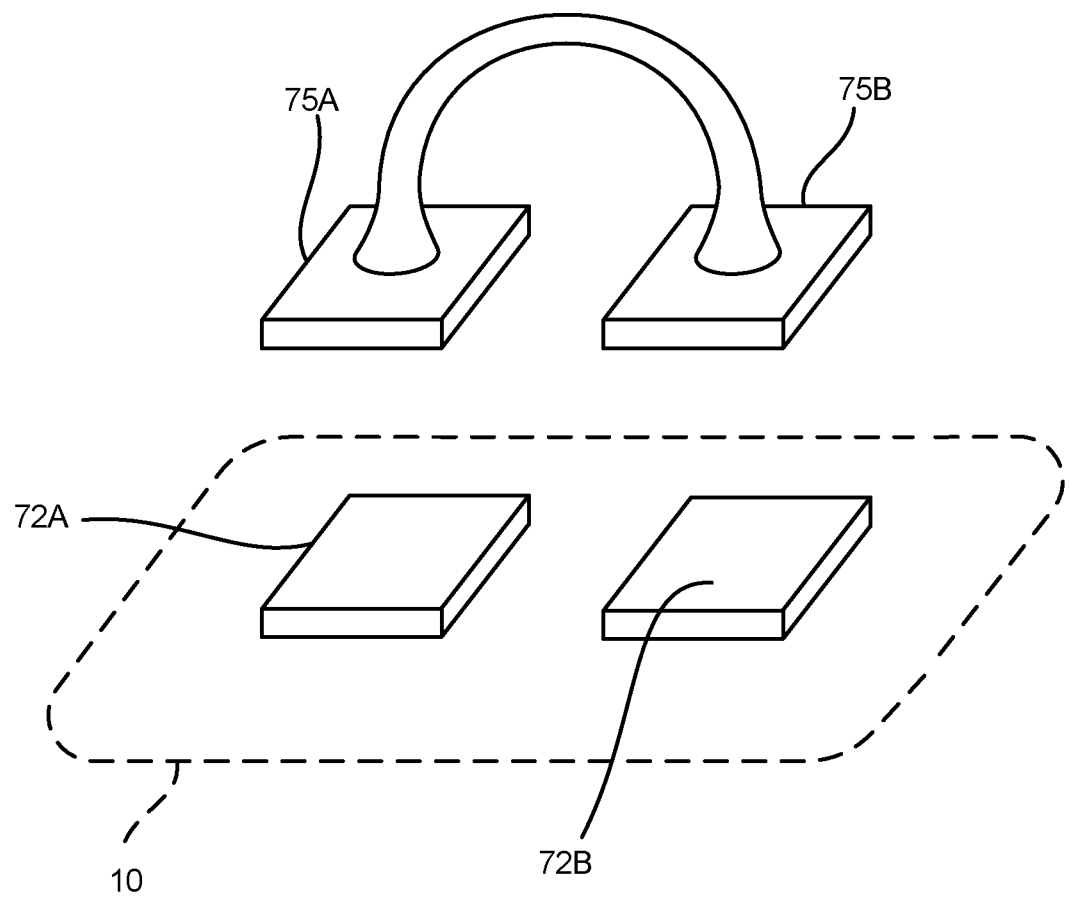
FIG. 4G shows an exemplary embodiment in which a metal clip mates with magnets in a device.

In one embodiment, as shown in FIG. 4G, one or more magnets 72A, 72B are attracted to ferrous metal mounts 75A, 75B that have a similar shape as the magnets 72A, 72B. In an exemplary embodiment, the sensor device 10 has magnets 72A, 72B which are 1 cm×1 cm×1 mm disposed 1 cm apart. The mating clip 75 has ferrous metal mounts 75A, 75B which are also 1 cm×1 cm×1 mm and are also 1 cm apart from each other. When the clip 75 and the device 10 come in close proximity to each other, the magnets will have a natural tendency to attract to the metal squares such that the magnets 72A, 72B and mounts 75A, 75B will only attract to each other in one of 2 possible orientations, "right side up" and/or "upside down." Any other orientation will self-correct into one of the preferred orientations.

Figure 5A:
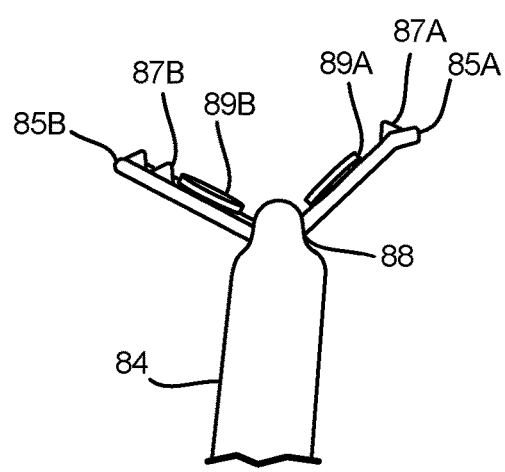
FIG. 5A shows an open clasping mechanism, according to an exemplary embodiment.
Figure 5B:
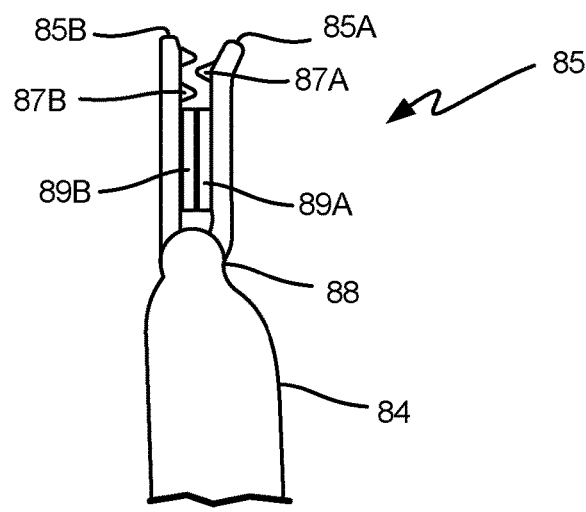
FIG. 5B shows a closed clasping mechanism, according to an exemplary embodiment.
Figure 5C:
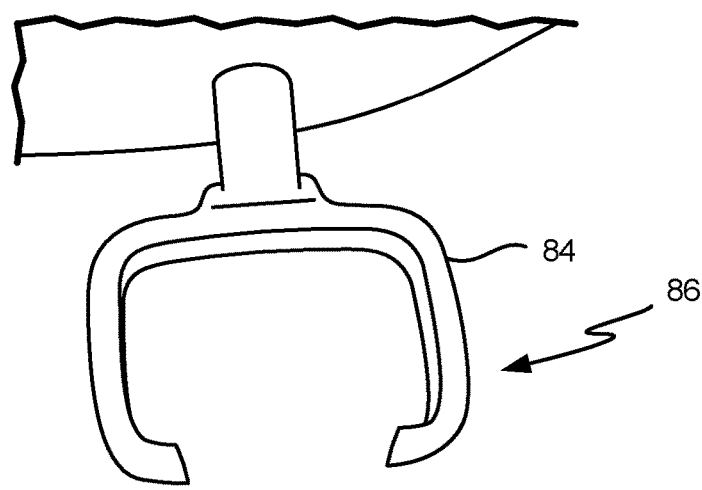
FIG. 5C shows a clasping mechanism, according to another exemplary embodiment.
Figure 5D:
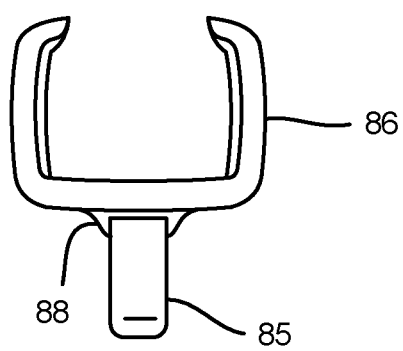
FIG. 5D shows a front/back planar view of a clasping mechanism, according to an exemplary embodiment.
Figure 5E:
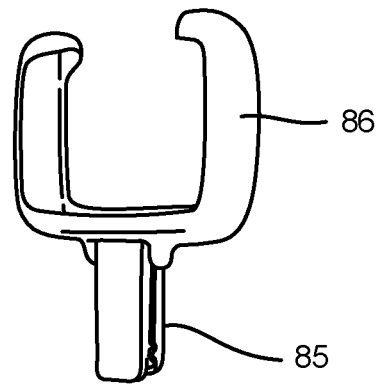
FIG. 5E shows a perspective view of a clasping mechanism, according to an exemplary embodiment.
Figure 5F:
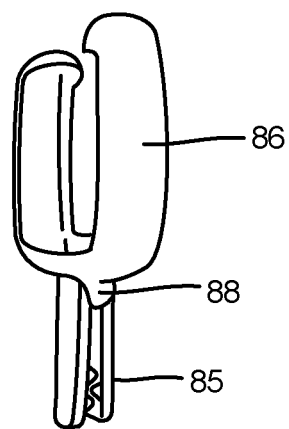
FIG. 5F shows another perspective view of a clasping mechanism, according to an exemplary embodiment.
Figure 5G:
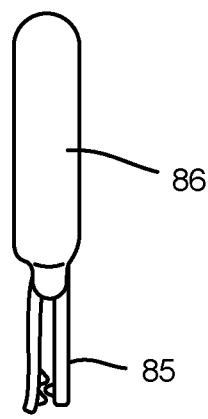
FIG. 5G shows a side planar view of a clasping mechanism, according to an exemplary embodiment.
Figure 5H:
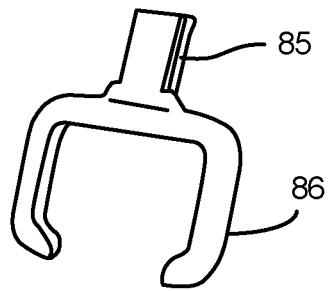
FIG. 5H shows another perspective view of a clasping mechanism, according to an exemplary embodiment.
Figure 5I:
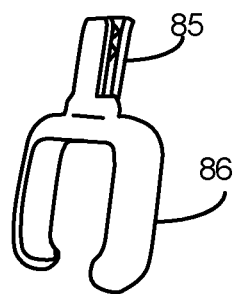
FIG. 5I shows a side planar view of a clasping mechanism, according to an exemplary embodiment.
Figure 5J:
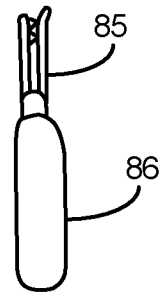
FIG. 5J shows a side planar view of a clasping mechanism, according to an exemplary embodiment.
Figure 5K:
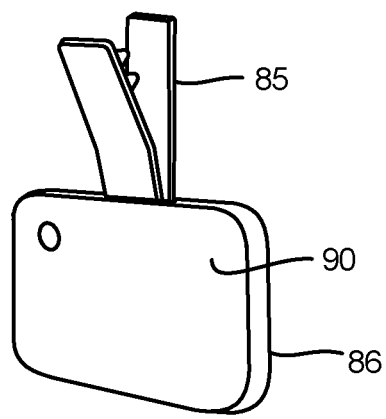
FIG. 5K shows a slightly opened clipping mechanism, according to an exemplary embodiment.
Figure 5L:
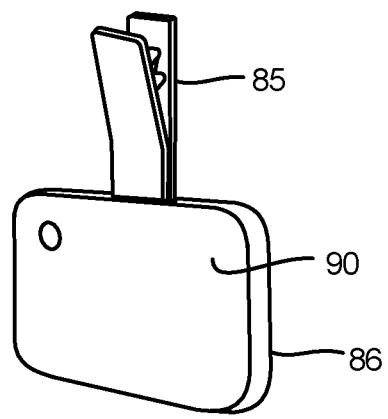
FIG. 5L shows a closed clipping mechanism, according to an exemplary embodiment.

As best shown in FIGS. 5A-J, certain embodiments of the system 1 further comprise a clasping device, or clip 84. In these implementations, the clip 84 has a clasping region 85 and a coupling region 86. In various embodiments, and as shown in FIGS. 5A-B, the clasping region 85 has a first arm 85A and a second arm 85B. Each of the arms 85A, 85B is disposed around a first hinge 88, and can have clasping portions 87A, 87B and/or magnets 89A, 89B configured to create a physical and/or magnetic connection, for example around an item of clothing, such as a bra.

As shown in FIG. 5C-L, in these implementations, the coupling region 86 is configured to accept the wearable device 90. In various embodiments, the hinge 88 not only allows the clasping region 85 to open and close, but also allows the clip 84 to freely move with respect to the clasping region 85. This is important because a pregnant user's abdomen will increase in size throughout pregnancy, so if the clasping region arms 85A, 85B are rigid in relation to the rest of the clip 84 and device 90 the hinge these components will uncomfortably dig into the abdomen or sternum. Similarly, if the user bends forward at the waist, the clip hinge needs to rotate so the clip does not dig into the skin.

In one embodiment, the magnets 89A, 89B are disposed below the clasping portions 87A, 87B so that they can come in direct contact with each other rather than in just "close" contact through the bra material. This enables the clasping region 85 to have the strongest possible connection with the minimal amount of magnet material since magnetic force falls as the inverse cube of the distance. By having the magnets 89A, 89B contact each other they have the strongest possible attractive force to each other. This arrangement also allows the projections to have a very thin profile since the magnets and ridges and projection material don't all need to be layered on top of each other.

In one embodiment, the magnets 89A, 89B are not visible, but are covered by a layer of fabric or plastic or other material on the clasp (not shown). However, the arrangement of the magnets below the clasping portions 87A, 87B allows for a strong magnetic connection as the magnetic force does not need to span the distance created by the pinched bra fabric or the clasping portions 87A, 87B.

In one embodiment, the outside surface of the clasping region 85 between the bra and the skin is flat so that it is not uncomfortable against the skin. In another embodiment, the clasping region 85 on the outside of the bra is curved away from the bra at the top so that a user's fingers can easily pry the clasp open.

In one embodiment, the clip 84 does not have magnets but instead uses a mechanical latch. In one embodiment, the clip 84 does not have magnets but instead uses clasping portions 87A, 87B that are flexible enough that they can be pried apart and slipped over the bra material but rigid enough so that they create a firm grip on the bra material.

In one embodiment, the clasping portions 87A, 87B are sufficiently long so that when the clasping portions 87A, 87B clasp the bra material, the clip 84 and device 90 do not significantly swing left or right when the user lays down on her side. This is important so that the device 90 is able to identify whether the user is on her side or is on her back or upright.

In various embodiments, the hinge 88 is a standard hinge. In various embodiments, the hinge 88 is a living hinge made of flexible material that allows the clasp to open. In various embodiments, the hinge 88 is a locking hinge that is freely moveable until it is locked in place. For example, the device could be attached to clothing in a variety of configurations including, but not limited, a to a hinge, an automatically locking hinge, a user-activated locking hinge, or Velcro.

In one embodiment, the clip 84 attaches to the bottom of the bra material between the cups. This ensures that the device 90 hangs straight down from the center of the sternum so that is aligned properly on the body.

In certain implementations, the system utilizes a material worn on the abdomen or chest that reflects UWB waves and a device that transmits UWB waves towards the body and receives the reflected signal. In these implementations, a device can be utilized by running an algorithm that identifies breathing characteristics based on the movement of the chest. In certain embodiments, the system uses material having a distinct pattern which can be recognized by an algorithm, as would be understood. For example, in one embodiment, the material has a repeating geometric pattern of holes. In another embodiment, the material has a non-repeating unique pattern that can be used to determine chirality of the reflective material. In this case, the algorithm can tell whether the UWB waves are going through the body and then reflecting off of the back surface of the material or are bouncing off the front of the material before penetrating the body. In some embodiments, the reflective material is one or more of the following materials: aluminized mylar, thin strips of metal, reflective polymers, or metal mesh.

In further embodiments, the device captures various physiological parameters and provides feedback based on the intensity and time span of the measurement collected. For example, in some embodiments, the device alerts a woman to take a break after 10 minutes of jogging, but the algorithm views those short duration as net positives over the period of days or weeks, however the data but reaches an inflection point after 10 minutes, at which point the time span could be considered detrimental. In one embodiment, the blood oxygen sensor 92 identifies various respiration characteristics such as normal breathing, shallow breathing, snoring, apnea or no breathing and assigns them different risks. When the moving average risk crosses a predetermined threshold an alert is issued. In additional embodiments, and as shown in FIG. 6B, the device 10 also uses a microphone 93 and/or accelerometers 95 to measure breathing characteristics.

Figure 7A:
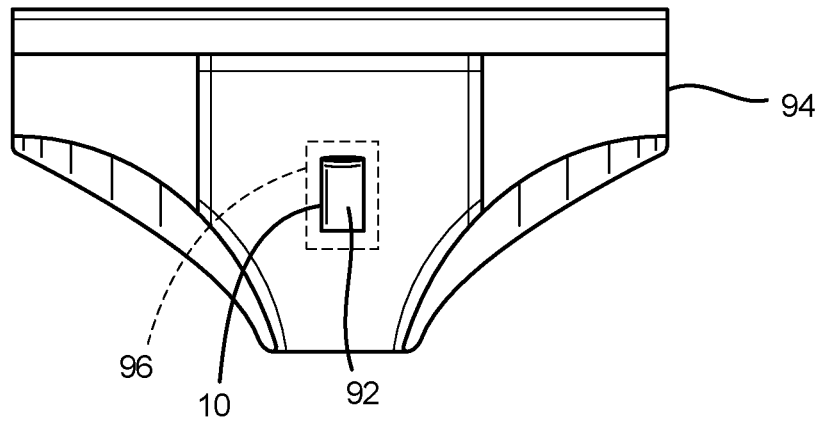
FIG. 7A shows a pair of smart underpants, with a pocket which might hold sensors or devices.
Figure 7B:
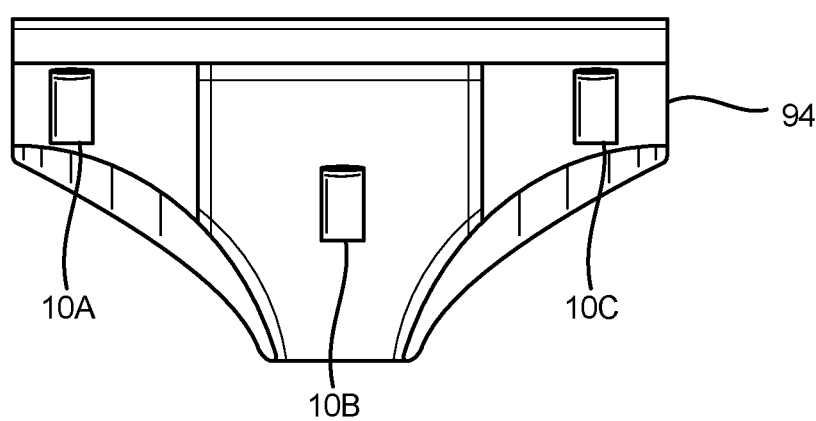
FIG. 7B shows a pair of smart underpants, with multiple pockets which might hold sensors or devices.

In another example, as shown in FIG. 7A, the device 10 could have a blood oxygen sensor 92 integrated into a pair of "smart underpants" 94. In certain embodiments, also shown in FIG. 7A, the "smart underpants" could have a pocket 96 configured to house the blood oxygen sensor 92 or device 10. Alternatively, as shown in FIG. 7B, the underpants 94 could have sensors 10A, 10B, 10C in different locations to get a more accurate indication of orientation and blood oxygen level. For example, a system of sensors attaches to an existing pair of underpants or a specially designed pair of underpants. The device can be removed so that the device can be easily cleaned and used with a clean pair of underwear.

Returning to FIG. 2B, an exemplary coordinate system for the user 40 and the device 10. In FIG. 2B, forces along the user's 40 left to right side may be represented by measured forces along the x-axis (left side to right side of the device). Forces along the user's vertical axis (e.g., feet to head) may be represented by measured forces along the y-axis (bottom of the device to the top of the device). Forces from the user's back to front may be represented by measured forces along the z-axis (front surface to back surface of the device).

Also illustrated, rotation values around the x-axis (called the recline angle and represented by θ) may range from lying face down to sitting/standing straight up to lying face up. Further, rotation values around the z-axis (called the side tilt angle and represented by φ) may range from lying on the left side to sitting/standing straight up, to lying on the right side. It should be understood that the illustrated coordinate system is exemplary and not limiting.

In certain implementations, the device must be calibrated. In various implementations, the device 10 can be calibrated to account for different variations on physiological parameters. In one example, the device may be placed in an imperfect orientation on the body and then calibrated appropriately. The user uses a magnetic clip to attach the device to her shirt, so that the device is reclined by 20 degrees and tilted to the left 30 degrees. A calibration sequence is initiated when the user is standing still in the upright position and presses a calibration start button. Optionally, the calibration procedure may provide a brief pause (e.g., 1-5 seconds) between when the user presses a calibration start button and when the calibration calculations begin in order to allow the user to get into a preferred position. In another example, the system has a snoring calibration function where the user wears the device and makes snoring sounds in order to determine the correct default values for the snoring algorithm. The device could tell the user when to make sounds and could use the processor algorithm adjust the threshold value according to the calibration.

The calibration may be performed by taking the average of each of the x, y, and z values over a time or measurement period (e.g., last 10 measurements or last 1-10 seconds) and checking to see if values of each of the x, y, and z variables are relatively unchanged. If unchanged, this indicates that the user is standing very still, and thus, the calibration constants may be recorded. For example, if measurements are received at 0.1 second increments, at 0.1 seconds, a first data point may be recorded ($x_1$, $y_1$, $z_1$), at 0.2 seconds, a second data point may be recorded ($x_2$, $y_2$, $z_2$) and so on over the calibration time period (1-10 seconds for example). The new data point generated every 0.1 seconds may be put into a new variable (e.g., $x_{new}$, $y_{new}$, $z_{new}$). At every 0.1 second increment, the calibration algorithm may check if the subsequently received values are within a desired percentage (1-5%) of the initial reading (e.g., $x_1$, $y_1$, $z_1$). For example, the algorithm may check to see if the new variables are within 2% of the initial reading:

$$0.98*x_{new} \leq x_1 \leq 1.02*x_{new}$$

$$0.98*y_{new} \leq y_1 \leq 1.02*y_{new}$$

$$0.98*z_{new} \leq z_1 \leq 1.02*z_{new}$$

If the equation is satisfied, it may continue to the next measurement. If at any point, any of the values are not within the desired percentage, the calibration sequence may restart with a new initial reading (e.g., $x_1$, $y_1$, $z_1$). When the calibration time period (1-10 seconds for example) passes without any of the x, y, or z values fluctuating more than the desired percentage (e.g., 2%), the calibration constants may be recorded and an orientation calibration may be performed where:

$$\text{cal.theta} = \arctan\left(\frac{z_1}{y_1}\right)$$

$$\text{cal.phi} = \arctan\left(\frac{x_1}{y_1}\right)$$

Variables cal.theta and cal.phi may be subtracted from the raw theta and raw phi values. As would be apparent to one of skill in the art, various alternative algorithms can be used to establish the theta and phi calculations.

In one embodiment, the calibration algorithm is given by:

cal.phi=arctan ($y1$/sqrt($z1^2+x1^2$)*180/pi)

cal.theta=arctan ((-$x1$/((sign of $z1$)*(sqrt($z1^2$+ 0.01*$y1^2$))))*180/pi)

In these embodiments, whenever the device acquires sensor data, it will subtract the "cal.theta" and "cal.phi" variables from the theta and phi values calculated from the raw data coming into the algorithm from the sensors. As such:

Raw data is given by:

sensor.phi=arctan($y$/sqrt ($z^2+x^2$)*180/pi)

sensor.theta=arctan((-$x$/((sign of $z$)*(sqrt($z^2$+ 0.01*$y^2$))))*180/pi)

Calibrated data is given by:

real.phi=sensor.phi−cal.phi real.theta=sensor.theta−cal.theta

In some embodiments, the following alternate xyz plane is defined as:
y=g's of force from y-sensor (axis of person's left hip to right hip)
x=g's of force from x-sensor (axis of feet to head)
z=g's of force from z-sensor (axis of back to front)
In some embodiments, the phi and theta equations are modified in order to stabilize the functions where:

$r$=sqrt($x^2+y^2+z^2$)

phi($\phi$)=arctan($y$/sqrt($x^2+z^2$))*180°/$\pi$ theta($\theta$)=arctan(-$x$*(sign of $z$)/sqrt($z^2+u*y^2$)) *180°/$\pi$ where u is a constant with a preferred range between 0.001 and 0.3, and where "sign of z" simply inserts a negative 1 when z is negative and a positive 1 when z is positive.

In certain embodiments, the device can also be calibrated to recognize certain positions or to stop reading any combination of x, y, or z axis outputs. In one example, the microphone and processor could be configured detect only the amplitude of sound and recognize snoring by identifying short regular amplitude bursts over a set period of time, or it could be configured to analyze both the amplitude and frequency of the sound to determine if the sound is snoring or some other ambient noise.

An example of this approach is the following: every body orientation has a set amount of time in which the user is allowed to be before an alert is issued. In one embodiment, every single unique combination of side tilt and recline angles has a different total amount of time associated with it. In one embodiment, a recline angle of −90 degrees with 0 degrees side tilt (flat on back) has the very lowest amount of time allowed (2 minutes). A combination of recline angle −73 degrees and side tilt 7 degrees has a maximum time of 4 minutes and 22 seconds. A combination of −35 recline and −82 side tilt has no maximum time value (infinity) because it is considered completely safe. Every time the user moves orientations, the algorithm instantly calculates how much time the user has left in that position. The remaining time is transferred and prorated to the new position. So, if the user has been flat on her back for 1 of the maximum 2 minutes allowed by the algorithm and then shifts to recline −75 and side tilt 7, she will have 50% of the time left for the new position (2 min and 11 seconds).

In one embodiment, the system is a health monitoring system with one or more sensors for generating sensor data, configured to identify health risk values associated with the sensor data; assign the risk value to a corresponding time value; adjust the time values continuously based on new risk values; and output a warning when the risk value persists for the direction of the time value.

In various embodiments, the following variables and logic are used in the algorithm to establish the risk of time spent in various "zones". For purposes of these implementations, there are different zones that the user can be in for different amounts of time. In one such implementation, each zone has a threshold value ("Zone1Thresh", "Zone2Thresh" etc. . . . ) associated with it as well as its own health time ("Zone1Time", "Zone2Time", etc. . . . ). The health threshold values are in ascending order starting from zone 1.

In one exemplary embodiment, the system defines 3 zones that have the following values:
Zone 1: 0.2 health score threshold for 20 sec.
Zone 2: 0.4 health score threshold for 30 sec.
Zone 3: 0.6 health score threshold for 60 sec.
The device vibrates when a user is below a threshold level for the amount of maximum time for that zone's health threshold. In various implementations, if a user is not in zones 1, 2, or 3, an alert will not be generated. But, if the user goes into zone 1 and stays there for 20 seconds, an alert is generated. If the user goes into zone 2 and stays there for 30 seconds, an alert is generated. And, if a user goes into zone 3 and stays there for 60 seconds an alert is generated.

In these implementations, if a user goes into a zone for less than the alert threshold time and then transfers into a new zone, the time is carried over into the new zone in a prorated manner. For example, take the case where a user is only allowed to spend 60 sec in zone 3 or 30 sec in zone 2 before an alert is triggered, where zone 2 is considered less healthy than zone 3. If the user has been in zone 3 or 40 seconds and then transfers into zone 2, the algorithm will multiply 40 sec times 30/60 (ratio of max time in zone 2 over zone 3) for a new value of 20 sec. The user will now have only 10 seconds (30 sec max minus 20 sec prorated carry-over from previous zone) left in zone 2 before the alert is issued.

In one example, a user has been at a health score of 0.7 for an hour and they then change position so their new score is 0.5. They are in that position (and in zone 3) for 30 seconds and then transfer into a new position and have a health score of 0.3 (zone 2). The 30 seconds they spent in zone 3 is now carried over to zone 2 but the time is prorated to account for the difference in maximum times between zones.

Similarly, in a new case where the user has spent 20 sec in zone 2 and they transfer into zone 3, the algorithm behaves as though the user has been in range 3 for 40 seconds (20 sec times 60/30) and will have 20 seconds (60 sec max−40 sec carryover) until the alert is issued.

If the user goes to a position that has a health score higher than 0.6 so they are out of the alert zones all together, the clock resets back to 0.

In a further embodiment, the number of consecutive vibrational alerts are programmed uniquely for each zone. In one embodiment, zone 1=5 consecutive vibrations, zone 2=3 consecutive vibrations, and zone 3=1 vibration.

In another embodiment, the risk and time values are based on continuous equations so there are an infinite number of risk and time levels. In one embodiment, different risk equations are used to cover different quadrants of space.

In another embodiment, more than 1 real time risk variable is used in the risk calculation equation. In one embodiment, the overall risk is a direct function of both body orientation and snoring so that the alert is more likely to go off when the user has high risk values for each of body orientation and snoring.

In another example implementation, a wearable device 10 having a microphone and a processor creates a time series of estimated fetal activity scores where the fetal health is related to both the frequency of and intensity of fetal movements as detected by the microphone. An average fetal health score is calculated as an average of all the fetal activity over a period of 4 hours. If the average fetal health score drops below a threshold level at any point, an alert is generated. In another embodiment, the processor counts all the fetal movements over a certain threshold size in a given period of time. If the total number of movements in a 4 hours period is less than the threshold number (for example 20), an alert is generated.

In one example, the system 1 could have a device 10 for assessing and correcting sleep position which can be worn in any orientation on the chest or neck or abdomen during sleep as long as it is relatively parallel to the bed mattress surface. During "night mode" an algorithm only uses measures the z-value (direction perpendicular to the mattress). When z=−1, the user is facing upwards. When z=0, it is assumed the user in on her side since the user is not likely to be vertical when asleep. By using only the z direction, the user no longer needs to put the device on the body in a certain orientation and if the device rotates during sleep the algorithm will still accurately assess sleep position.

In various implementations, the device and system can provide alerts to the user. The feedback device 22 may have one or more displays, light indicators, speaker(s), and/or vibration motor(s) for outputting signals to a device user. In certain embodiments, the device 10 is configured to issue vibrational alerts. The feedback device 22 may also provide an audio output. For example, the feedback device 22 may provide beeping warnings or vocal feedback/suggestions to the user. The feedback device 22 may also provide a haptic feedback with a vibration motor. For example, the device 10 could use a blood oxygen sensor 92 to measure a physiological parameter, and could then issue an alert described above when blood oxygen falls below a certain level. In some embodiments, when the cumulative orientation risk value rises above the medium risk threshold, the device may vibrate, beep, or flash once every two minutes until the cumulative orientation risk value improves and drops below the threshold. If the cumulative orientation risk value rises above the high risk threshold, the device may vibrate, beep, or flash twice every thirty seconds until the cumulative orientation risk score drops below the high risk threshold. The device may provide no feedback when the cumulative orientation risk score is below the medium and high thresholds. Optionally, the device may provide a visual feedback when the cumulative orientation risk score is below the medium and high thresholds (e.g., a green indicator or the like). The described feedback and thresholds are exemplary. It should be understood that the feedback alerts may have any number of configurations and may be customized by a clinician or a user.

For example, a display may display risk scores, orientations, activity levels, etc. to a user. Optionally, the device could provide specific verbal advice regarding body orientation or medication needs, for example, "don't lean back so far." Additionally or alternatively, light indicators may provide feedback. For example, light indicators may be a row of five lights that progressively light up to provide a warning to a user. Optionally, the light indicators 24 may provide various color outputs for different degrees of warning (e.g., green, yellow, red, etc.), or may signal power status, battery status or connectivity status. A variety of vibration intensities or audio volumes might be used depending on user position.

In some embodiments, the alerts could be configured to give more specific feedback. For example, the device 10 has an arterial oxygen saturation ("SpO$_2$") sensor that can be used when needed. The system could remind the user to activate SpO$_2$ functionality only on certain nights depending upon sensor results over a specific time span. At one time, a user may have multiple previous sleep sessions where their SpO$_2$ levels are very good and they also snore very infrequently; therefore the system would not recommend that they use the SpO$_2$ attachment on a given night. Conversely, at another time, if the system sensed low SpO$_2$ levels and significant snoring many nights in a row, the system may recommend that the user use the SpO$_2$ sensor on a given night.

In some embodiments, the device may include a training system alerts which teach the user which orientations or activities are considered risky. For example, in training mode, the device buzzes once when the user enters a position of risk level 0.2 to 0.39, buzzes twice for risk level 0.4 to 0.59, buzzes 3 times for risk level 0.6 to 0.79, and buzzes continuously for risk level 0.8 to 1. In alternate embodiments, the algorithm can be adjusted to alternate ranges with slightly different maximum amounts of time allowed based on their level of risk. In one embodiment, all body orientations fit into 1 of 100 different categories from Range 100 (healthiest) to Range 1 (least healthy). A minimum health threshold can be set so that all Ranges above a certain level of health never cause the algorithm to issue an alert. In this case, all Ranges over 45 are considered healthy for a specific user. The user can spend varying amounts of time in Ranges 1 through 45 before an alert is issued. In this case, the user can spend 10 sec plus ("the range #" times 2). So, in Range 45, the user can spend 100 seconds (10+45×2) before an alert is issued. In Range 20, a user can spend 50 sec (10+20×2). In range 1, a user can spend 12 seconds (10+1×2). And, in each case, time spent in other ranges affects the amount of time the user can spend in the new range. This time carryover affect can happen continuously until an alert is issued or the user enters a health orientation (Range 45 or higher).

In some embodiments, the processor may use algorithms to calculate force, pressure, or other measurements, which would show how the body is being affected by different physiological parameters. In one embodiment, the algorithm could be constructed using imaging techniques and empirical data. In other embodiments, the algorithm could be adapted based on physiological data from other users. In alternate embodiments, the processor could use an algorithm to determine whether a given physiological parameter value is caused by a global or localized stimuli.

For example, the system could detect snoring and use an algorithm to adjust the data sensor measurements. In this example, the device acquires microphone sound amplitude or voltage data at a rate called "MicSampleRate," typically occurring between 0.5 Hz and 10 Hz. An algorithm is then employed by the system 1 to detect sounds that exceed certain defined noise and frequency thresholds. For example, the system could identify user snoring by uses a "SnoreStartConsec" parameter. For example, if the "SnoreStartConsec" parameter is set at four, the device will begin to collect data when the microphone and system detect four or more consecutive amplitudes above "HeavySnoreStartAmpThresh," which by way of example can be set at about 50 db and/or "LightSnoreStartAmpThresh" which by way of example can be set at about 30 db. Likewise, the system could also detect when a period of snoring has ended by employing another algorithm defining low volumes and frequency. For example, when there are two or more sounds consecutive detected amplitudes that qualify as "SnoreEndConsec" (default value 2) consecutive (or more) amplitudes below "HeavySnoreEndAmpThresh" (default value of 20 db) or "LightSnoreEndAmpThresh" (default value of 10 db). Between these two functions, the device could collect data regarding the user's snoring profile.

Variable "SnoringState" is generated at the same rate as "MicSampleRate". It may have 4 different values: heavy snoring, light snoring, not snoring, unknown.

In the previous embodiment, the default values of the variables may change based on specific user characteristics such as whether they have a partner who snores or how close the device is to their mouth.

In some embodiments, the processor would calculate the risk associated with a certain physiological parameter. For example, the system 1 might be used for monitoring breathing during sleep. Sensors would collect the desired physiological parameter and use an algorithm that identifies health risk values associated with the sensor data to produce a time series of identified risk values. The cumulative risk value could be determined and updated by calculating a moving average for a subset of the time series of identified risk values associated with the sensor data. Then, the cumulative risk could be compared a threshold value, and the device could output a warning when the cumulative risk value crosses the first threshold. In a further embodiment, the algorithm assigns a risk score based on the breathing rate, where consistent regularly spaced breaths are given the highest score and long intermittent stoppages in breathing are given the lowest score. An exemplary equation that would be part of this algorithm is provided by:

Healthiest score=1,

Riskiest score=0;

Score over last 10 minutes=1/(2*# of breathing stoppages greater than 10 seconds)^0.5.

Similarly, in another example, the length of the breathing stoppage impacts the risk score generated: Score over last 10 minutes=1/(3*# of breathing stoppages greater than 15 seconds+2*# of breathing stoppages greater than 10 but less than 15 seconds) ^0.5. In these implementations, the processor could use an algorithm to calculate a moving average as described above. In one embodiment, the breathing algorithm is as follows:

a. Acquire accelerometer data at a rate called "BreathSampleRate" (between 0.5 Hz and 30 Hz; default 8 Hz).
b. "BreathSignal" equals accelerometer value "Pctx"*"accelx"+"Pctz"*"accelz".
c. "accelx" equals the accelerometer value in the x direction, "accel y" is the y direction accelerometer value
d. "Pctx" and "Pctz" have values from −100% to 100% (−1 to 1) where the absolute values of "Pctx" and "Pctz" must equal to one but one or both can be negative (eg in one example BreathSignal is 0.7x-0.3z).
e. Variable "BreathState" is generated at the same rate as "BreathSampleRate". It may have 4 different values: inhale, exhale, none, unknown.
f. "BreathSignal" is logged continuously for the last "BreathTestDuration" seconds (default 5 sec). The most recent "Breath #" (default 3) "BreathSignal" recordings are averaged to create "RecentAveBreathSignal" and the next "Breath #" (eg 3) most recent "BreathSignal" values are averaged into "PastAveBreathSignal".
  i. For example, if "Breath #"=3, then "RecentAveBreathSignal"=the average of the 3 most recent "BreathSignal" values and "PastAveBreathSignal"=the average of the 4th, 5th, and 6$^{th}$ most recent.
g. If the absolute difference between "RecentAveBreathSignal" and "PastAveBreathSignal" is greater than the variable "BreathNoiseMargin" (default value 0.1 g) then "unknown" is recorded for "BreathState".
h. If "RecentAveBreathSignal" is greater than "PastAveBreathSignal" by "DynamicBreathMargin" (default value 0.005 g) then "BreathState" is given a value of "inhale". If "RecentAveBreathSignal" is less than "PastAveBreathSignal" by "DynamicBreathMargin" then "BreathingState" is recorded as "Exhale". If they are within the "DynamicBreathMargin" range (eg between −0.005 and 0.005), then "none" is recorded.
i. The algorithm continuously reviews the last "BreathTestDuration" (eg 5 sec) seconds to determine if a full breath has occurred. A binary variable "BreathPeak" is recorded whenever at least "% breaths" (default 50%) of the first half of the time segment (2.5 sec in this case) is inhale and at least "% breaths" (50%) of the 2$^{nd}$ half of the segment (2.5 sec) is exhale.
j. "AveBreathRate" is recorded as the average time between all individual "BreathPeak" values which do not have an "Unknown" event between them.

k. "NoBreathCount" is increased by 1 every time no BreathPeaks are recorded for "NoBreathTime" (default 15 sec). Each time this occurs a variable "NoBreathEvent" is recorded as the time between breaths. Note, this calculation is performed when a new breath is detected so that the time since the last breath can be recorded. Otherwise, it will record a time of 30 sec for each one.

l. A full intensity vibrational alert (5 bursts) may be issued (optional) when "# NoBreaths" (default 3) occur within a window of "NoBreathTimeWindow" (default 10 min).

In one embodiment, the algorithm has the ability to detect breathing during a subset of the night in order to limit battery consumption. For example, variables "TimeBreathDetectOn" (default value 2 minutes) and "TimeBreathDetectOff" (default value 28 minutes) would test breathing for a 2 min segment every half hour. Setting "TimeBreathDetectOff" to 0 makes breathing detection continuous through the entire night.

Figure 9:
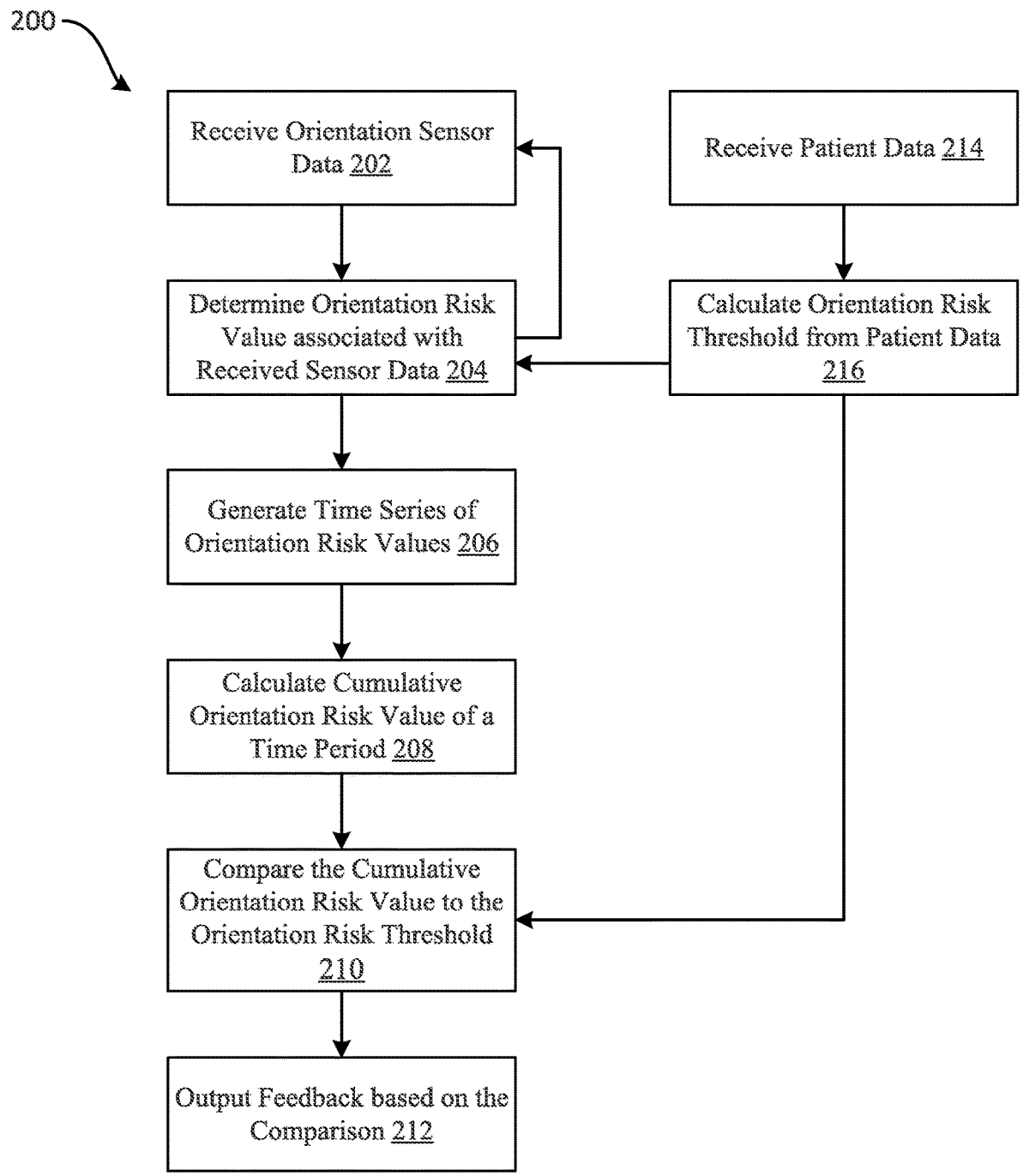
FIG. 9 illustrates an exemplary method for monitor orientation risks.

FIG. 9 illustrates an exemplary method 200 for monitor orientation risks 110, for example in preventing preeclampsia. At step 202, orientation sensor data is received. Based on the received orientation sensor data, a determination of an orientation risk value can be made 204. Steps 202 and 204 may be repeated for a continuous stream of orientation sensor data to generate a time series of orientation risk values 206. From the time series of orientation risk values, a cumulative orientation risk value may be calculated 208. The cumulative orientation risk value may then be compared to an orientation risk threshold 210. Feedback may then be outputted to the user 212 based on the comparison of the cumulative orientation risk value to the orientation risk threshold. Optionally, the method 200 may further include receiving user data 214. An orientation risk threshold may be calculated or adjusted in response to the received user data 216 to provide a customized orientation risk threshold. This customized orientation risk threshold may be used in the comparison 212.

The orientation data may be a recline angle ($\theta$) and a side tilt angle ($\varphi$). Each combination of $\theta$ and $\varphi$ may correspond to an "Instant Position Risk Score." For example, this score may range from 0-1 (or scales thereof) where 1 may be indicative of the most dangerous orientation. Continuing with the exemplary scale, in some embodiments, oriented face down (while not lying on the stomach) may be valued at 0-0.05, preferably about 0.03; leaning forward at 45 degrees may be valued at 0.05-0.10, preferably about 0.08; standing straight up may be valued at 0.08-0.12, preferably about 0.10; leaning back at 45 degrees may be valued at 0.35-0.45, preferably about 0.4; and lying on back may be valued at 1.0.

FIG. 10A illustrates exemplary orientation risk values for combinations of phi and theta. These orientation risk values may be stored as a look up table and accessed by the processor to associate orientation risk values to received orientation data. Alternatively, the processor may implement orientation risk value equations to calculate the orientation risk values.

For example, in the illustrated table of orientation risk values, six constants are provided: risk value for laying on the left side ("left side risk" i.e., when phi is equal to −90 degrees), risk value for laying on the right side ("right side risk" i.e., when phi is equal to 90), risk value for a headstand ("headstand risk" i.e., when theta is 180 or −180 and phi is 0), risk value for flat on stomach ("on stomach risk" i.e., when theta is −90 and phi is 0), the risk values for reclining by more than −90 degrees when not tilted sideways ("recline by more than −90 risk" i.e. when theta is between −90 and −180 and phi is 0), and risk value for standing upright ("standing risk" i.e., when theta is 0 and phi is 0). These constants may be defined by a clinician and may be adjusted for fine tuning the orientation risk values in the matrix (e.g., to provide customized risk values specific for the user). The remaining risk values may be determined based on the six defined constants.

In the exemplary matrix the six constants may be defined as follows:

$risk_{left\ side} = 0$ $risk_{right\ side} = 0.3$ $risk_{headstand} = 1.0$ $risk_{stomach} = 0.01$ $risk_{-90 < recline < -180} = 1.0$ $risk_{standing} = 0.1$ These constant values are exemplary for monitoring preeclampsia and may be adjusted.

In the illustrated table, when the user is reclined backward by between −90 and −180 degrees (−90>theta>−180) and tilted to the left (phi is between 0 and −90), the risk value may be calculated by:

$$risk = risk_{left\ side} + (1 - risk_{left\ side}) * risk_{-90 < recline < -180} * \sqrt{1 + \sin\left(\frac{\pi\varphi}{180}\right)}$$

When the user is reclined backward between 0 and −90 degrees or −90 degrees (i.e., 0<theta≤−90), and tilted to the left (phi is between 0 and −90), the risk value may be calculated by:

$$risk = risk_{left\ side} + (1 - risk_{left\ side}) *$$
$$\left(risk_{standing} + (1 - risk_{standing}) * \left(1 - \cos\left(\frac{\pi\theta}{180}\right)\right)\right) * \sqrt{1 + \sin\left(\frac{\pi\varphi}{180}\right)}$$

Further, when the user is recline backward or flat on his/her back (i.e., 0<theta≤−90 and phi is 0), the risk value may be calculated by:

$$risk = risk_{standing} + (1 - risk_{standing}) * \left(1 - \cos\left(\frac{\pi\theta}{180}\right)\right)$$

When the user is not reclined or leaning forward (i.e., theta is 0) and is tilted to the left (phi between 0 and −90 degrees), the risk value may be calculated by:

$$risk = risk_{standing} * \left(risk_{left\ side} + (1 - risk_{left\ side}) * \left(risk_{standing} + (1 - risk_{standing}) * \left(1 - \cos\left(\frac{\pi\theta}{180}\right)\right) * \sqrt{1 + \sin\left(\frac{\pi\varphi}{180}\right)}\right)\right)$$

When the user is leaning forward but not inverted (i.e. 0<theta<90) and phi is 0, the risk value may be calculated by:

$$\text{risk} = (\text{risk}_{stomach} - \text{risk}_{standing}) * \cos\left(\frac{-\pi\theta}{180}\right)$$

When the user is leaning forward but not inverted (i.e. 0<theta<90) and tilted to the left (phi is between 0 and −90), the risk value may be calculated by:

$$\text{risk} = \text{risk}_{left\ side} +$$
$$(1 - \text{risk}_{left\ side}) * \left((\text{risk}_{stomach} - \text{risk}_{standing}) * \cos\left(\frac{-\pi\theta}{180}\right)\right) * \left(1 + \sin\left(\frac{\pi\varphi}{180}\right)\right)$$

When the user is leaning forward by more than 90 degrees (i.e., 180>theta>90) and phi is 0, the risk value may be calculated by:

$$\text{risk} = \text{risk}_{stomach} + (\text{risk}_{headstand} - \text{risk}_{stomach}) * \left(-\cos\frac{\pi\theta}{180}\right) * \text{risk}_{headstand}$$

When the user is flat on their stomach (theta=90) and tilting to the left (0>phi>−90), the risk value may be calculated by:

$$\text{risk} = \text{risk}_{left\ side} + (1 - \text{risk}_{left\ side}) * \text{risk}_{stomach} * \left(1 + \sin\left(\frac{\pi\varphi}{180}\right)\right)$$

When the user is leaning forward by more than 90 degrees (i.e., 180≥theta>90) and tilting to the left (0>phi>−90), the risk value may be calculated by:

$$\text{risk} = \text{risk}_{left\ side} + (1 - \text{risk}_{left\ side}) *$$
$$\left(\text{risk}_{stomach} + (\text{risk}_{headstand} - \text{risk}_{stomach}) * \left(-\cos\frac{\pi\theta}{180}\right) * \text{risk}_{headstand}\right) *$$
$$\sqrt{1 + \sin\left(\frac{\pi\varphi}{180}\right)}$$

When the user is tilting to the right side (0>phi>90), the risk value may be the risk value at an equivalent position when tilting to the left ($\text{risk}_{left\ equivalent}$) that factors in the right side risk. For example, in the illustrated matrix, when the user is tilting to the right side (0>phi>90), the risk may be calculated by:

$$\text{risk} = \text{risk}_{left\ equivalent} + \sin\left(\frac{\pi\varphi}{180}\right)^2 * \text{risk}_{right\ side}$$

Thus, when the user is reclined backward by between −90 and −180 degrees (−90>theta>−180) and tilted to the right (0>phi>90), the risk value may be calculated by:

$$\text{risk} = \left(\text{risk}_{left\ side} + (1 - \text{risk}_{left\ side}) * \text{risk}_{-90<recline<-180} * \sqrt{1 + \sin\left(\frac{\pi\varphi}{180}\right)}\right) +$$
$$\sin\left(\frac{\pi\varphi}{180}\right)^2 * \text{risk}_{right\ side}$$

When the user is reclined backward between 0 and −90 degrees or −90 degrees (i.e., 0<theta≤−90), and tilted to the right (0>phi>90), the risk value may be calculated by:

$$\text{risk} = \left(\text{risk}_{left\ side} + \right.$$
$$(1 - \text{risk}_{left\ side}) * \left(\text{risk}_{standing} + (1 - \text{risk}_{standing}) * \left(1 - \cos\left(\frac{\pi\theta}{180}\right)\right)\right) *$$
$$\left.\sqrt{1 + \sin\left(\frac{\pi\varphi}{180}\right)}\right) + \sin\left(\frac{\pi\varphi}{180}\right)^2 * \text{risk}_{right\ side}$$

When the user is not reclined or leaning forward (i.e., theta is 0) and is tilted to the right (0>phi>90), the risk value may be calculated by:

$$\text{risk} = \left(\text{risk}_{standing} * \left(\text{risk}_{left\ side} + \right.\right.$$
$$(1 - \text{risk}_{left\ side}) * \left(\text{risk}_{standing} + (1 - \text{risk}_{standing}) * \left(1 - \cos\left(\frac{\pi\theta}{180}\right)\right)\right) *$$
$$\left.\left.\sqrt{1 + \sin\left(\frac{\pi\varphi}{180}\right)}\right)\right) + \sin\left(\frac{\pi\varphi}{180}\right)^2 * \text{risk}_{right\ side}$$

When the user is leaning forward but not inverted (i.e. 0<theta<90) and tilted to the right (0>phi>90), the risk value may be calculated by:

$$\text{risk} = \left(\text{risk}_{left\ side} + (1 - \text{risk}_{left\ side}) * \left((\text{risk}_{stomach} - \text{risk}_{standing}) * \cos\left(\frac{-\pi\theta}{180}\right)\right) *\right.$$
$$\left.\left(1 + \sin\left(\frac{\pi\varphi}{180}\right)\right)\right) + \sin\left(\frac{\pi\varphi}{180}\right)^2 * \text{risk}_{right\ side}$$

When the user is flat on their stomach (theta=90) and tilting to the right (0>phi>90), the risk value may be calculated by:

$$\text{risk} = \left(\text{risk}_{left\ side} + (1 - \text{risk}_{left\ side}) * \text{risk}_{stomach} * \left(1 + \sin\left(\frac{\pi\varphi}{180}\right)\right)\right) +$$
$$\sin\left(\frac{\pi\varphi}{180}\right)^2 * \text{risk}_{right\ side}$$

When the user is leaning forward by more than 90 degrees (i.e., 180≥theta>90) and tilting to the right (0>phi>90), the risk value may be calculated by:

$$\text{risk} =$$
$$\left(\text{risk}_{left\ side} + (1 - \text{risk}_{left\ side}) * \left(\text{risk}_{stomach} + (\text{risk}_{headstand} - \text{risk}_{stomach}) *\right.\right.$$
$$\left(-\cos\frac{\pi\theta}{180}\right) * \text{risk}_{headstand}\right) *$$

$$\sqrt{1+\sin\left(\frac{\pi\varphi}{180}\right)} + \sin\left(\frac{\pi\varphi}{180}\right)^2 * \text{risk}_{right\ side}$$

While these exemplary functions, constants, and constant values are provided, it should be understood that embodiments of the system are in no way limited to the above functions and the exemplary constants or the exemplary constant values. As stated, the orientation risk values and equations may be customized or refined upon further clinical analysis. Optionally, as discussed above, look up tables may be used to associate risk values with orientation data. Additionally, it should be understood that other risk scales may be used. The exemplary 0-1 scale is provided for example only and is non-limiting.

Thus, based on the received orientation sensor data, a determination of an orientation risk value can be made 204. A time series of orientation risk values 206 may be determined as the sensor data is received. From the time series of orientation risk values, a cumulative orientation risk value may be calculated 208. In an exemplary embodiment, the cumulative orientation risk value may be the average of the last 300 seconds of orientation risk scores. As the device receives the newest orientation risk score, it may discard the oldest, so that the most recent 300 seconds worth of orientation risk scores are always averaged to into the cumulative orientation risk value.

The cumulative orientation risk value may then be compared to an orientation risk threshold 210. In some embodiments, the orientation risk value may be compared to a first threshold and a second threshold. The first threshold may be a medium risk threshold and the second threshold may be a high risk threshold. For example, in some embodiments, the medium risk threshold may be between 0.15-0.25, preferably 0.2, and the high risk threshold may be between 0.35-0.45, preferably 0.4.

In further embodiments, a processor could use manual user data inputs and diagnostic test results in conjunction with physiological parameters to assess the risk of disease initiation. Further, the method 200 may further include receiving user data 214 to adjust or calculate one or more risk thresholds 216. For example, user attributes or pregnancy factors may increase or decrease orientation risks. In some embodiments, the data from a multitude of users could be used to create a more accurate predictive algorithm of risk based on certain physiological parameters. For example, the Overall Relative Etiological Risk (ore.risk) may be factored into medium risk and high risk thresholds to change the threshold at which alarms are triggered. The ore.risk will typically be a value between ~0.5 and 10 where 0.5 is a very low risk user, 1 is an average risk user, and 10 is a very high risk user.

So, the medium risk and high risk thresholds may be modified by the ore.risk value in order to create the new threshold alert levels. For example and etiological adjust medium risk may be calculated by:

et.adj.med.risk=med.risk/sqrt(ore.risk)

For example, a Low risk user may be not overweight, with low blood pressure, and on her $2^{nd}$ pregnancy with an ore.risk score of 0.6.

$$eti.adj.med.\text{risk} = med.\text{risk}/sqrt(ore.\text{risk}) = \frac{.2}{.78} = .26$$

In a further example, a med (average) risk user (thin, low blood pressure, $2^{nd}$ pregnancy) with an ore.risk score of 1.

$$eti.adj.med.\text{risk} = med.\text{risk}/sqrt(ore.\text{risk}) = \frac{.2}{1} = .2$$

In yet another example, High risk user (thin, low blood pressure, $2^{nd}$ pregnancy) with an ore.risk score of 9.

$$eti.adj.med.\text{risk} = med.\text{risk}/sqrt(ore.\text{risk}) = \frac{.2}{3} = .7$$

As can be seen, the medium risk threshold for the alert to be triggered gets lower as the user becomes increasingly likely to develop preeclampsia. This means they would be more frequently encouraged to lower their activity and remain in lower risk orientations.

The algorithm may take many risk factors into consideration to customize the alert threshold for each user. The output of this risk etiological algorithm ranges between ~0.5 and ~10 where 10 is most likely to develop preeclampsia. For example, a $2^{nd}$ time mother who is thin and healthy might have a score of 0.7 whereas an obese first time mother with chronic hypertension might have a score of 5.0. The Overall Relative Etiological Risk (ore.risk) may be factored into the various risks calculated by the device. The ore.risk may be calculated my multiplying all the relative exemplary risks together in the exemplary table illustrated in FIG. 12. The list of factors is exemplary and further the proposed values are non-limiting. Table 1 illustrates a chart which may be used to inform the user what their risk level is for preeclampsia.

| Low Risk | 0 to .8 | You have a preeclampsia risk less than the average woman |
|---|---|---|
| Medium Risk | .81 to 1.5 | You have an average risk of preeclampsia |
| High Risk | 1.51 to 3 | You have an elevated risk of preeclampsia |
| Very High Risk | 3.1 and higher | You have a very high risk of preeclampsia |

In many embodiments a user interface of the device may receive input from the user of these pregnancy factors. Examples of pregnancy factors include, but are not limited to, maternal age, height, weight, blood pressure, blood oxygen, amount of leg swelling, and due date. A software application may ask the user to input a given pregnancy factor, could then use the factor to customize the processor algorithm.

Accordingly, in certain implementations, a wearable device system for identifying and/or reducing health risks is provided, the wearable device is given having one or more sensors configured for transmission and receiving of signal data and a signal processor configured to receive signal data from the sensor and to process the information, wherein the signal processor is programmed to identify sleep disordered breathing as a physiological parameter and generate a time-series of $1^{st}$ risk scores based on the characteristics of the sleep disordered breathing; generate a time-series of $2^{nd}$ risk scores which are based on multiple $1^{st}$ risk scores over time; and, generate an alert when the $2^{nd}$ risk score crosses a specified threshold value. It is understood that the other physiological and psychological parameters discussed herein can be similarly assessed for risk scores.

Figure 10C:
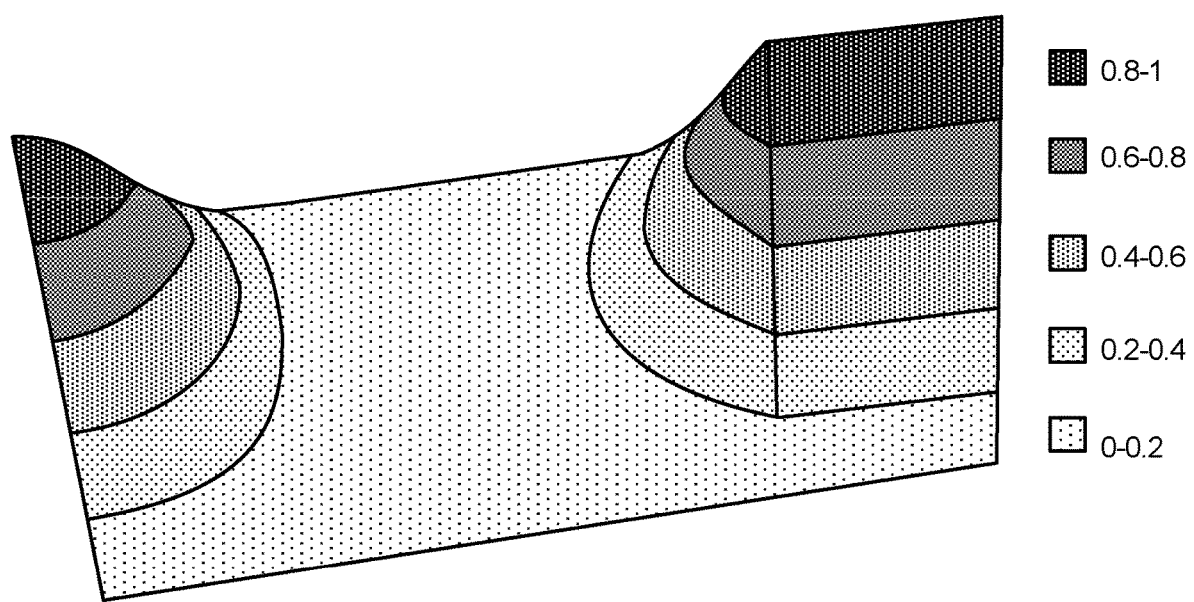
FIG. 10C illustrates a graph of representative risk scores for a variety of positions.

Optionally, the factors may be taken into account by adjusting one or more of the risk constants in the orientation risk algorithm. For example, FIG. 10B illustrates an alternative adjusted or customized preeclampsia matrix of orientation risk values for users with incompetent cervix. In the exemplary matrix in FIG. 10B uses the same underlying functions of FIG. 10A, but one or more of the six risk constants may be adjusted. Cervical incompetence is a medical condition in which a pregnant woman's cervix begins to dilate and efface before her pregnancy has reached term. Accordingly, it may be beneficial for persons diagnosed with incompetent cervix to limit the amount of standing. Thus, the standing upright risk constant may be adjusted higher (e.g., to 0.5) compared to the standing upright risk constant of FIG. 10A to adjust or customize the matrix of risk values specific to the needs of the user. FIG. 10C depicts a model graph, showing risk scores in specific positions, where the risk scores are shown on the Z-axis, and the x- and y-axis represent model theta and phi, respectively.

In some embodiments, risk values or risk thresholds could be adjusted to account for various other risk factors as well. For example, a position risk coefficient for gestational age may be provided. For pregnant users, different positions may become riskier the later in gestation, so the following formula may be used for calculating a position risk coefficient to generate a gestational age modified instant activity risk score (gam.inst.risk.act) (or a modify an associated threshold), where gestational age is in weeks.

$$\text{Position Risk Coefficient}_{gest.age} = \frac{\tanh\left(\frac{gest.\text{age} - 10}{5}\right)}{2} + 0.5$$

Figure 16:
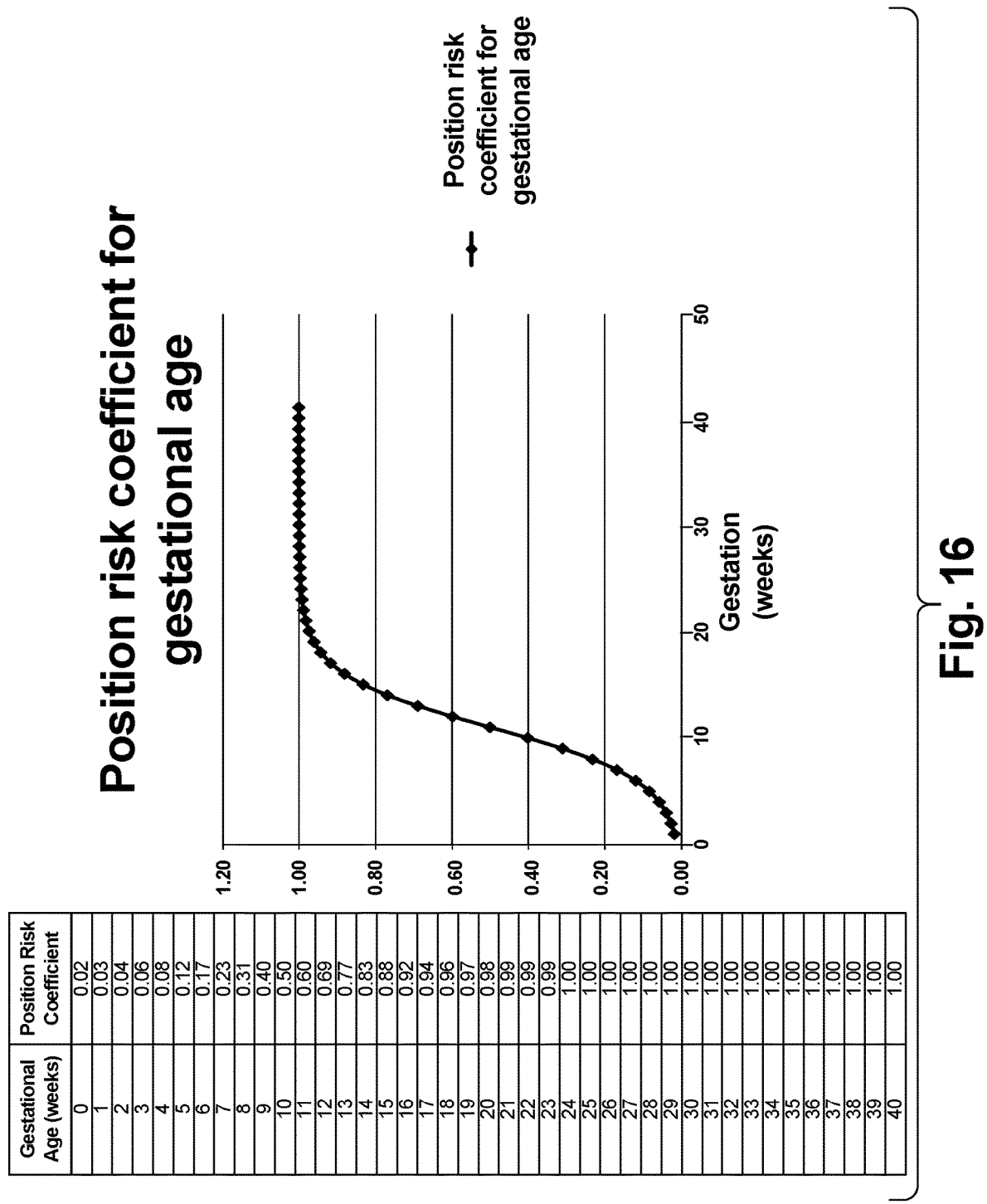
FIG. 16 illustrates a table and plot illustrating the exemplary relationship between risk coefficients and gestational age.

FIG. 16 illustrates a table and plot showing the exemplary relationship between risk coefficients and gestational age. This gestational age modifier algorithm is exemplary. As this is only applicable to pregnant users, this modifier may be turned off or on by the user. Other factors may be weighed as such as obesity, diabetes, multiple pregnancy, blood pressure, body mass index, etc. Other factors that may affect the threshold risk value are discussed further below.

Figure 11:
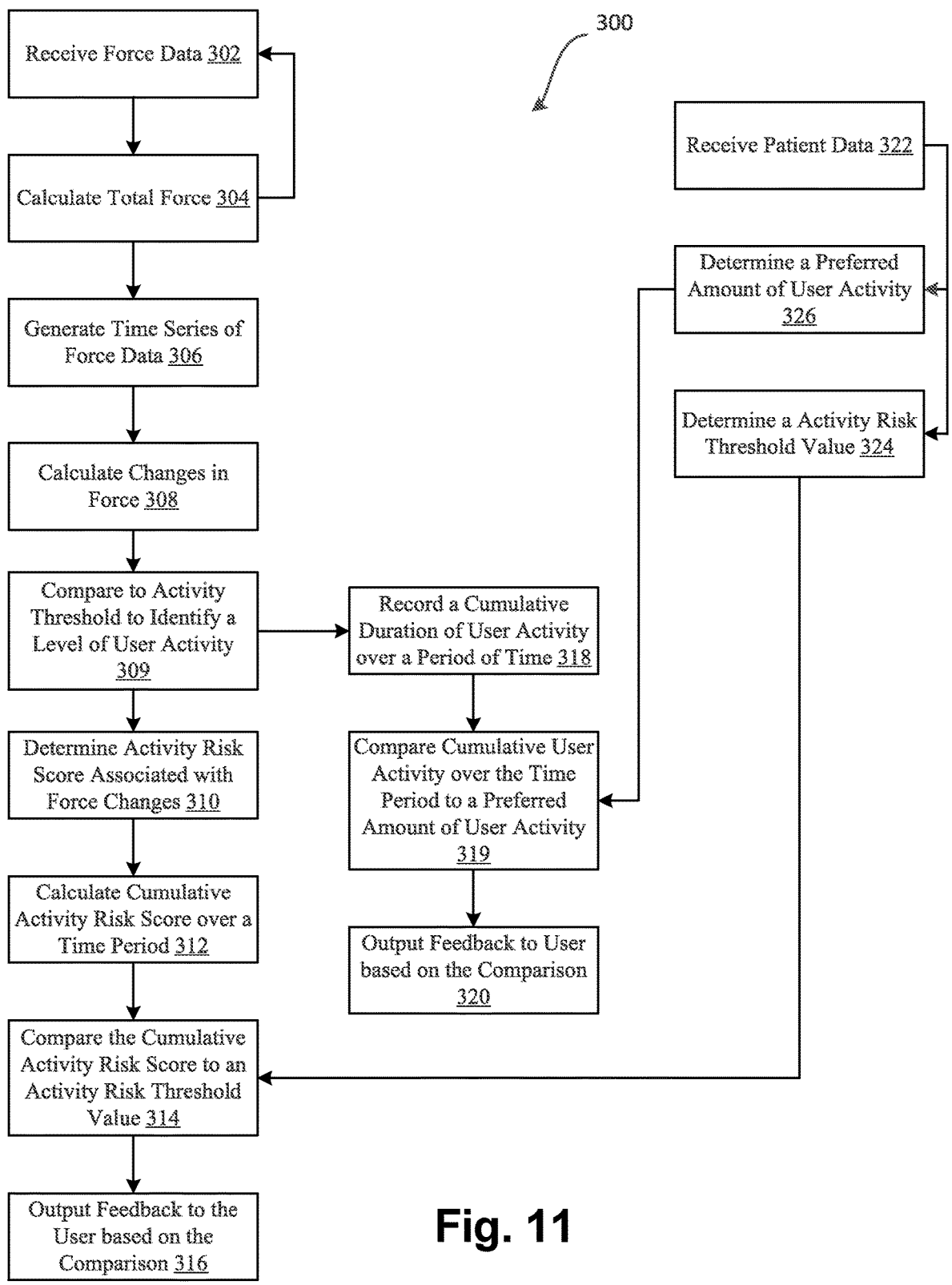
FIG. 11 illustrates an exemplary method for monitoring activity risks.

FIG. 11 illustrates an exemplary method 300 for monitoring activity risks. At step 302 force data is received. The total force experienced by the user may be determined from the received force data 304. A time series of force data may be generated 306. Changes in force may be determined using the time series of force data 308. The changes in force may be compared to an activity threshold to determine whether the user is engaged in a clinically significant level of activity 309.

To monitor activity risks, an activity risk score may be associated with the calculated force changes 310. A cumulative activity risk score may be calculated 312. The cumulative activity risk score may be compared to an activity risk threshold value 314. Based on the comparison, a feedback may be outputted to the user 316. Additionally, a duration of the user activity may be recorded for a period of time 318. A cumulative duration of the user activity over the entire time period may be compared to a preferred amount of user activity 319. Based on the comparison, a feedback may be outputted to the user 320.

Similar to the orientation monitoring method described above, user data may be received 322 and the user data may be used to adjust or calculate the activity risk threshold value 324. Further, the user data may be used to adjust or calculate the preferred amount of user activity 326. The customized activity risk threshold value 324 may be fed into step 314 for comparison to the cumulative activity risk score. The customized preferred amount of user activity 326 may be fed into step 319 for comparison to the cumulative user activity over the time period.

In some embodiments, the activity risk may be evaluated based on vigorousness rather than by activity type. Vigorousness may be depended on the delta in g-force at any point in time. As discussed above, the received force data may be $F_x$, $F_y$, $F_z$ force data. In some embodiments, the force data may be received at a frequency between 0.5-50 Hz and the received data may be placed into memory for further analysis. Preferably, the data is received at least at a frequency of 10 Hz. The total force experienced by the user may be determined from the received force data 304 by adding the absolute values of $F_x$, $F_y$, and $F_z$ to generate total g-force.

A time series of force data may be generated 306 and changes in force may be determined using the time series of force data 308. For example, a subset of the time series of force data may be defined and the minimum and maximum values may be extracted from the subset to calculate the force change. For example, a subset may include increments of 15 force values. The changes in force may then be compared to an activity threshold to determine whether the user is engaged in a clinically significant level of activity 309.

For example, where the force data is received every 0.1 seconds, the force change may be calculated every 1.5 seconds to determine if activity is still occurring and if so, what level of vigorousness. The average g-force when not moving will be ~1. For the exemplary algorithm, if the total g-force regularly fluctuates from 0.75 to about 1.25 (or a delta of 0.5), over any 1.5 second span, the algorithm may determine that the user is engaged in clinically significant activity. In some embodiments, a number of thresholds may be used to identify different levels of activity. For example, when force changes=0-0.3, the algorithm may determine that the user is not engaged in activity. When the force changes=0.3-0.75, the algorithm may determine that the user is engaged in low activity. When the force changes=0.75-1.25, the algorithm may determine that the user is engaged in medium activity. When the force changes=1.25-2, the algorithm may determine that the user is engaged in high activity. When the force changes >2, the algorithm may determine that the user is engaged in dangerous activity. These values for vigorousness levels are exemplary.

To monitor activity risks, an activity risk score may be associated with the calculated force changes 310. An example activity risk algorithm may provide a relatively low risk at low force changes (e.g., g-force change <0.5) but may then sharply increase and as force changes grows to 2 and higher the activity risk score may asymptote to 1. An exemplary activity risk algorithm may be:

$$\text{activity risk} = \frac{-0.5}{(\Delta \text{force} + 0.1)^{1.25}} + 1$$

This activity risk algorithm is exemplary and non-limiting.

A cumulative activity risk score may be calculated 312. The cumulative activity risk value may be a moving average of the risk scores. For example, the cumulative activity risk value may be the average of a subset of the time series of activity risk values (e.g., the last 30 seconds—the last 1000 seconds of activity risk values). In one embodiment, the cumulative activity risk value may be the average of the last 300 seconds of activity risk scores. As the device receives the newest activity risk score, it may discard the oldest, so that the most recent 300 seconds worth of activity risk scores are always averaged to into the cumulative activity risk value.

The cumulative activity risk score may be compared to an activity risk threshold value 314. In some embodiments, the activity risk value may be compared to a first threshold and a second threshold. The first threshold may be a medium risk threshold and the second threshold may be a high risk threshold. For example, in some embodiments, the medium risk threshold may be between 0.15-0.25, preferably 0.2, and the high risk threshold may be between 0.35-0.45, preferably 0.4.

The duration of the user activity may be recorded for a time period 318. The time period may be a day, two days, a week, two weeks or the like. In some embodiments, it may be preferable to record a cumulative duration of user activity over the course of a week. The cumulative duration of the user activity over the entire time period may be compared to a preferred amount of user activity 319. Based on the comparison, a feedback may be outputted to the user 320.

In some embodiments, user data may be received 322 and the user data may be used to adjust or calculate the activity risk threshold value 324 or to adjust an instant activity risk score. For example, the activity risk algorithm may be adjusted to factor in a gestation age. For pregnant users, exercise may become riskier the later in gestation, so the following formula may be used for calculating an activity risk coefficient to generate a gestational age modified instant activity risk score (gam.inst.risk.act), where gestational age is in weeks.

$$gam.inst.risk.act \frac{\tanh\left(\frac{gest.\text{age} - 20}{5}\right)}{2} + 0.5$$

This gestational age modifier algorithm is exemplary. As this is only applicable to pregnant users, this modifier may be turned off or on by the user. Other factors may be weighed as such as obesity, diabetes, multiple pregnancy, blood pressure, body mass index, etc. Other factors that may affect the threshold risk value are discussed further below.

Further, the user data may be used to adjust or calculate the preferred amount of user activity 326. For example, in some embodiments where the device is used to monitor pregnant user activity, an age of gestation may be factored in to calculate or determine the preferred amount of user activity. For example, early pregnancy (e.g., before 20 weeks of gestation) may have a different preferred amount of user activity compared to a preferred amount of user activity during late pregnancy (e.g., after 30 weeks of gestation). In some embodiments, 4 hours or less of intense physical activity per week before 20 weeks may be recommended. Additionally, 2 hours or less of intense physical activity per week may be recommended for pregnant women between 21-30 weeks. After 30 weeks, the device may be configured to discourage any intense activity.

In some embodiments, the algorithm may discourage long durations of moderate activities and short durations of vigorous activities. In some embodiments, the feedback may be configured to encourage certain low level activities like slow walking and may discourage more vigorous ones like running. Advantageously, the activity monitor may remind users to take breaks throughout the day based on a schedule and/or based on the level of activity experienced to that point that day.

Optionally, the algorithm may have set adjustments to conform to various desired physiological parameters. For example, the algorithm may be preprogramed to be switchable between modified activity monitoring, scheduled rest monitoring, bed rest monitoring, and/or hospital bed rest.

In some embodiments, the time series of orientation risk scores may be combined with the time series of activity risk scores to generate a continuous time series of risk values 111. For many embodiments, the device may generate either an activity risk score or an orientation risk score throughout the day (e.g., every second or more) to provide a continuous series of activity and orientation risk scores.

This time series of risk scores may then be used to calculate a cumulative daily risk score 112. For example, in some embodiments, the daily score may start at 100 and drop by an amount equal to $1/(60\ s*60\ min*Hours_{day})*100*$"instant risk score" every second of the day. The cumulative daily risk score equation is exemplary and non-limiting. The equation may be tuned to revise/update the cumulative daily score more frequently (e.g., every tenth of a second, every half a second, etc.) or less frequently (e.g., every two seconds, every five seconds, etc.).

The $Hours_{day}$ variable is the time duration over which the cumulative daily score is calculated. In some embodiments, the $Hours_{day}$ variable may be between 14-24 hrs, preferably 24 hrs. When the 24 hr duration is used, the device may be programmed to start recording the cumulative daily risk value at 1:00-5:00 AM in the time zone of the user.

After the cumulative daily health score is calculated, the score may be compared to a daily risk threshold. In some embodiments, a low risk user may aim to stay above 80, a higher risk user may aim to stay above 90 and a user prescribed bed rest (for example) may aim to stay above 95. These thresholds are exemplary and non-limiting. In many embodiments the daily risk thresholds may be raised or lowered or otherwise customized for a user based on user factors.

The continuous time series of risk scores may also be used to calculate a combined moving average risk score 113. Similar to the other cumulative risk scores, the combined moving average risk value may be the average of a subset of the continuous time series of activity risk values and orientation risk values combined (e.g., the last 30 seconds–the last 1000 seconds of activity risk values). In an exemplary embodiment, the combined moving average risk value may be the average of the last 300 seconds of activity risk scores and orientation risk scores. As the device receives the newest activity risk score or orientation risk score, it may discard the oldest score, so that the most recent 300 seconds worth of activity risk scores and/or orientation risk scores are always averaged into the combined moving average risk value.

The combined moving average risk score may be compared to a combined moving average risk threshold value. In some embodiments, the combined moving average risk value may be compared to a first threshold and a second threshold. The first threshold may be a medium risk threshold and the second threshold may be a high risk threshold. For example, in some embodiments, the medium risk threshold may be between 0.15-0.25, preferably 0.2, and the high risk threshold may be between 0.35-0.45, preferably 0.4.

When monitoring the orientation, activity, or a combination of the two, the device may utilize multiple cumulative orientation risk values, cumulative activity risk values and/or combined moving average risk values. Accordingly, in some embodiments, the device may calculate two, three, four, or more cumulative orientation risk values and may separately calculate two, three, four, or more cumulative activity risk values. Similarly, two, three, four, or more combined moving averages may be calculated. For example, the device may employ cumulative scores over multiple lengths of time (e.g., last 2 minutes, last 5 minutes, last 15 minutes, etc.). Further each of the cumulative values may be associated with a different threshold clinical value tolerance before an alert is generated.

The sensor data from a plurality of devices may be gathered and the thresholds and algorithms may be further refined. Accordingly, in some embodiments, the system may become more accurate and precise over time as it collects user data and refines the algorithms and threshold values. In some embodiments, the different positions may be subdivided into different groups for a regression analysis to compare time spent in each of those positions to age of gestation at birth.

Various implementations of the system comprise a user feedback mechanism. FIG. 13 illustrates an exemplary user interface 400 for orientation risk monitoring according to some embodiments. User interface 400 may include a 3D CAD image 402. The 3D CAD image may constantly rotate to mirror the user's orientation. The user interface 400 may further include a real time position risk meter 404. A cumulative orientation risk value or a combined moving average risk meter 406 may also be displayed. A daily compliance meter 408 may also be provided. The daily compliance meter 408 may operate like a fuel-gauge—it may start at full and drop throughout the day.

When the device 10 detects activity it may switch from the orientation user interface 400 to the activity monitoring user interface 500 illustrated in FIG. 14. Similarly, when the device ceases to detect activity, it may switch from the activity monitoring user interface 500 to the orientation monitoring user interface 400. Optionally, both interfaces 400, 500 may be displayed to the user with an indication as to which one is active or passive (e.g., highlighted, dimmed, etc.).

User interface 500 may illustrate an activity icon 502. The activity icon 502 may be representative of a running person. As activity score increases, the icon 502 may be displayed as running at a faster speed. The user interface 500 may further include a real time activity risk meter 504. Similar to user interface 400, user interface 500 may also include a cumulative activity risk meter or a combined moving average risk meter 506. The daily compliance meter 508 may also be provide on the user interface 500.

In some embodiments, the bottom two meters on user interface 400 and user interface 500 may be the same. In such configurations, the top half of the screen may automatically switch between activity 504 and position risk 404 meters depending upon whether or not activity is detected.

In one implementation, the device may provide some or all of the following menu hierarchy:
User Information
    Email
    Due date
    First name
    Last name
    Doctor email
    Maternal birth date
    Any prior live births? [y/n]
    Twins or more currently in utero? [y/n]
    Preexisting hypertension (high blood pressure)? [y/n]
    Height [feet and inches]
    Weight [lbs]
    Diabetes Mellitus? [y/n]
    Highest Maternal Education Level
        None
        Elementary
        Middle and/or high school
        College
    Currently living with baby's father [y/n]
    Previous Abortion [y/n]
    Cigarette smoking
        No
        1-9 cigarettes per day
        10 or more cigarettes per day
    Fetal malformation [y/n]
Training Mode
Share Data
    Email recipients:
    Email user [checkbox](change user email)
    Email doctor [checkbox] (change doctor email)
    Email other [enter email address]
    All Data [checkbox] or Date Range [enter 2 dates]
Contact Smart Human Dynamics
    San Francisco, Calif. based Smart Human Dynamics, Inc can be reached at [email address]
Advanced Options
    Modify algorithms by gestational age [on/off]
    Modify algorithms by etiological factors [on/off]
    Medium level alert [choose value 0 to 1 with 0.2 as default]
    High level alert [choose value 0 to 1 with 0.4 as default]
    Calibration sensitivity [choose value 0 to 1 with 0.02 as default]
    Temporary Risk Estimator [0 to 1; to 2 decimal places]
Calibrate Device The software may be configured to email the following sets of data on separate pages of an electronic spreadsheet document (such as, for example, an Excel® spreadsheet):
    Total time app was used, % of time activity was sensed, and Daily Cumulative risk score [final score of the day; 1 data point per day for each of these 3 scores]
    Daily cumulative risk score on a running basis [numerous points per day at 10 min intervals; e.g. a total of 60 points if device was used 10 hrs in one day]
    Moving average risk score [data points at 2 min intervals; e.g., total of 300 data points for one 10 hour day]
    Instant Position risk score and Instant Activity risk score [essentially, all the raw data at 1 sec intervals]

All days of data may be combined onto one page (workbook sheet) for each of the 4 data types for a total of 4 pages of data.

Figure 15:
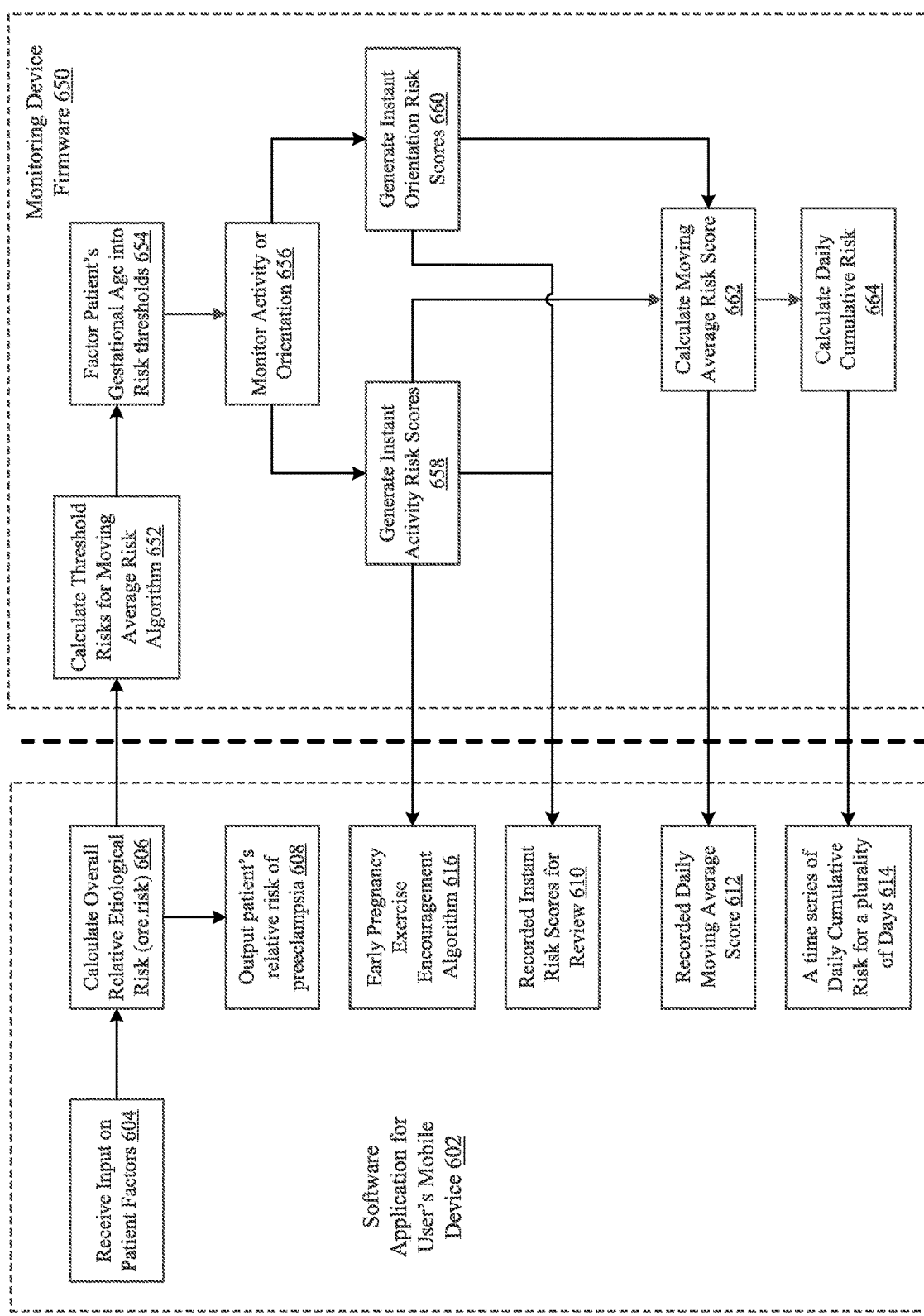
FIG. 15 illustrates another exemplary method according to some embodiments.

FIG. 15 illustrates another exemplary method and system 600 according to some embodiments. In the illustrated system 600, a software application 602 may be loaded onto the user's personal mobile device. The user's mobile device may be a portable electronics device such as, a smartphone, table computer, PDA, smartwatch, or related device. The software application 602 may receive input on user risk factors 604. The software application 602 may calculate overall relative etiological risk (ore.risk) 606 using the user inputted user factors 604. The relative etiological risk (e.g., a value ranging from 0.5 to 10, for example) may be calculated from a formula in the software 602 that is based on regression analysis of known risk factors. The software application 602 may then output the user's relative risk of preeclampsia 608 (e.g., output to a display on the mobile device). The relative risk may be identified using the thresholds and categories in Table 1, for example.

Thereafter the software 602 may send the ore/risk to the monitoring device firmware 650. The device firmware 650 may revise default threshold values to factor in ore.risk 652 to provide the etiological adjusted medium risk and etiological adjusted high risk. For example, if med.risk=0.2; high.risk=0.4; and ore.risk=2.1 then:

et.adj.med.risk=med.risk/sqrt(ore.risk)=0.14 eti.adj.high.risk=high.risk/sqrt(ore.risk)=0.28

Thereafter, a user's gestation age (gest.age) may be factored into the risk thresholds 654. Continuing with the above example, if gest.age=27 (weeks), then:

$$gest.adj.med.\text{risk} = eti.adj.med.\text{risk} * \left( \frac{\text{TANH}\left(\frac{gest.\text{age} - 20}{5}\right)}{2} + 0.5 \right) = 0.13$$

$$gest.adj.\text{high.risk} = eti.adj.\text{high.risk} * \left( \frac{\text{TANH}\left(\frac{gest.\text{age} - 20}{5}\right)}{2} + 0.5 \right) = 0.26$$

The device firmware 650 may then monitor activity, orientation, or other physiological parameters 656 using the customized thresholds. Instant activity risk scores may be produced 658. The instant activity risk scores may be associated with a vigorousness level of activity. Instant orientation risk scores may be produced 660. Often, the risk scores are produced to generate a time series of risk scores.

These risk scores may be combined and fed into the moving average risk score 662 where the algorithm calculates whether risk score is above the gest.adj.med.risk or gest.adj.high.risk thresholds and alerts the user as appropriate. Further a Daily Cumulative Risk may be calculated using the combined time series of risk scores 664.

Optionally, the instant activity and instant orientation risk scores may be transmitted back to the user's mobile device for storage and/or analysis 610. For example, the software application 602 may display a meter bar graph corresponding to the instant risk score. The meter bar graph may, for example, display the instant risk scores for the entire day averaged at one minute intervals. The software application 602 may also allow user may access this information to provide the user more detail about the instant risk score.

The moving average risk score may also be transmitted back to the user's mobile device for storage and/or analysis 612. The software 602 may allow the user to access this information to provide the user more detail about the moving average risk score. The software 620 may also be configured to display a bar graph corresponding to the moving average risk scores. For example, the bar graph may display all the moving average risk scores for the entire day averaged at one minute intervals.

As shown in FIG. 15, the daily cumulative risk may also be transmitted back to the user's mobile device for storage and/or analysis 614. The software 602 may maintain a history of daily cumulative risk for all days. The software 602 may also be configured to display a bar graph with all the daily cumulative risk bars for all days of the pregnancy. A color of each bar may correspond to the level or risk.

Further, in some embodiments, the instant activity risk score may be transmitted to the user's mobile device for further analysis 616. For example, an early pregnancy exercise encouragement algorithm may be provided 616. For users in their early stages of pregnancy (e.g., 15 weeks) a certain amount of vigorous activity may be beneficial and encouraged by the software 602. The preferred level of vigorous activity may trail off at 15 weeks and may get progressively more restrictive beyond 15 weeks. A meter may display the cumulative number of minutes of vigorous exercise each day with the target minutes listed as well.

Figure 17:
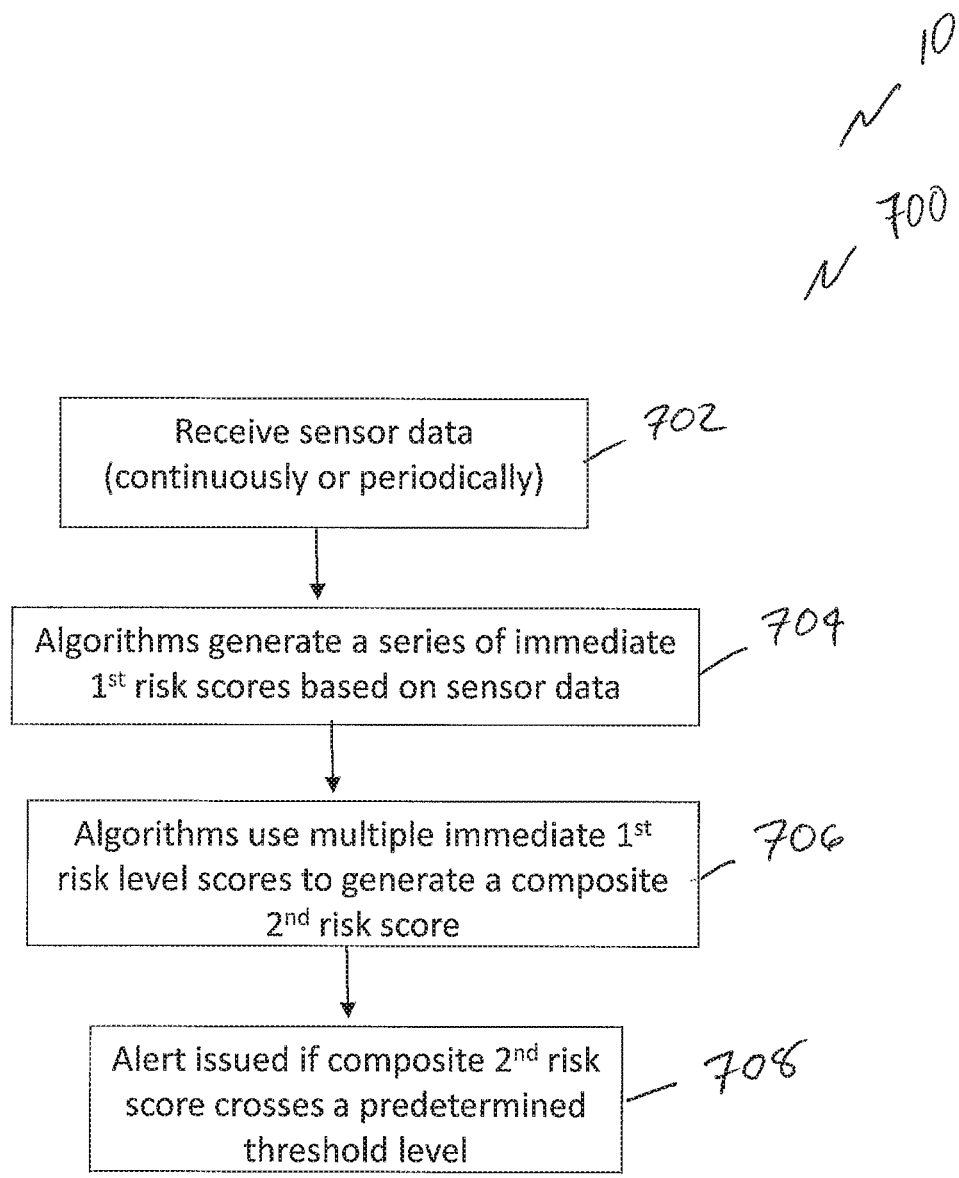
FIG. 17 is a flow chart of one algorithm implementation.
Figure 18:
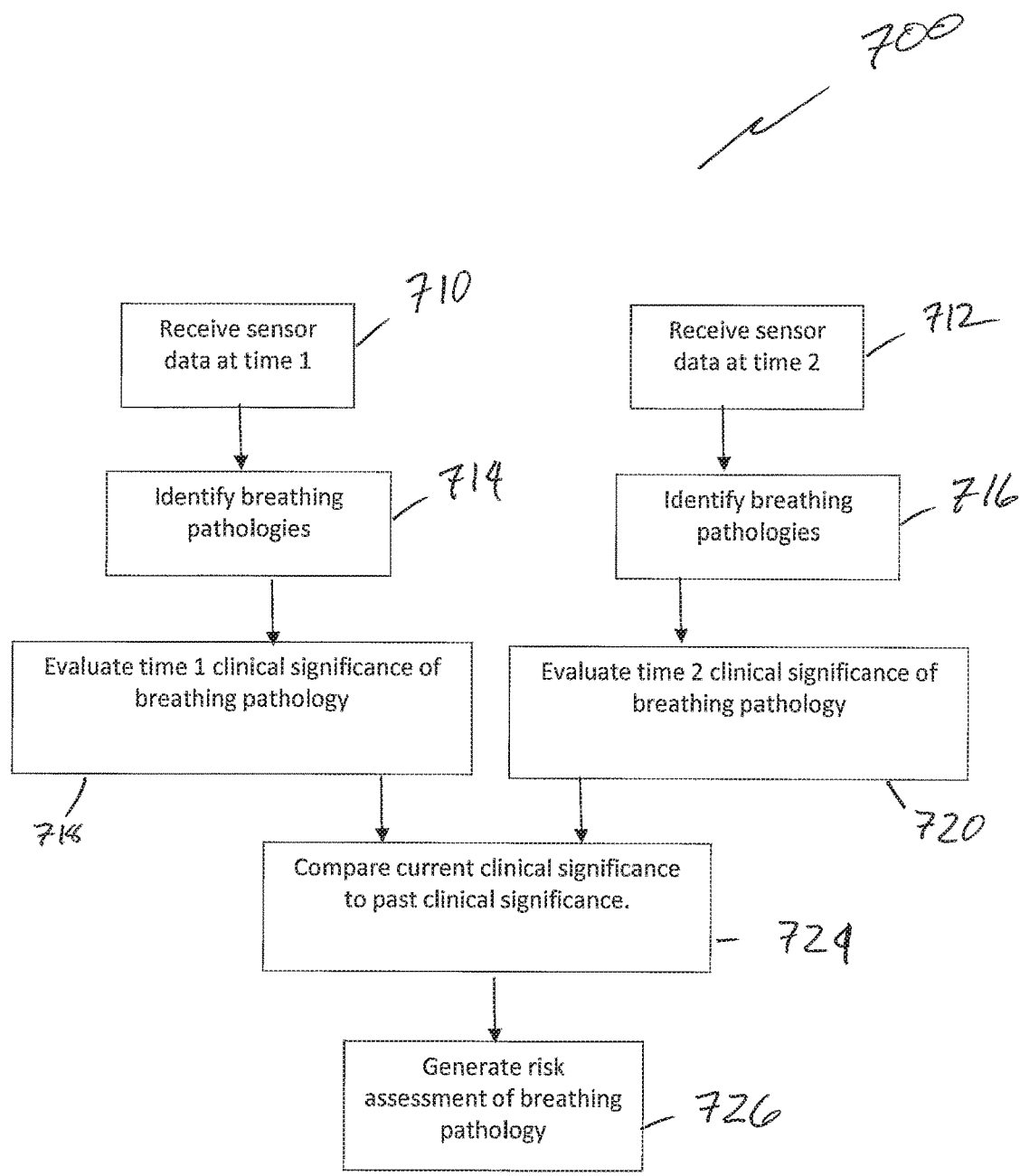
FIG. 18 is a flow chart of another algorithm implementation.
Figure 19:
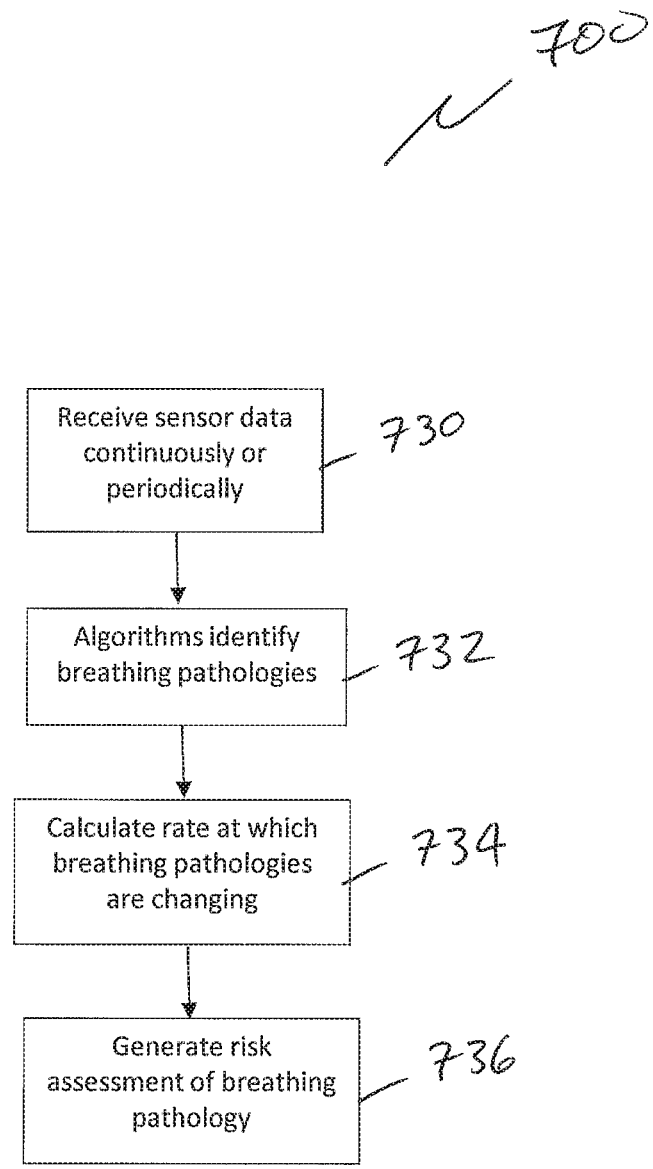
FIG. 19 is a flow chart of a further algorithm implementation.

As shown in FIGS. 17-19, in certain embodiments, the sensor data is analyzed over days, weeks or months to capture the dynamic changes in sleep disordered breathing rather than the absolute values. In one embodiment, risk scores or alerts are generated when either the changes become significant, the absolute values become significant, or a combination of both. In one example, the absolute snoring values may not reach a critical threshold level; however, since they have increased dramatically from the original values, a warning may be generated. In some conditions, especially pregnancy, sleep disordered breathing prevalence increases dramatically compared to pre-pregnancy levels. In one embodiment, the system analyzes the change in sleep disordered breathing levels in order to identify patients that are likely to soon cross the critical threshold level that is considered clinically significant and requires some intervention. In another embodiment, the system compares sleep disordered breathing values to a large group of pregnant women to determine appropriate threshold levels for any given age of gestation or other patient characteristics.

As shown in FIG. 17, in certain implementations, the device 10 and algorithm 700 are configured to receive sensor data 702 an identify segments of time when the user is engaged in an unhealthy behavior. In these embodiments, the algorithm is configured to generate a time-series of $1^{st}$ risk scores based on the sensor data 704, generate a time-series of $2^{nd}$ risk scores which are based on multiple $1^{st}$ risk scores over time 706; and, generate an alert when the $2^{nd}$ risk score crosses a specified threshold value 708.

Accordingly, the system 1 generates a cumulative nighttime risk score wherein the score increases only after the user is in a dangerous position for a certain threshold period of time. In a further embodiment, the risk accumulation rate increases the longer the user is in the dangerous position.

As shown in FIG. 18, in certain implementations, the algorithm 700 can receive sensor data at a first time (box 710) and second time (box 712), identify breathing pathologies at those times (boxes 714 and 716, respectively) and evaluate each for clinical significance (boxes 718 and 720). These significance, or risk scores, can be compared with past clinical significance (box 724) and a risk assessment can be generated (box 726).

In further implementations of the algorithm 700, and as shown in FIG. 19, sensor data can be received by the processor and analyzed by the algorithm continuously or periodically (box 730). In either event, the algorithm can identify breathing pathology (box 732), calculate the rate of change (box 734) and generate a risk score or assessment on the basis of this change in pathology (box 736).

Figure 20:
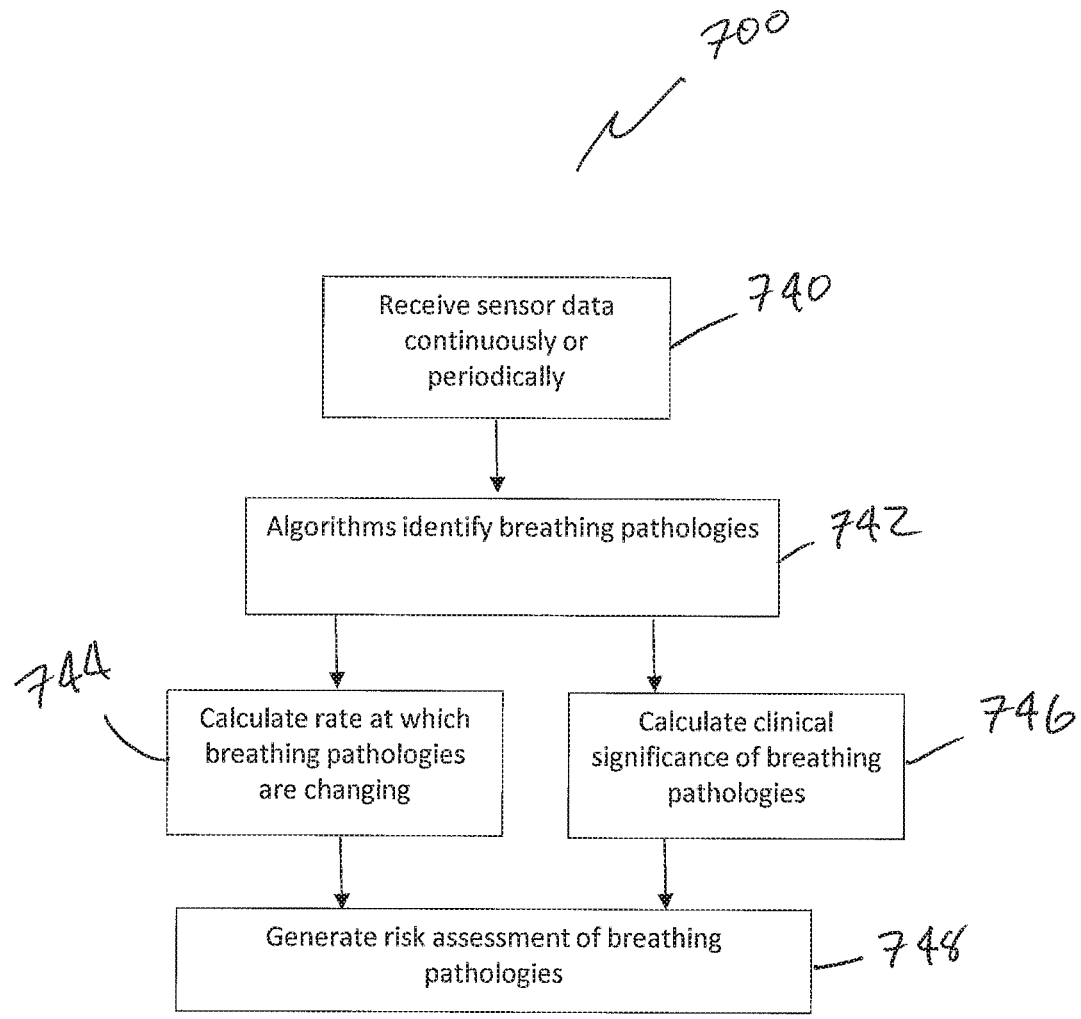
FIG. 20 is a flow chart of yet another algorithm implementation.

In FIG. 20, sensor data can be received by the processor and analyzed by the algorithm continuously or periodically (box 740). In either event, the algorithm can identify breathing pathology (box 742), calculate the rate of change (box 744) and simultaneously calculate the significance of breathing pathology (box 746) and generate a risk score or assessment on the basis of this change in pathology (box 748). As would be understood, these various approaches can be applied to any of the physiological parameters discussed herein.

In one embodiment, if a user frequently goes into dangerous positions but for only short periods of time, the score doesn't accumulate very significantly; however, if the user spends the same total amount of time in dangerous positions, but does so in long individual segments, the risk score generated is higher. In one example, over the course of one night's sleep, a user goes into the supine position 10 different times for 5 min each time with 5 min gaps in-between where the user is on her left side. In this example, a total risk score of 22 out of a max 100 is generated. In a second example, a user goes into the supine position 1 time for 50 min. In this second example, a total risk score of 71 out of a max 100 is generated. In these two examples, the user spent the same cumulative amount of time supine during a given night; however the user who had frequent breaks between the supine position generated a much lower risk score. One reason why a method of scoring like this would be useful is in the case of a pregnant women who completely occludes her IVC with her gravid uterus each time she is supine. The restriction in flow to her placenta and fetus could be much more damaging if flow blood flow was restricted over a long period of time compared to intermittent restriction.

In certain implementations, the device 10 and algorithm are configured to identify segments of time when the user is engaged in an unhealthy behavior, apply a formula to this period of time to create a risk value; add all risk values together to generate a second risk value. Accordingly, in certain implementations, a wearable device system for identifying and/or reducing health risks, the wearable device is given having one or more sensors configured for transmission and receiving of signal data; and a signal processor configured to receive signal data from the sensor and to process the information, wherein the signal processor is programmed to identify sleep disordered breathing; generate a time-series of $1^{st}$ risk scores based on the characteristics of the sleep disordered breathing, generate a time-series of $2^{nd}$ risk scores which are based on multiple $1^{st}$ risk scores over time; and, generate an alert when the $2^{nd}$ risk score crosses a specified threshold value.

As shown in FIGS. 17-19, in certain embodiments, the signal data is analyzed over days, weeks or months to capture the dynamic changes in sleep disordered breathing rather than the absolute values. In one embodiment, risk scores or alerts are generated when either the changes become significant, the absolute values become significant, or a combination of both. In one example, the absolute snoring values may not reach a critical threshold level; however, since they have increased dramatically from the original values, a warning may be generated. In some conditions, especially pregnancy, sleep disordered breathing prevalence increases dramatically compared to pre-pregnancy levels. In one embodiment, the system analyzes the change in sleep disordered breathing levels in order to identify users that are likely to soon cross the critical threshold level that is considered clinically significant and requires some intervention. In another embodiment, the system compares sleep disordered breathing values to a large group of pregnant women to determine appropriate threshold levels for any given age of gestation or other user characteristics.

In one embodiment, the sensor data is analyzed to determine whether or not the user should undergo a more extensive sleep study such as an in a user sleep clinic.

In one embodiment an ECG sensor is added to the system to identify fetal activity. In one embodiment, this additional data stream further helps to identify clinically significant levels of sleep disordered breathing in pregnant women that are directly impacting fetal wellbeing.

In one embodiment, the snoring detection is not active when the accelerometer registers significant movement. In one example, the snoring detection is temporarily paused when the accelerometer identifies that the user is moving around in their bed which may cause rustling sounds that are difficult to differentiate from snoring sounds.

In one embodiment, the device is connected to a mobile phone wirelessly (BLE for example) and it signals the phone to ring in order to alert the user if sleep position or sleep apnea scores are too far out of range.

In one embodiment, the system prevents episodes of SDB via vibrational alerts.

In one embodiment, the system issues recommendations to users the next morning when they wake up or before they go to sleep.

In one embodiment, the system identifies the likelihood of the user developing sleep disordered brathing based on the position of a given user and how that position correlates to sleep disordered breathing based on past user data.

In one embodiment, the system has an arterial oxygen saturation ("SpO$_2$") sensor that can be used when needed. In one embodiment, the system reminds the user to activate SpO$_2$ functionality only on certain nights depending upon on the accelerometer, microphone, and SpO2 results over the past days/weeks/months. In one embodiment, a user may have multiple previous sleep sessions where their SpO$_2$ levels are very good and they also snore very infrequently; therefore the system would not recommend that they use the SpO$_2$ attachment on a given night. Conversely, in another embodiment, if the system sensed low SpO$_2$ levels and significant snoring many nights in a row, the system may recommend that the user use the SpO$_2$ sensor on a given night.

In some embodiments, the device may include a training system which teaches the user which orientations or activities are considered risky. For example, in training mode, the device buzzes once when the user enters a position of risk level 0.2 to 0.39, buzzes twice for risk level 0.4 to 0.59, buzzes 3 times for risk level 0.6 to 0.79, and buzzes continuously for risk level 0.8 to 1.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

In various implementations, the fetal activity can include measurement of the fetal heart rate, the movement of the fetus, including kicks, body movements, rotation, and movements relative to maternal structures. In these embodiments, the fetal activity risk score can include an assessment of how fetal movement occurs over a period of time compared with a threshold or baseline.

In various implementations, the signal processor does the following: identifies at least two waveform patterns from the reflected signals, wherein a first waveform corresponds to a first maternal anatomical structure and a second waveform corresponds to a first fetal anatomical structure; identifies the first maternal anatomical structure and the first fetal anatomical structure based on pattern recognition of the first waveform and the second waveform; and extracts from the reflected signals various indicators of fetal heath and maternal health based on the determination of at least two waveform patterns and the identification of the maternal anatomical structure and the fetal anatomical structure.

In various implementations, the fetal monitoring system determines the orientation of the pregnant abdomen; each orientation is assigned a different risk category; an alert is issued when the risk crosses a threshold value.

In further implementations, the fetal monitoring system comprising a minimum of a sensor and processor; wherein data from the sensor is interpreted by an algorithm in the processor to generate a risk score; an alert is issued when the risk score crosses a threshold value.

A fetal monitoring system with one or more sensors for generating sensor data, configured to: identify risk values associated with the sensor data to produce a time series of identified risk values; and calculate and update a cumulative risk value by calculating a moving average for a subset of the time series of identified risk values associated with the sensor data, compare the cumulative risk value to a threshold; and output a warning when the cumulative risk value crosses the first threshold.

In one embodiment, the device that is described by the above claims is a small wearable device that is placed on the abdominal skin with an adhesive. The device uses a UWB sensor and a processor to continuously or periodically sense the frequency and size of fetal movements. The risk score formula takes into consideration both the frequency and intensity of fetal movements, so if the fetus moves frequently but none of the movements are significantly large the alert is triggered. Or, if the movements are large but they don't happen frequently, the alarm is triggered. If however the movements are significantly large and significantly frequent, then the alarm is not triggered.

Certain implementations of the system therefore have a wearable device system for reducing risks associated with pregnancy, the wearable device comprising a UWB sensor configured for transmission and receiving of signal data, the sensor comprising at least one antenna; and a signal processor configured to receive signal data from the sensor and to process the information, wherein the signal processor is programmed to identify fetal activity. In these implementations, the sensor captures UWB waveforms which are analyzed by an algorithm which compares successive waveforms to each other. If they are very similar, it is assumed the fetus is not moving significantly. The system can generate a time-series of $1^{st}$ risk scores less fetal movement results in higher risk scores based on the characteristics of the fetal activity; generate a time-series of $2^{nd}$ risk scores which are based on multiple $1^{st}$ risk scores over time; and, generate an alert when the $2^{nd}$ risk score crosses a specified threshold value, where the threshold may be different for different women depending upon their age of gestation and other user characteristics.

In one embodiment, occasional questions pop up in the mobile app or are sent via email, SMS, or other transmission to the user to ask how they are feeling about their pregnancy or outlook on life in general (eg quick response from 1-10). If one very low or many somewhat low responses are given the algorithm alerts doctor that counselling or medication may be necessary.

In one embodiment, the system 1 provides responses to help uplift the user. Example phrases include "Pregnancy is an overwhelming experience but believing that you will have a positive outcome actually increases the likelihood of success. Remember this and know that even on the hardest days of pregnancy that millions of other women are sharing this journey with you right now. Stay strong and enjoy your pregnancy. Even though it is a difficult road at times, it is one that leads to immeasurable joy." Other phrases include more clinical and scientific rationale to stay positive and include actionable options. For example, "Staying positive during pregnancy decreases your risk on preterm birth by 40%. Avoiding drugs, alcohol, and smoking is proven to improve the IQ of your future child. If you are depressed or are abusing substances and would like to talk to one of our pregnancy counselors in a judgment-free environment right now, please click here or call xxx-xxxx."

In one embodiment, the algorithm calculates depression risk in a similar manner to orientation or activity risk. If the variable called "Emotional Health" dips below a certain health threshold level, the system issues alerts to care providers and/or sends feedback to the user. This feedback may be in the form of positive phrases to encourage the user or suggestions of things the user can do to improve their mental state. In one embodiment, these include suggestions to take a deep breath, perform a mental exercise to focus on things they are grateful for, take a short walk, give a family member a hug, or envision their future healthy birth and child.

In one embodiment, the system 1 periodically issues multiple choice questions to the user by way of the device 10, such as through the indicators 24, which can include an LCD or other well-known smart device screen operationally integrated with the microcontroller 12 and other electronic components, as would be understood. They can be sent directly through the mobile app or as an email or text message. In one embodiment, a question asks "How optimistic are you that you will have a healthy pregnancy and delivery?" The answers have a range of 10 choices from 1 to 10 where 1 is Very Pessimistic and 10 is Very Optimistic. In one embodiment, if the user responds with a 1, 2, 3, or 4, the algorithm prompts an additional question to gain more insight into the current mental state of the user.

In some embodiments, the application or software for the device may comprise a comprehensive diagnostic and therapy system that suggests a variety of tests and treatments for pregnant women. In some embodiments, based on a user's risk profile, the app suggests the user get a diagnostic test (blood protein markers or genetic based) to see if they are at high risk for any pregnancy diseases. Manual user data inputs, diagnostic test results, as well as position and activity monitor data may all feed into one comprehensive algorithm that continually assesses a user's estimated risk for disease initiation and progression and offers feedback to help manage risk.

In some embodiments, the doctor or care provider can communicate directly to the user via the device. This may include recommendations to lower activity or change positions based on data the doctor receives from the device, or may include communication unrelated to the data generated by the device. In some embodiments, the daily % compliance with bed rest and/or reduced activity may be sent to the user and/or doctor.

In some embodiments, a sensing device may measure user position and may send that data in real time or periodically (e.g., every few hours) to the user's phone or other Wi-Fi/Bluetooth device.

Although the disclosure has been described with reference to certain embodiments, persons skilled in the art will recognize that changes may be made in form and detail without departing from the spirit and scope of the disclosed apparatus, systems and methods.

I claim:

1. A system for reducing fetal risk in a pregnant user, comprising:
    a. a wearable device comprising:
        i. a memory unit;
        ii. at least one sensor configured to monitor the orientation of the abdomen of the user and generate sensor data; and
        iii. a processor coupled to the at least one sensor and configured to record abdominal orientation over time and monitor fetal risk of at least one pregnancy condition by processing orientation sensor data to identify risk values associated with the orientation of the abdomen to produce a time series of identified fetal risk values; and
    b. a fixed orientation external mounting device, garment or adhesive configured to mount the wearable device on the user in a fixed orientation.

2. The system of claim 1, wherein the at least one pregnancy condition is selected from the group consisting of low birth weight, stillbirth, IUGR, premature birth, preeclampsia, gestational diabetes and gestational hypertension.

3. The system of claim 2, wherein the device is configured to output a warning when the orientation of the abdomen is supine.

4. The system of claim 2, further comprising a communication device.

5. The system of claim 1, wherein the device is configured to alert the user of possible pregnancy conditions on the basis of the recorded orientation over time.

6. The system of claim 1, wherein the risk values are calculated via at least one physiological parameter including estimated cumulative inferior vena caval restriction caused by specified body orientations.

7. A system for reducing fetal health risks in a pregnant user, the system comprising:
    a. a fetal risk device comprising a housing;
    b. a transmission component disposed in the housing;
    c. at least one sensor configured to estimate an orientation of the abdomen of the user;
    d. a timer configured to calculate the duration of the orientation to establish fetal risk values; and
    e. an external mounting device configured to mount the fetal risk device on the pregnant user in a fixed orientation,
    wherein the system is configured to output a warning when a time threshold is exceeded.

8. The system of claim 7, wherein the system is configured to alert the user when the identified fetal risk values exceed an established risk threshold.

9. The system of claim 8, wherein the processor is in electronic communication with at least one database configured to revise at least one of the time threshold and/or risk threshold on the basis of data gathered from users.

10. The system of claim 7, wherein the at least one sensor is selected from the group consisting of an acoustic sensor, an ultrasound sensor, a bio-impedance sensor, a voltage sensor, a current sensor, an accelerometer, an ultra-wideband sensor, a blood oxygen sensor and a light sensor.

11. The system of claim 7, further comprising an external sensor disposed outside the housing.

12. A wearable system for reducing stillbirth, IUGR, premature birth or preeclampsia risks in a pregnant user, comprising:
    a. a wearable device housing comprising:
        i. a memory unit;
        ii; a transmission unit;
        iii. at least one sensor configured to generate fetal data relating to abdominal orientation; and
        iv. a processor coupled to the at least one sensor so as to receive the orientation data; and
    b. an external mounting device configured to mount the wearable device on the pregnant user in a fixed orientation,
    wherein the processor is configured to receive and analyze the orientation data from the at least one sensor to determine whether the abdomen of the user is in a defined target orientation and provide feedback to the user to encourage the user to turn to a different orientation.

13. The system of claim 12, wherein the processor is configured to calculate and produce a time-series of fetal risk scores in response to the orientation data, and wherein the fetal risk scores can be wirelessly transmitted via the transmission unit.

14. The system of claim 12, wherein the processor configured to:
    a. monitor the orientation of the of the user abdomen by processing the fetal data;
    b. estimate the orientation of the abdomen of the user;
    c. assign a health zone to the orientation;
    d. assign time thresholds for each health zone; and
    e. output a warning when a time threshold is exceeded.

15. The system of claim 12, wherein the processor is a mobile phone.

16. The system of claim 12, wherein the processor calculates user duration within the defined target orientation.

17. The system of claim 12, wherein the defined target orientation is reclined or supine.

18. The system of claim 12, wherein the feedback mechanism is configured to transmit a warning in response to the orientation data such that stillbirth, IUGR, premature birth or preeclampsia risk is mitigated.

19. The system of claim 12, wherein the feedback mechanism is configured to transmit a vibrational alert.

20. The system of claim 12, wherein the processor and at least one sensor are not housed in the same enclosure.

* * * * *